(12) United States Patent
Wang et al.

(10) Patent No.: US 11,117,956 B2
(45) Date of Patent: Sep. 14, 2021

(54) ANTI-O1 ANTIBODIES AND USES THEREOF

(71) Applicants: MEDIMMUNE, LLC, Gaithersburg, MD (US); HUMABS BIOMED SA, Bellinzona (CH)

(72) Inventors: Qun Wang, Gaithersburg, MD (US); Charles Stover, Gaithersburg, MD (US); Meghan Pennini, Gaithersburg, MD (US); Chew-shun Chang, Gaithersburg, MD (US); Xiaodong Xiao, Gaithersburg, MD (US); Jamese Hilliard, Gaithersburg, MD (US); Gilad Kaplan, Gaithersburg, MD (US); Davide Corti, Bellinzona (CH); Elisabetta Cameroni, Bellinzona (CH); Martina Beltramello, Bellinzona (CH)

(73) Assignees: MedImmune, LLC, Gaithersburg, MD (US); Humabs BioMed SA, Bellinzona (CH)

( * ) Notice: Subject to any disclaimer, the term of this patent is extended or adjusted under 35 U.S.C. 154(b) by 57 days.

(21) Appl. No.: 16/342,688

(22) PCT Filed: Oct. 16, 2017

(86) PCT No.: PCT/US2017/056725
§ 371 (c)(1),
(2) Date: Apr. 17, 2019

(87) PCT Pub. No.: WO2018/075375
PCT Pub. Date: Apr. 26, 2018

(65) Prior Publication Data
US 2020/0231660 A1    Jul. 23, 2020

Related U.S. Application Data

(60) Provisional application No. 62/410,005, filed on Oct. 19, 2016.

(51) Int. Cl.
| | | |
|---|---|---|
| *C07K 16/12* | (2006.01) | |
| *A61P 31/04* | (2006.01) | |
| *C12N 15/63* | (2006.01) | |
| A61K 31/407 | (2006.01) | |
| A61K 38/00 | (2006.01) | |
| A61K 39/00 | (2006.01) | |

(52) U.S. Cl.
CPC .......... *C07K 16/1228* (2013.01); *A61P 31/04* (2018.01); *C12N 15/63* (2013.01); *A61K 31/407* (2013.01); *A61K 38/00* (2013.01); *A61K 2039/505* (2013.01); *C07K 2317/21* (2013.01); *C07K 2317/24* (2013.01); *C07K 2317/31* (2013.01); *C07K 2317/565* (2013.01); *C07K 2317/734* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,474,893 A | 10/1984 | Reading |
| 4,714,681 A | 12/1987 | Reading |
| 4,816,567 A | 3/1989 | Cabilly et al. |
| 4,925,648 A | 5/1990 | Hansen et al. |
| 4,946,778 A | 8/1990 | Ladner et al. |
| 5,179,018 A | 1/1993 | Bogard et al. |
| 5,545,806 A | 8/1996 | Lonberg et al. |
| 5,545,807 A | 8/1996 | Surani et al. |
| 5,569,825 A | 10/1996 | Lonberg et al. |
| 5,573,920 A | 11/1996 | Randle |
| 5,601,819 A | 2/1997 | Wong et al. |
| 5,624,821 A | 4/1997 | Winter et al. |
| 5,625,126 A | 4/1997 | Lonberg et al. |
| 5,633,425 A | 5/1997 | Lonberg et al. |
| 5,648,260 A | 7/1997 | Winter et al. |
| 5,661,016 A | 8/1997 | Lonberg et al. |
| 5,677,425 A | 10/1997 | Bodmer et al. |
| 5,731,168 A | 3/1998 | Carter et al. |
| 5,750,373 A | 5/1998 | Garrard et al. |
| 5,807,706 A | 9/1998 | Carter et al. |
| 5,821,333 A | 10/1998 | Carter et al. |

(Continued)

FOREIGN PATENT DOCUMENTS

| | | |
|---|---|---|
| EP | 184187 A2 | 6/1986 |
| EP | 239400 A2 | 9/1987 |

(Continued)

OTHER PUBLICATIONS

Sela-Culang et al. 2013 (The structural basis of antibody-antigen recognition; Frontiers in Immunology 4(302):1-13) (Year: 2013).*

(Continued)

*Primary Examiner* — Mary Maille Lyons
(74) *Attorney, Agent, or Firm* — Sterne, Kessler, Goldstein & Fox, P.L.L.C.

(57) ABSTRACT

The present disclosure provides binding proteins (e.g., antibodies or antigen binding fragments thereof) that specifically bind to *Klebsiella pneumoniae* O1 and induce opsonophagocytic killing of *Klebsiella* (e.g., *Klebsiella pneumoniae*). The present disclosure also provides methods of reducing *Klebsiella* (e.g., *Klebsiella pneumoniae*) or treating or preventing *Klebsiella* (e.g., *Klebsiella pneumoniae*) infection in a subject comprising administering the *Klebsiella pneumoniae* O1 binding proteins, (e.g., antibodies or antigen-binding fragments thereof) to the subject.

25 Claims, 17 Drawing Sheets

Specification includes a Sequence Listing.

(56) References Cited

U.S. PATENT DOCUMENTS

| | | | |
|---|---|---|---|
| 5,869,046 | A | 2/1999 | Presta et al. |
| 5,885,573 | A | 3/1999 | Bluestone et al. |
| 5,885,793 | A | 3/1999 | Griffiths et al. |
| 5,969,108 | A | 10/1999 | McCafferty et al. |
| 6,121,022 | A | 9/2000 | Presta et al. |
| 6,165,745 | A | 12/2000 | Ward et al. |
| 6,172,197 | B1 | 1/2001 | McCafferty et al. |
| 6,180,377 | B1 | 1/2001 | Morgan et al. |
| 6,194,551 | B1 | 2/2001 | Idusogie et al. |
| 6,277,375 | B1 | 8/2001 | Ward |
| 6,300,064 | B1 | 10/2001 | Knappik et al. |
| 6,521,404 | B1 | 2/2003 | Griffiths et al. |
| 6,528,624 | B1 | 3/2003 | Idusogie et al. |
| 6,544,731 | B1 | 4/2003 | Griffiths et al. |
| 6,555,313 | B1 | 4/2003 | Griffiths et al. |
| 6,582,915 | B1 | 6/2003 | Griffiths et al. |
| 6,593,081 | B1 | 7/2003 | Griffiths et al. |
| 6,653,068 | B2 | 11/2003 | Frisch et al. |
| 6,706,484 | B1 | 3/2004 | Knappik et al. |
| 6,737,056 | B1 | 5/2004 | Presta |
| 6,821,505 | B2 | 11/2004 | Ward |
| 7,083,784 | B2 | 8/2006 | Dall'Acqua et al. |
| 7,122,637 | B2 | 10/2006 | Presta |
| 7,183,387 | B1 | 2/2007 | Presta |
| 7,264,963 | B1 | 9/2007 | Knappik et al. |
| 7,317,091 | B2 | 1/2008 | Lazar et al. |
| 7,332,581 | B2 | 2/2008 | Presta |
| 7,335,742 | B2 | 2/2008 | Presta |
| 7,355,008 | B2 | 4/2008 | Stavenhagen et al. |
| 7,371,826 | B2 | 5/2008 | Presta |
| 7,658,921 | B2 | 2/2010 | Dall'Acqua et al. |
| 2002/0155537 | A1 | 10/2002 | Carter et al. |
| 2003/0020734 | A1 | 1/2003 | Yin et al. |
| 2004/0002587 | A1 | 1/2004 | Watkins et al. |
| 2004/0132101 | A1 | 7/2004 | Lazar et al. |
| 2005/0074821 | A1 | 4/2005 | Wild et al. |
| 2007/0065444 | A1 | 3/2007 | North et al. |
| 2010/0330078 | A1 | 12/2010 | Bender et al. |
| 2013/0243792 | A1 | 9/2013 | Vogels et al. |
| 2015/0252025 | A1 | 9/2015 | Poyurovsky et al. |
| 2017/0073397 | A1 | 3/2017 | Wang et al. |

FOREIGN PATENT DOCUMENTS

| | | | | |
|---|---|---|---|---|
| GB | 2188638 | A | 10/1987 | |
| WO | WO-91/00360 | A1 | 1/1991 | |
| WO | WO-92/01047 | A1 | 1/1992 | |
| WO | WO-92/05793 | A1 | 4/1992 | |
| WO | WO-92/08802 | A1 | 5/1992 | |
| WO | WO-93/11161 | A1 | 6/1993 | |
| WO | WO-93/17715 | A1 | 9/1993 | |
| WO | WO-94/13804 | A1 | 6/1994 | |
| WO | WO-99/58572 | A1 | 11/1999 | |
| WO | WO-00/44788 | A1 | 8/2000 | |
| WO | WO-02/96948 | A2 | 12/2002 | |
| WO | WO-2011/069164 | A2 | 6/2011 | |
| WO | WO-2012/006635 | A1 | 1/2012 | |
| WO | WO-2015/175874 | A2 | 11/2015 | |
| WO | WO-2016/131503 | A1 | 8/2016 | |
| WO | WO-2016131503 | A1 * | 8/2016 | ............. A61K 39/40 |
| WO | WO 2017/064258 | A1 | 4/2017 | |
| WO | WO-2018027124 | A1 | 2/2018 | |
| WO | WO-2018075375 | A1 | 4/2018 | |

OTHER PUBLICATIONS

Goel et al. 2004 (Plasticity within the Antigen Combining Site May Manifest as Molecular Mimicry in the Humoral Immune Response; The Journal of Immunology 173(12):7358-7367) (Year: 2004).*

Lloyd et al. 2009 (Modelling the human immune response: performance of a 1011 human antibody repertoire against a broad panel of therapeutically relevant antigens. Protein Engineering, Design & Selection 22(3):159-168) (Year: 2009).*

Ahmadi et al. 1998 (Antibodies to Klebsiella pneumoniae lipopolysaccharide in patients with ankylosing spondylitis; British Journal of Rheumatology 37:1330-1333) (Year: 1998).*

Held et al. 2000 (Binding to and Opsonophagocytic Activity of O-Antigen-Specific Monoclonal Antibodies against Encapsulated and Nonencapsulated Klebsiella pneumoniae Serotype O1 Strains; Infection and Immunity; 68(5): 2402-2409 (Year: 2000).*

Andersen et al., Recombinant protein expression for therapeutic applications, Curr. Opin. Biotechnol., 13(2):117-23 (Apr. 2002).

Bagshawe et al., Antibodyenzyme conjugates can generate cytotoxic drugs from inactive precursors at tumor sites.Antibody, Immunoconjugates and Radiopharmaceuticals 4, 915-22 (1991).

Barbas et al., In vitro evolution of a neutralizing human antibody to human immunodeficiency virus type 1 to enhance affinity and broaden strain cross-reactivity, Proc. Natl. Acad. Sci. USA, 91(9):3809-13 (Apr. 1994).

Bird et al., Single-chain antigen-binding proteins, Science, 242(4877):423-6 (Oct. 1988).

Boerner et al., Production of antigen-specific human monoclonal antibodies from in vitro-primed human splenocytes, J. Immunol., 147(1):86-95 (Jul. 1991).

Brade et al., A monoclonal antibody with specificity for the genus *Klebsiella* binds to a common epitope located in the core region of Klebsiella lipopolysaccharide, J. Endotoxin Res., 7(2):119-24 (2001).

Chadd et al., Therapeutic antibody expression technology, Curr. Opin. Biotechnol., 12(2):188-94 (Apr. 2001).

Cheung et al., Epitope-specific antibody response to the surface antigen of duck hepatitis B virus in infected ducks, Virology, 176(2):546-52 (Jun. 1990).

Chothia et al., Canonical structures for the hypervariable regions of immunoglobulins, J. Mol. Biol., 196(4):901-17 (Aug. 1987).

Clackson et al., Making antibody fragments using phage display libraries, Nature, 352(6336):624-8 (Aug. 1991).

Clarke et al., Molecular cloning of the rfb region of Klebsiella pneumoniae serotype O1:K20: the rfb gene cluster is responsible for synthesis of the D-galactan I O polysaccharide, J. Bacteriol., 174(14):4614-21 (Jul. 1992).

Dall'Acqua et al., Properties of human IgG1s engineered for enhanced binding to the neonatal Fc receptor (FcRn), J. Biol. Chem., 281(33):23514-24 (Aug. 2006).

Gram et al., In vitro selection and affinity maturation of antibodies from a naive combinatorial immunoglobulin library, Proc. Natl. Acad. Sci. USA, 89(8):3576-80 (Apr. 1992).

Holliger et al., "Diabodies": small bivalent and bispecific antibody fragments, Proc. Natl. Acad. Sci. USA, 90(14):6444-8 (Jul. 1993).

Holliger et al., Engineering bispecific antibodies, Curr. Opin. Biotechnol., 4(4):446-9 (Aug. 1993).

Hoogenboom et al., By-passing Immunisation: Human antibodies from synthetic repertoires of germline $V_H$ gene segments rearranged in vitro, J. Mol. Biol., 227:381-8 (1992).

Hsieh et al., D-galactan II is an immunodominant antigen in O1 lipopolysaccharide and affects virulence in Klebsiella pneumoniae: implication in vaccine design, Front Microbiol., 5:608 (Nov. 2014).

Hsieh et al., Lipopolysaccharide O1 antigen contributes to the virulence in Klebsiella pneumoniae causing pyogenic liver abscess. PLoS One, 7(3):e33155 (2012).

Hu et al., Minibody: A novel engineered anti-carcinoembryonic antigen antibody fragment (single-chain Fv-CH3) which exhibits rapid, high-level targeting of xenografts, Cancer Res., 56(13):3055-61 (Jul. 1996).

Huse et al., Generation of a large combinatorial library of the immunoglobulin repertoire in phage lambda, Science, 246(4935):1275-81 (Dec. 1989).

Huston et al., Protein engineering of antibody binding sites: recovery of specific activity in an anti-digoxin single-chain Fv analogue produced in *Escherichia coli*, Proc. Natl. Acad. Sci. USA, 85(16):5879-83 (1988).

International Application No. PCT/US2017/056725, International Search Report and Written Opinion, dated Apr. 3, 2018.

Iredell et al., Antibiotic resistance in Enterobacteriaceae: mechanisms and clinical implications, BMJ, 352:h6420 (Feb. 2016).

(56) References Cited

OTHER PUBLICATIONS

Kirkland et al., Analysis of the fine specificity and cross-reactivity of monoclonal anti-lipid A antibodies, J. Immunol., 137(11):3614-9 (Dec. 1986).
Knappik et al., Fully synthetic human combinatorial antibody libraries (HuCAL) based on modular consensus frameworks and CDRs randomized with trinucleotides, J. Mol. Biol., 296(1):57-86 (Feb. 2000).
Kohler et al., Continuous cultures of fused cells secreting antibody of predefined specificity, Nature, 256(5517):495-7 (Aug. 1975).
Kostelny et al., Formation of a bispecific antibody by the use of leucine zippers, J. Immunol., 148(5):1547-53 (Mar. 1992).
Krebs et al., High-throughput generation and engineering of recombinant human antibodies, J. Immunol. Methods, 254(1-2):67-84 (Aug. 2001).
Larrick et al., Producing proteins in transgenic plants and animals, Curr. Opin. Biotechnol., 12(4):411-8 (Aug. 2001).
Ledermann et al., A phase-I study of repeated therapy with radiolabelled antibody to carcinoembryonic antigen using intermittent or continuous administration of cyclosporin A to suppress the immune response, Int. J. Cancer, 47(5):659-64 (Mar. 1991).
Lefranc et al., IMGT unique numbering for immunoglobulin and T cell receptor variable domains and Ig superfamily V-like domains, Dev. Comp. Immunol., 27(1):55-77 (Jan. 2003).
Lowe et al., Combinatorial protein biochemistry for therapeutics and proteomics, Curr. Pharm. Biotechnol., 5(1):17-27 (2004).
Marks et al., By-passing immunization. Human antibodies from V-gene libraries displayed on phage, J. Mol. Biol., 222(3):581-97 (Dec. 1991).
Marks et al., By-passing immunization: building high affinity human antibodies by chain shuffling, Biotechnology (NY), 10(7):779-83 (Jul. 1992).
McCafferty et al., Phage antibodies: filamentous phage displaying antibody variable domains, Nature, 348(6301):552-4 (Dec. 1990).
Moldenhauer et al., Identity of HML-1 antigen on intestinal intraepithelial T cells and of B-ly7 antigen on hairy cell leukaemia, Scand. J. Immunol., 32(2):77-82 (Aug. 1990).
Morel et al., Monoclonal antibodies to bovine serum albumin: affinity and specificity determinations, Mol. Immunol., 25(1):7-15 (Jan. 1988).
Oganesyan et al., Structural characterization of a human Fc fragment engineered for lack of effector functions, Acta Crystallogr. D Biol. Crystallogr., 64(Pt. 6):700-4 (Jun. 2008).
Pinna et al., Clonal dissection of the human memory B-cell repertoire following infection and vaccination, Eur. J. Immunol., 39(5):1260-70 (May 2009).
Plückthun, Antibody engineering: advances from the use of *Escherichia coli* expression systems, Biotechnology(NY):9(6):545-51 (Jun. 1991).
Podschun et al., *Klebsiella* spp. as nosocomial pathogens: epidemiology, taxonomy, typing methods, and pathogenicity factors, Clin. Microbiol. Rev., 11(4):589-603 (Oct. 1998).
Reiter et al., Engineering antibody Fv fragments for cancer detection and therapy: disulfide-stabilized Fv fragments, Nat. Biotechnol., 14(10):1239-45 (Oct. 1996).
Ridgway et al., 'Knobs-into-holes' engineering of antibody CH3 domains for heavy chain heterodimerization, Protein Eng., 9(7):617-21 (Jul. 1996).
Rothe et al., The human combinatorial antibody library HuCAL GOLD combines diversification of all six CDRs according to the natural immune system with a novel display method for efficient selection of high-affinity antibodies, J. Mol. Biol., 376(4):1182-200 (Feb. 2008).
Rukavina et al., Protective effect of antilipopolysaccharide monoclonal antibody in experimental Klebsiella infection, Infect. Immun., 65(5):1754-60 (May 1997).
Schier et al., Isolation of picomolar affinity anti-c-erbB-2 single-chain Fv by molecular evolution of the complementarity determining regions in the center of the antibody binding site, J. Mol. Biol., 263(4):551-67 (Nov. 1996).
Sheets et al., Efficient construction of a large nonimmune phage antibody library: the production of high-affinity human single-chain antibodies to protein antigens, Proc. Natl. Acad. Sci. USA, 95(11):6157-62 (May 1998).
Stahli et al., Distinction of epitopes by monoclonal antibodies, Methods Enzymol., 92:242-53 (1983).
Stemmer, Rapid evolution of a protein in vitro by DNA shuffling, Nature, 370(6488):389-91 (Aug. 1994).
Traggiai et al., An efficient method to make human monoclonal antibodies from memory B cells: potent neutralization of SARS coronavirus, Nat. Med., 10(8):871-5 (Aug. 2004).
Trautmann et al., Evaluation of a competitive ELISA method for the determination of Klebsiella O antigens, J. Med. Microbiol., 44(1):44-51 (Jan. 1996).
Tutt et al., Trispecific F(ab')3 derivatives that use cooperative signaling via the TCR/CD3 complex and CD2 to activate and redirect resting cytotoxic T cells, J. Immunol., 147(1):60-9 (Jul. 1991).
Vaughn et al., Human antibodies with sub-nanomolar affinities isolated from a large non-immunized phage display library, Nat. Biotechnol., 14(3):309-14 (Mar. 1996).
Wang et al., Target-Agnostic Identification of Functional Monoclonal Antibodies Against Klebsiella pneumoniae Multimeric MrkA Fimbrial Subunit, J. Infect. Dis., 213(11):1800-8 (Jun. 2016).
Ward et al., Binding activities of a repertoire of single immunoglobulin variable domains secreted from *Escherichia coli*, Nature, 341(6242):544-6 (Oct. 1989).
Whitfield et al., Expression of two structurally distinct D-galactan O antigens in the lipopolysaccharide of Klebsiella pneumoniae serotype O1, J. Bacteriol., 173(4):1420-31 (Feb. 1991).
Co-Pending U.S. Appl. No. 16/323,185, Int'l filing date Aug. 4, 2017, inventor Wang; Q., et al. (Unpublished).
International Search Report and Written Opinion dated Dec. 14, 2017 for International Application No. PCT/US2017/045480, ISA, United States, 18 pages.
Held, T.K., et al., "Binding to and Opsonophagocytic Activity of O-Antigen-Specific Monoclonal Antibodies against Encapsulated and Nonencapsulated Klebsiella pneumoniae Serotype 01 Strains," 68(5):2402-2409, American Society for Microbiology, United States (2000).
Rukavina, T., et al., "Protective effect of antilipopolysaccharide monoclonal antibody in experimental Klebsiella infection," Infect Immunology 65(5):1754-1760, American Society for Microbiology, United States (1997).
Sahly, H., et al., "Serum antibodies to klebsiella capsular polysaccharides in ankylosing spondylitis," Arthritis & Rheumatology 37(5): 754-759, American College of Rheumatology, United States (1994).
Sahly, H., et al., "Surfactant Protein D Binds selectively to Klebsiella pneumonia Lipopolysaccharides Containing Mannose-Rich O-Antigens," Journal of Immunology 169(6):3267-3274, American Association of Immunologists, United States (2002).
Van, N.M., et al., "Binding Studies of a Monoclonal Antibody Specific for 3-Deoxy-D-manno-Octulosonic Acid with a Panel of Klebsiella pneumoniae Lipopolysaccharides Representing All of the O Serotypes," Infection and Immunity 62(3):1052-1057, American Society for Microbiology, United States (1994).
Whitefield, C., et al., "Structural analysis of the O-antigen side chain polysaccharides in the lipopolysaccharides of Klebsiella serotypes O2(2a), O2(2a,2b), and O2(2a,2c)," Journal of Bacteriology, 174(15):4913-4919, American Society for Microbiology, United States (1992).
Beltramello, M., et al., "The human immune response to Dengue virus is dominated by highly crossreactive antibodies endowed with neutralizing and enhancing activity," Cell Host Microbe, 8(3):271-83, Cell Press, United States (Sep. 2010).
Szijarto, V., et al., "Both clades of the epidemic KPC-producing Klebsiella pneumoniae clone ST258 share a modified qalactan O-antigen type," Int. J. Med. Microbial., 306(2):89-98, Elsevier, Netherlands (Feb. 2016).
International Preliminary Report on Patentability for International Application No. PCT/US2017/045480, The International Bureau of WIPO, dated Feb. 5, 2019, 12 pages.

(56) References Cited

OTHER PUBLICATIONS

Sahly, H., et al., "Serum antibodies to Klebsiella capsular polysaccharides in ankylosing spondylitis," Arthritis Rheum., 37(5):754-9, American College of Rheumatology, United States (May 1994).

Sahly, H., et al., "Surfactant protein D binds selectively to Klebsiella pneumoniae lipopolysaccharides containing mannose-rich O-antigens," J. Immunol., 169(6):3267-74, The American Association of Immunologists, Inc., United States (Sep. 2002).

Trautmann, M., et al., "O antigen seroepidemiology of Klebsiella clinical isolates and implications for immunoprophylaxis of Klebsiella infections," Vaccine, 22(7):818-21, Elsevier, Netherlands (Feb. 2004).

\* cited by examiner

LPS-O1 ELISA

SBA of 4211-lux

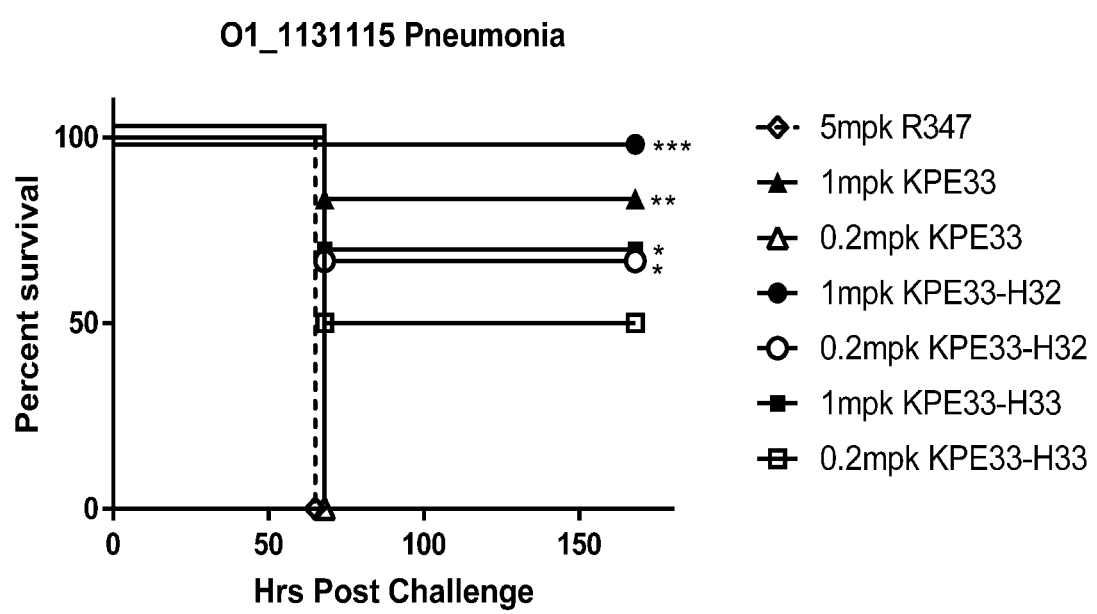

mAb/Abx Therapy
Pneumonia Model mAb/Abx Therapy
Bacteremia Model

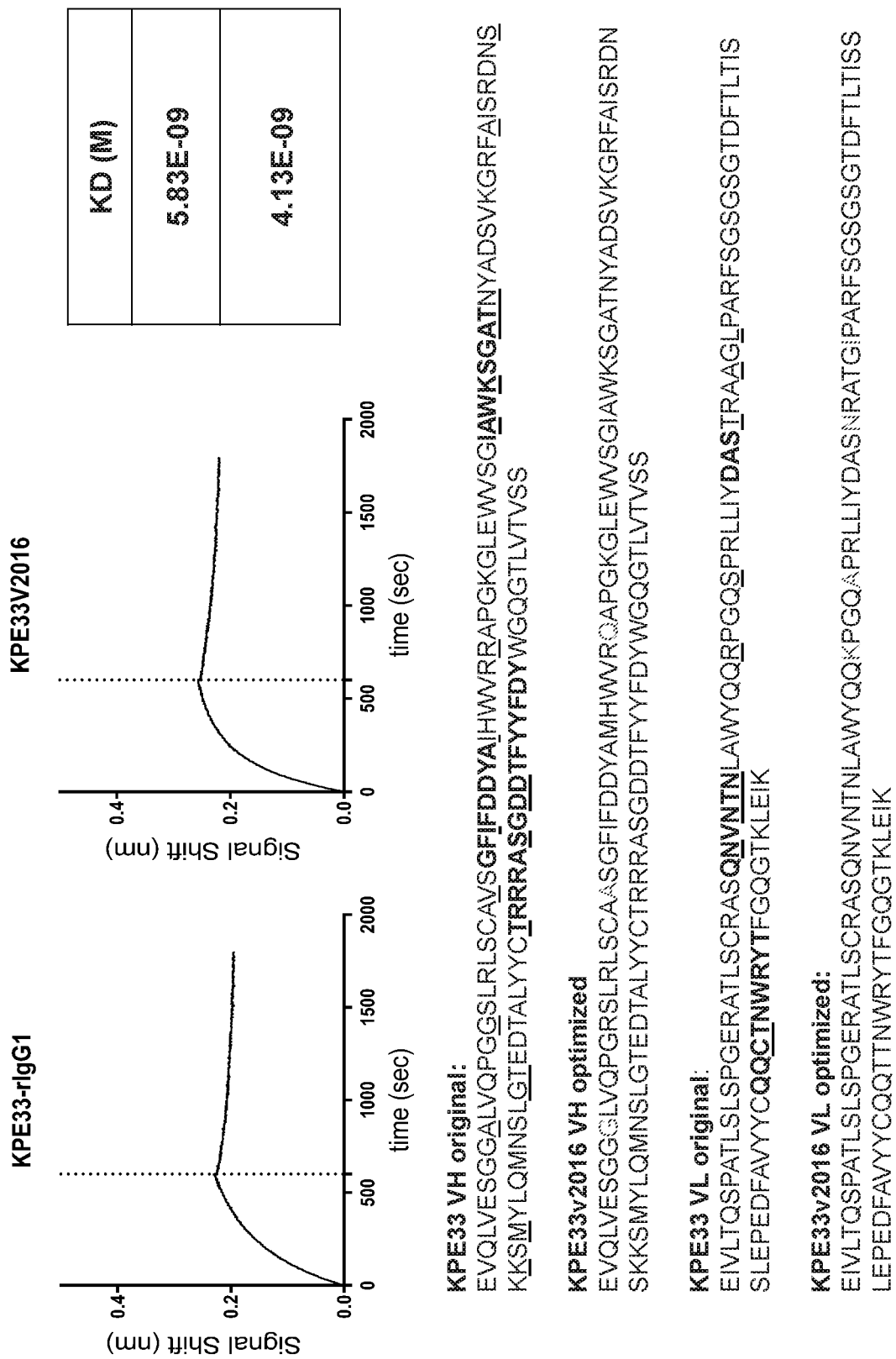

Pneumonia Model

Sa: *Staph aureus*
Kp: *Klebsiella pneumoniae*

Bacterial Organ Burden

Sa + Kp (Sa): Staph aureus counts
Sa + Kp (Kp): Klebsiella pneumoniae counts

Bacterial Organ Burden
*Klebsiella pneumoniae*

*K. pneumoniae* and *Staph aureus*
Co-infecton model

Φ represents $P<0.02$ compared to mixed infection,
* represents $P<0.03$ mixed infection (KP) vs. mono-infection (KP

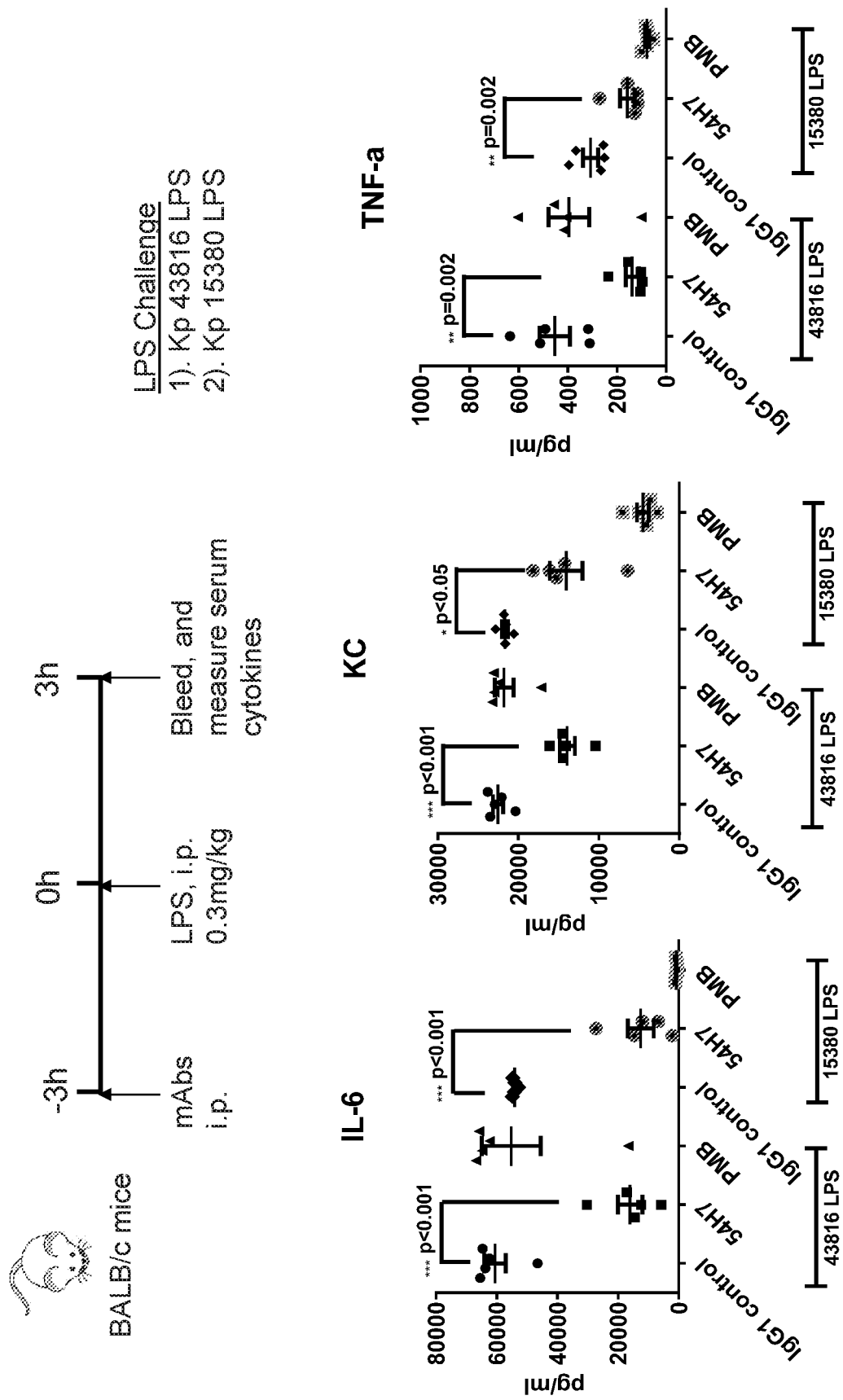

Pneumonia Model (Kp 43816) with O1 LPS mAb combination of three experiments
n=31 mAb/Abx Therapy
Pneumonia Model (Kp8045)

Challenge = 1e4 CFU IN (T0)   Log Rank (Mantel-Cox) Test:
mAb = 1mpk IV (T+1)           R347 + MEM vs.
Abx = 1.5mpk SC (T+4)              *** 54H7 + MEM p< 0.0001

| Serotype | Structure |
|---|---|
| O1 | [-3)-β-Galp-(1-3)-α-Galp-(1-]$_m$-[β-Galf-(1-3)-α-Galp-(1-]$_n$-Core<br>D – Gal II             D – Gal I |
| O1, O2a, O2ac | -[β-Galf-(1-3)-α-Galp-(1-]$_m$-Core<br>D – Gal I |

```
                        SEQUENCE LISTING

<160> NUMBER OF SEQ ID NOS: 68

<210> SEQ ID NO 1
<211> LENGTH: 8
<212> TYPE: PRT
<213> ORGANISM: Artificial Sequence
<220> FEATURE:
<223> OTHER INFORMATION: KPE33 KPE33V2016 VH-CDR1

<400> SEQUENCE: 1

Gly Phe Ile Phe Asp Asp Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: KPE33  KPE33V2016 VH-CDR2

<400> SEQUENCE: 2

Ile Ala Trp Lys Ser Gly Ala Thr
1               5

<210> SEQ ID NO 3
<211> LENGTH: 16
<212> TYPE: PRT
<213> ORGANISM: Artificial Sequence
<220> FEATURE:
<223> OTHER INFORMATION: KPE33  KPE33V2016 VH-CDR3

<400> SEQUENCE: 3

Thr Arg Arg Arg Ala Ser Gly Asp Asp Thr Phe Tyr Tyr Phe Asp Tyr
1               5                   10                  15

<210> SEQ ID NO 4
<211> LENGTH: 6
<212> TYPE: PRT
<213> ORGANISM: Artificial Sequence
<220> FEATURE:
<223> OTHER INFORMATION: KPE33 KPE33V2016  VL-CDR1

<400> SEQUENCE: 4

Gln Asn Val Asn Thr Asn
1               5

<210> SEQ ID NO 5
<211> LENGTH: 3
<212> TYPE: PRT
<213> ORGANISM: Artificial Sequence
<220> FEATURE:
<223> OTHER INFORMATION: KPE33   KPE33V2016 VL-CDR2

<400> SEQUENCE: 5

Asp Ala Ser
1

<210> SEQ ID NO 6
<211> LENGTH: 9
<212> TYPE: PRT
```

<213> ORGANISM: Artificial Sequence
<220> FEATURE:
<223> OTHER INFORMATION: KPE33 VL-CDR2

<400> SEQUENCE: 6

Leu Ile Tyr Asp Ala Ser Thr Arg Ala
1               5

<210> SEQ ID NO 7
<211> LENGTH: 9
<212> TYPE: PRT
<213> ORGANISM: Artificial Sequence
<220> FEATURE:
<223> OTHER INFORMATION: KPE33 VL-CDR3

<400> SEQUENCE: 7

Gln Gln Cys Thr Asn Trp Arg Tyr Thr
1               5

<210> SEQ ID NO 8
<211> LENGTH: 123
<212> TYPE: PRT
<213> ORGANISM: Artificial Sequence
<220> FEATURE:
<223> OTHER INFORMATION: KPE33 VH Amino Acid Sequence

<400> SEQUENCE: 8

Glu Val Gln Leu Val Glu Ser Gly Gly Ala Leu Val Gln Pro Gly Gly
1               5                   10                  15

Ser Leu Arg Leu Ser Cys Ala Val Ser Gly Phe Ile Phe Asp Asp Tyr
            20                  25                  30

Ala Ile His Trp Val Arg Arg Ala Pro Gly Lys Gly Leu Glu Trp Val
        35                  40                  45

Ser Gly Ile Ala Trp Lys Ser Gly Ala Thr Asn Tyr Ala Asp Ser Val
    50                  55                  60

Lys Gly Arg Phe Ala Ile Ser Arg Asp Asn Ser Lys Lys Ser Met Tyr
65                  70                  75                  80

Leu Gln Met Asn Ser Leu Gly Thr Glu Asp Thr Ala Leu Tyr Tyr Cys
                85                  90                  95

Thr Arg Arg Arg Ala Ser Gly Asp Asp Thr Phe Tyr Tyr Phe Asp Tyr
            100                 105                 110

Trp Gly Gln Gly Thr Leu Val Thr Val Ser Ser
        115                 120

<210> SEQ ID NO 9
<211> LENGTH: 107
<212> TYPE: PRT
<213> ORGANISM: Artificial Sequence
<220> FEATURE:
<223> OTHER INFORMATION: KPE33 VL Amino Acid Sequence

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Val Asn Thr Asn
            20                  25                  30

Leu Ala Trp Tyr Gln Gln Arg Pro Gly Gln Ser Pro Arg Leu Leu Ile
        35                  40                  45

Tyr Asp Ala Ser Thr Arg Ala Ala Gly Leu Pro Ala Arg Phe Ser Gly
    50                  55                  60

Ser Gly Ser Gly Thr Asp Phe Thr Leu Thr Ile Ser Ser Leu Glu Pro

```
                    65                  70                  75                  80
Glu Asp Phe Ala Val Tyr Tyr Cys Gln Gln Cys Thr Asn Trp Arg Tyr
                    85                  90                  95

Thr Phe Gly Gln Gly Thr Lys Leu Glu Ile Lys
            100                 105
```

<210> SEQ ID NO 10
<211> LENGTH: 9
<212> TYPE: PRT
<213> ORGANISM: Artificial Sequence
<220> FEATURE:
<223> OTHER INFORMATION: KPE33V2016 VL-CDR2

<400> SEQUENCE: 10

```
Leu Ile Tyr Asp Ala Ser Asn Arg Ala
1               5
```

<210> SEQ ID NO 11
<211> LENGTH: 9
<212> TYPE: PRT
<213> ORGANISM: Artificial Sequence
<220> FEATURE:
<223> OTHER INFORMATION: KPE33V2016 VL-CDR3

<400> SEQUENCE: 11

```
Gln Gln Thr Thr Asn Trp Arg Tyr Thr
1               5
```

<210> SEQ ID NO 12
<211> LENGTH: 123
<212> TYPE: PRT
<213> ORGANISM: Artificial Sequence
<220> FEATURE:
<223> OTHER INFORMATION: KPE33V2016 VH Amino Acid Sequence

<400> SEQUENCE: 12

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ile Phe Asp Asp Tyr
                20                  25                  30

Ala Met His Trp Val Arg Gln Ala Pro Gly Lys Gly Leu Glu Trp Val
            35                  40                  45

Ser Gly Ile Ala Trp Lys Ser Gly Ala Thr Asn Tyr Ala Asp Ser Val
        50                  55                  60

Lys Gly Arg Phe Ala Ile Ser Arg Asp Asn Ser Lys Lys Ser Met Tyr
65                  70                  75                  80

Leu Gln Met Asn Ser Leu Gly Thr Glu Asp Thr Ala Leu Tyr Tyr Cys
                85                  90                  95

Thr Arg Arg Arg Ala Ser Gly Asp Asp Thr Phe Tyr Tyr Phe Asp Tyr
            100                 105                 110

Trp Gly Gln Gly Thr Leu Val Thr Val Ser Ser
        115                 120
```

<210> SEQ ID NO 13
<211> LENGTH: 107
<212> TYPE: PRT
<213> ORGANISM: Artificial Sequence
<220> FEATURE:
<223> OTHER INFORMATION: KPE33V2016 VL Amino Acid Sequence

<400> SEQUENCE: 13

```
Glu Ile Val Leu Thr Gln Ser Pro Ala Thr Leu Ser Leu Ser Pro Gly
```

```
                1               5                  10                 15
            Glu Arg Ala Thr Leu Ser Cys Arg Ala Ser Gln Asn Val Asn Thr Asn
                            20                 25                 30

Leu Ala Trp Tyr Gln Gln Lys Pro Gly Gln Ala Pro Arg Leu Leu Ile
                        35                 40                 45

Tyr Asp Ala Ser Asn Arg Ala Thr Gly Ile Pro Ala Arg Phe Ser Gly
                    50                 55                 60

Ser Gly Ser Gly Thr Asp Phe Thr Leu Thr Ile Ser Ser Leu Glu Pro
            65                 70                 75                 80

Glu Asp Phe Ala Val Tyr Tyr Cys Gln Gln Tyr Thr Asn Trp Arg Tyr
                            85                 90                 95

Thr Phe Gly Gln Gly Thr Lys Leu Glu Ile Lys
                            100                105

<210> SEQ ID NO 14
<211> LENGTH: 8
<212> TYPE: PRT
<213> ORGANISM: Artificial Sequence
<220> FEATURE:
<223> OTHER INFORMATION: KPA27 VH-CDR1

<400> SEQUENCE: 14

Glu Asn Thr Phe Asn Asp Phe Tyr
1               5

<210> SEQ ID NO 15
<211> LENGTH: 8
<212> TYPE: PRT
<213> ORGANISM: Artificial Sequence
<220> FEATURE:
<223> OTHER INFORMATION: KPA27 VH-CDR2

<400> SEQUENCE: 15

Ile His Pro Asp Gly Val Val Thr
1               5

<210> SEQ ID NO 16
<211> LENGTH: 14
<212> TYPE: PRT
<213> ORGANISM: Artificial Sequence
<220> FEATURE:
<223> OTHER INFORMATION: KPA27 VH-CDR3

<400> SEQUENCE: 16

Met Arg Asp Gly Pro Gly Ser Glu Gly Ser Trp Phe Asp Tyr
1               5                  10

<210> SEQ ID NO 17
<211> LENGTH: 6
<212> TYPE: PRT
<213> ORGANISM: Artificial Sequence
<220> FEATURE:
<223> OTHER INFORMATION: KPA27 VL-CDR1

<400> SEQUENCE: 17

Gln Pro Val Ser Asn Arg
1               5

<210> SEQ ID NO 18
<211> LENGTH: 3
<212> TYPE: PRT
<213> ORGANISM: Artificial Sequence
<220> FEATURE:
<223> OTHER INFORMATION: KPA27  VL-CDR2
```

<400> SEQUENCE: 18

Lys Ala Ser
1

<210> SEQ ID NO 19
<211> LENGTH: 9
<212> TYPE: PRT
<213> ORGANISM: Artificial Sequence
<220> FEATURE:
<223> OTHER INFORMATION: KPA27 VL-CDR2

<400> SEQUENCE: 19

Leu Ile Tyr Lys Ala Ser Thr Leu Gln
1               5

<210> SEQ ID NO 20
<211> LENGTH: 5
<212> TYPE: PRT
<213> ORGANISM: Artificial Sequence
<220> FEATURE:
<223> OTHER INFORMATION: KPA27 VL-CDR3

<400> SEQUENCE: 20

Gln Gln Ser Gln Thr
1               5

<210> SEQ ID NO 21
<211> LENGTH: 121
<212> TYPE: PRT
<213> ORGANISM: Artificial Sequence
<220> FEATURE:
<223> OTHER INFORMATION: KPA27 VH Amino Acid Sequence

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Glu Asn Thr Phe Asn Asp Phe
            20                  25                  30

Tyr Met His Trp Val Arg Gln Ala Pro Gly Gln Gly Leu Glu Trp Met
        35                  40                  45

Gly Trp Ile His Pro Asp Gly Val Val Thr Asn Tyr Ala Gln Lys Phe
    50                  55                  60

Gln Gly Arg Val Thr Met Thr Arg Asp Thr Ser Ile Asn Thr Val Tyr
65                  70                  75                  80

Met Glu Leu Asn Gly Leu Ile Ser Asp Asp Thr Ala Val Tyr Tyr Cys
                85                  90                  95

Met Arg Asp Gly Pro Gly Ser Glu Gly Ser Trp Phe Asp Tyr Trp Gly
            100                 105                 110

Gln Gly Thr Leu Val Thr Val Ser Ser
        115                 120

<210> SEQ ID NO 22
<211> LENGTH: 103
<212> TYPE: PRT
<213> ORGANISM: Artificial Sequence
<220> FEATURE:
<223> OTHER INFORMATION: KPA27 VL Amino Acid Sequence

<400> SEQUENCE: 22

Asp Ile Gln Met Thr Gln Ser Pro Ser Thr Leu Ser Ala Ser Val Gly
1               5                   10                  15

```
Asp Arg Val Thr Ile Thr Cys Arg Ala Ser Gln Pro Val Ser Asn Arg
             20                  25                  30

Leu Ala Trp Tyr Gln Gln Lys Pro Gly Arg Ala Pro Thr Leu Leu Ile
         35                  40                  45

Tyr Lys Ala Ser Thr Leu Gln Ser Gly Val Pro Leu Arg Phe Ser Gly
     50                  55                  60

Ser Gly Ser Gly Thr Glu Phe Thr Leu Thr Ile Ser Ser Leu Gln Ser
 65                  70                  75                  80

Asp Asp Phe Ala Thr Tyr Tyr Cys Gln Gln Ser Gln Thr Phe Gly Gln
                 85                  90                  95

Gly Thr Lys Val Glu Ile Lys
            100
```

<210> SEQ ID NO 23
<211> LENGTH: 10
<212> TYPE: PRT
<213> ORGANISM: Artificial Sequence
<220> FEATURE:
<223> OTHER INFORMATION: KBPJ4 VH-CDR1

<400> SEQUENCE: 23

```
Gly Asp Ser Val Ser Ser Asn Thr Ala Ala
 1               5                   10
```

<210> SEQ ID NO 24
<211> LENGTH: 9
<212> TYPE: PRT
<213> ORGANISM: Artificial Sequence
<220> FEATURE:
<223> OTHER INFORMATION: KBPJ4 VH-CDR2

<400> SEQUENCE: 24

```
Thr Tyr Tyr Arg Ser Glu Trp Tyr Asn
 1               5
```

<210> SEQ ID NO 25
<211> LENGTH: 10
<212> TYPE: PRT
<213> ORGANISM: Artificial Sequence
<220> FEATURE:
<223> OTHER INFORMATION: KBPJ4 VH-CDR3

<400> SEQUENCE: 25

```
Ala Arg Ile Ser Trp Asn Asp Leu Pro Ala
 1               5                   10
```

<210> SEQ ID NO 26
<211> LENGTH: 12
<212> TYPE: PRT
<213> ORGANISM: Artificial Sequence
<220> FEATURE:
<223> OTHER INFORMATION: KPJ4 VL-CDR1

<400> SEQUENCE: 26

```
Gln Ser Ile Leu Tyr Ser Ser His Asn Lys Asn Tyr
 1               5                   10
```

<210> SEQ ID NO 27
<211> LENGTH: 3
<212> TYPE: PRT
<213> ORGANISM: Artificial Sequence
<220> FEATURE:
<223> OTHER INFORMATION: KPJ4 VL-CDR2

<400> SEQUENCE: 27

```
Trp Ala Ser
1

<210> SEQ ID NO 28
<211> LENGTH: 9
<212> TYPE: PRT
<213> ORGANISM: Artificial Sequence
<220> FEATURE:
<223> OTHER INFORMATION: KPJ4 VL-CDR2

<400> SEQUENCE: 28

Leu Ile Tyr Trp Ala Ser Thr Arg Glu
1               5

<210> SEQ ID NO 29
<211> LENGTH: 9
<212> TYPE: PRT
<213> ORGANISM: Artificial Sequence
<220> FEATURE:
<223> OTHER INFORMATION: KPJ4 VL-CDR3

<400> SEQUENCE: 29

Gln Gln Tyr Cys Asn Ile Pro Tyr Thr
1               5

<210> SEQ ID NO 30
<211> LENGTH: 120
<212> TYPE: PRT
<213> ORGANISM: Artificial Sequence
<220> FEATURE:
<223> OTHER INFORMATION: KBJ4 VH Amino Acid Sequence

<400> SEQUENCE: 30

Gln Val Gln Leu Gln Gln Ser Gly Pro Gly Leu Val Arg Pro Ser Gln
1               5                   10                  15

Thr Leu Ser Leu Thr Cys Ala Ile Ser Gly Asp Ser Val Ser Ser Asn
            20                  25                  30

Thr Ala Ala Trp Asn Trp Ile Arg Gln Ser Pro Ser Arg Gly Leu Glu
        35                  40                  45

Trp Leu Gly Arg Thr Tyr Tyr Arg Ser Glu Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ile Ser Trp Asn Asp Leu Pro Ala Trp Gly Gln
            100                 105                 110

Gly Thr Leu Val Thr Val Ser Ser
        115                 120

<210> SEQ ID NO 31
<211> LENGTH: 113
<212> TYPE: PRT
<213> ORGANISM: Artificial Sequence
<220> FEATURE:
<223> OTHER INFORMATION: KPJ4 VL Amino Acid Sequence

<400> SEQUENCE: 31

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30
```

```
Ser His Asn Lys Asn Tyr Leu Ala Trp Tyr Gln Gln Lys Pro Gly Gln
         35                  40                  45

Pro Pro Lys Val Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Asn Leu Gln Ala Glu Asp Val Ala Val Tyr Tyr Cys Gln Gln
                 85                  90                  95

Tyr Cys Asn Ile Pro Tyr Thr Phe Gly Gln Gly Thr Lys Leu Glu Ile
            100                 105                 110

Lys

<210> SEQ ID NO 32
<211> LENGTH: 8
<212> TYPE: PRT
<213> ORGANISM: Artificial Sequence
<220> FEATURE:
<223> OTHER INFORMATION: KPB202 VH-CDR1

<400> SEQUENCE: 32

Gly Phe Thr Phe Ser Asn Phe Trp
1               5

<210> SEQ ID NO 33
<211> LENGTH: 8
<212> TYPE: PRT
<213> ORGANISM: Artificial Sequence
<220> FEATURE:
<223> OTHER INFORMATION: KPB202  VH-CDR2

<400> SEQUENCE: 33

Ile Asn Pro Asp Gly Ser Glu Lys
1               5

<210> SEQ ID NO 34
<211> LENGTH: 10
<212> TYPE: PRT
<213> ORGANISM: Artificial Sequence
<220> FEATURE:
<223> OTHER INFORMATION: KPB202 VH-CDR3

<400> SEQUENCE: 34

Ala Arg Leu Gly Pro Phe His Pro Asp Cys
1               5                   10

<210> SEQ ID NO 35
<211> LENGTH: 11
<212> TYPE: PRT
<213> ORGANISM: Artificial Sequence
<220> FEATURE:
<223> OTHER INFORMATION: KPB202 VL-CDR1

<400> SEQUENCE: 35

Gln Ser Leu Val His Ser Asp Gly Asn Thr Tyr
1               5                   10

<210> SEQ ID NO 36
<211> LENGTH: 3
<212> TYPE: PRT
<213> ORGANISM: Artificial Sequence
<220> FEATURE:
<223> OTHER INFORMATION: KPB202 VL-CDR2

<400> SEQUENCE: 36
```

```
Glu Val Ser
1

<210> SEQ ID NO 37
<211> LENGTH: 9
<212> TYPE: PRT
<213> ORGANISM: Artificial Sequence
<220> FEATURE:
<223> OTHER INFORMATION: KPB202 VL-CDR2

<400> SEQUENCE: 37

Leu Ile Tyr Glu Val Ser Asn Arg Asp
1               5

<210> SEQ ID NO 38
<211> LENGTH: 9
<212> TYPE: PRT
<213> ORGANISM: Artificial Sequence
<220> FEATURE:
<223> OTHER INFORMATION: KPB202 VL-CDR3

<400> SEQUENCE: 38

Met Gln Gly Thr His Trp Pro Trp Thr
1               5

<210> SEQ ID NO 39
<211> LENGTH: 117
<212> TYPE: PRT
<213> ORGANISM: Artificial Sequence
<220> FEATURE:
<223> OTHER INFORMATION: KPB202 VH Amino Acid Sequence

<400> SEQUENCE: 39

Glu Val Gln Leu Val Glu Ser Gly Gly Gly Leu Val Gln Pro Gly Gly
1               5                   10                  15

Ser Leu Ser Leu Ser Cys Ala Ala Ser Gly Phe Thr Phe Ser Asn Phe
            20                  25                  30

Trp Val Gly Trp Gly Arg Gln Ala Pro Gly Lys Gly Leu Glu Trp Val
        35                  40                  45

Ala Asn Ile Asn Pro Asp Gly Ser Glu Lys Tyr Tyr Val Asp Ser Val
    50                  55                  60

Lys Gly Arg Val Thr Ile Ser Arg Asp Asn Ala Lys Asn Ser Leu Ser
65                  70                  75                  80

Leu Gln Met Asn Ser Leu Arg Val Glu Asp Ala Ala Val Tyr Tyr Cys
                85                  90                  95

Ala Arg Leu Gly Pro Phe His Pro Asp Cys Trp Gly Gln Gly Thr Leu
            100                 105                 110

Val Thr Val Ser Ser
        115

<210> SEQ ID NO 40
<211> LENGTH: 112
<212> TYPE: PRT
<213> ORGANISM: Artificial Sequence
<220> FEATURE:
<223> OTHER INFORMATION: KPB202 VL Amino Acid Sequence

<400> SEQUENCE: 40

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30
```

Asp Gly Asn Thr Tyr Leu Asn Trp Phe Gln Gln Arg Pro Gly Gln Ser
            35                  40                  45

Pro Arg Leu Ile Tyr Glu Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Ile Gly Val Tyr Tyr Cys Met Gln Gly
                85                  90                  95

Thr His Trp Pro Trp Thr Phe Gly Gln Gly Thr Lys Val Glu Ile Lys
            100                 105                 110

<210> SEQ ID NO 41
<211> LENGTH: 5
<212> TYPE: PRT
<213> ORGANISM: Artificial Sequence
<220> FEATURE:
<223> OTHER INFORMATION: 54H7 VH-CDR1

<400> SEQUENCE: 41

Asn Tyr Trp Met Gln
1               5

<210> SEQ ID NO 42
<211> LENGTH: 17
<212> TYPE: PRT
<213> ORGANISM: Artificial Sequence
<220> FEATURE:
<223> OTHER INFORMATION: 54H7 VH-CDR2

<400> SEQUENCE: 42

Asn Ile Tyr Pro Gly Ser Gly Asn Thr Asn Tyr Asp Glu Lys Phe Arg
1               5                   10                  15

Ser

<210> SEQ ID NO 43
<211> LENGTH: 6
<212> TYPE: PRT
<213> ORGANISM: Artificial Sequence
<220> FEATURE:
<223> OTHER INFORMATION: 54H7 VH-CDR3

<400> SEQUENCE: 43

Asn Trp Asn Phe Asp Tyr
1               5

<210> SEQ ID NO 44
<211> LENGTH: 11
<212> TYPE: PRT
<213> ORGANISM: Artificial Sequence
<220> FEATURE:
<223> OTHER INFORMATION: 54H7 VL-CDR1

<400> SEQUENCE: 44

Arg Ala Ser Gln Asp Ile Gly Ser Ser Leu Asn
1               5                   10

<210> SEQ ID NO 45
<211> LENGTH: 7
<212> TYPE: PRT
<213> ORGANISM: Artificial Sequence
<220> FEATURE:
<223> OTHER INFORMATION: 54H7 VL-CDR2

<400> SEQUENCE: 45

Ala Thr Ser Ser Leu Asp Ser
1               5

<210> SEQ ID NO 46
<211> LENGTH: 9
<212> TYPE: PRT
<213> ORGANISM: Artificial Sequence
<220> FEATURE:
<223> OTHER INFORMATION: 54H7 VL-CDR3

<400> SEQUENCE: 46

Leu Gln His Thr Asp Ser Pro Tyr Thr
1               5

<210> SEQ ID NO 47
<211> LENGTH: 115
<212> TYPE: PRT
<213> ORGANISM: Artificial Sequence
<220> FEATURE:
<223> OTHER INFORMATION: 54H7 VH

<400> SEQUENCE: 47

Gln Val His Leu Gln Gln Pro Gly Ser Glu Leu Val Arg Pro Gly Ala
1               5                   10                  15

Ser Val Thr Leu Ser Cys Lys Ala Ser Gly Tyr Thr Phe Thr Asn Tyr
                20                  25                  30

Trp Met Gln Trp Val Lys Gln Arg Pro Gly Gln Gly Leu Glu Trp Ile
            35                  40                  45

Gly Asn Ile Tyr Pro Gly Ser Gly Asn Thr Asn Tyr Asp Glu Lys Phe
        50                  55                  60

Arg Ser Lys Ala Thr Leu Thr Val Asp Thr Ser Ser Ser Thr Ala Tyr
65                  70                  75                  80

Met His Leu Thr Ser Leu Thr Ser Glu Asp Ser Ala Val Tyr Tyr Cys
                85                  90                  95

Thr Arg Asn Trp Asn Phe Asp Tyr Trp Gly Gln Gly Thr Thr Leu Thr
            100                 105                 110

Val Ser Ser
    115

<210> SEQ ID NO 48
<211> LENGTH: 107
<212> TYPE: PRT
<213> ORGANISM: Artificial Sequence
<220> FEATURE:
<223> OTHER INFORMATION: 54H7 VL Amino Acid Sequence

<400> SEQUENCE: 48

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
                20                  25                  30

Leu Asn Trp Leu Gln Gln Glu Pro Asp Gly Thr Ile Lys Arg Leu Ile
            35                  40                  45

Tyr Ala Thr Ser Ser Leu Asp Ser Gly Val Pro Lys Arg Phe Ser Gly
        50                  55                  60

Ser Arg Ser Gly Ser Glu Tyr Ser Leu Thr Ile Ser Ser Leu Glu Ala
65                  70                  75                  80

Glu Asp Phe Val Asp Tyr Tyr Cys Leu Gln His Thr Asp Ser Pro Tyr
                85                  90                  95

Thr Phe Gly Gly Gly Thr Lys Leu Glu Leu Lys
            100                 105

<210> SEQ ID NO 49
<211> LENGTH: 364
<212> TYPE: DNA
<213> ORGANISM: Artificial Sequence
<220> FEATURE:
<223> OTHER INFORMATION: KPA27 VH Polynucleotide Sequence

<400> SEQUENCE: 49
caggtgcagc tggtgcagtc tggggctgag gtgaagaaac ctggggcctc agtgaaggtc      60
tcctgcaagg cttctgaaaa caccttcaac gacttctata tgcactgggt gcgacaggcc     120
cctggacaag gcttgagtg gatgggatgg atccaccctg acggtgttgt cacaaactat     180
gcacagaaat tcagggcag ggtcactatg accaggaca cgtccatcaa cacagtctac      240
atggaattga acggcctgat ctctgacgac acggccgtgt attactgtat gagagacggg     300
ccaggatcag aaggttcctg gtttgactat tggggccagg gaaccctggt caccgtctcc     360
tcag                                                                  364

<210> SEQ ID NO 50
<211> LENGTH: 310
<212> TYPE: DNA
<213> ORGANISM: Artificial Sequence
<220> FEATURE:
<223> OTHER INFORMATION: KPA27 VL Polynucleotide Sequence

<400> SEQUENCE: 50
gacatccaga tgacccagtc tccttccacc ctgtctgcat ctgtaggaga cagagtcacc      60
atcacttgcc gggccagtca gcctgttagt aatagattgg cctggtatca gcagaaacca     120
gggagagccc ctacactcct gatctacaag gcgtctactt tacaaagtgg ggtcccatta     180
aggttcagcg gcagtggatc tgggacagag ttcactctca ccatcagcag cctgcagtct     240
gatgattttg caacttatta ctgccaacag tctcagacct cggccaagg gaccaaggtg     300 gaaatcaaac                                                            310

<210> SEQ ID NO 51
<211> LENGTH: 352
<212> TYPE: DNA
<213> ORGANISM: Artificial Sequence
<220> FEATURE:
<223> OTHER INFORMATION: KPD202 VH Polynucleotide Sequence

<400> SEQUENCE: 51
gaggtgcagc tggtggagtc tgggggaggc ttggtccagc ctggggggtc cctgagcctc      60
tcctgtgcag cctctggatt cacctttagt aacttttggg tggctggggg ccgccaggct     120
ccagggaagg gcctggagtg ggtggccaat ataaacccag atggaagtga gaaatactat     180
gtggactctg tgaagggccg agtcaccatc tccagagaca cgccaagaa ctcactgtct     240 ctgcaaatga acagcctgag agtcgaggac gcggctgtgt actactgtgc gagactaggg     300
ccgttccatc ctgactgctg ggccaggga accctggtca ccgtctcctc ag              352

<210> SEQ ID NO 52
<211> LENGTH: 337
<212> TYPE: DNA
<213> ORGANISM: Artificial Sequence
<220> FEATURE:
<223> OTHER INFORMATION: KPD202  VL Polynucleotide Sequence

<400> SEQUENCE: 52

```
gatgttgtga tgactcagtc tccactctcc ctgcccgtca cccttggaca gccggcctcc    60
atctcctgca ggtctagtca aagcctcgta cacagtgatg aaacaccta cttgaattgg   120
tttcagcaga ggccaggcca atctccaagg cgcctaattt atgaggtttc taaccgggac   180
tctggggtcc cagacagatt cagcggcagt gggtcaggca ctgatttcac actgaaaatc   240
agcagggtgg aggctgagga tattgggggtt tattactgca tgcaaggaac acactggccg   300
tggacgttcg gccaagggac caaggtggaa atcaaac                             337
```

<210> SEQ ID NO 53
<211> LENGTH: 361
<212> TYPE: DNA
<213> ORGANISM: Artificial Sequence
<220> FEATURE:
<223> OTHER INFORMATION: KPJ4 VH Polynucleotide Sequence

<400> SEQUENCE: 53

```
caggtacagc tgcagcagtc aggtccagga ctggtgaggc cctcgcagac cctctcactc    60
acctgtgcca tctccgggga cagtgtctct agcaacactg ctgcttggaa ctggatcagg   120
cagtccccat cgagaggcct tgagtggctg ggaaggacat attacaggtc cgagtggtat   180
aatgattatg cagtatctgt gaaaagtcga ataaccatca cccagacac atccaagaac   240
cagttctccc tgcagttgaa ctctgtgact cccgaggaca cggctgtgta ttactgtgca   300
agaatttcct ggaacgacct cccagcttgg ggccagggaa ccctggtcac cgtctcctca   360
g                                                                    361
```

<210> SEQ ID NO 54
<211> LENGTH: 340
<212> TYPE: DNA
<213> ORGANISM: Artificial Sequence
<220> FEATURE:
<223> OTHER INFORMATION: KPJ4 VL Polynucleotide Sequence

<400> SEQUENCE: 54

```
gacatcgtga tgacccagtc tccagactcc ctggctgtgt ctctgggcga gagggccact    60
atcaactgca gtccagcca gagtatttta tacagctccc acaataagaa ctacttagct   120
tggtaccagc agaaaccagg acagcctcct aaggtgctca tttactgggc gtctacccgg   180
gaatccgggg tccctgaccg attcagtggc agcgggtctg ggacagattt cactctcacc   240
atcagcaacc tgcaggctga agatgtgca gtttattact gtcagcagta ttgtaatatc   300
ccgtacactt ttggccaggg gaccaagctg gagatcaaac                          340
```

<210> SEQ ID NO 55
<211> LENGTH: 369
<212> TYPE: DNA
<213> ORGANISM: Artificial Sequence
<220> FEATURE:
<223> OTHER INFORMATION: KPE33 VH Polynucleotide Sequence

<400> SEQUENCE: 55

```
gaagtgcagc tggtggagtc tgggggggcc ttggtacagc ctggcgggtc cctgagactc    60
tcgtgtgcag tttctggatt catctttgat gattatgcca tccactgggt ccggcagct   120
ccagggaagg gcctggagtg gtctcaggc attgcttgga agagtggtgc cacaaactat   180
gcggactctg tgaagggccg cttcgccatc tctagagaca actccaagaa atctatgtat   240
ctacaaatga acagtctggg aactgaagac acggccttgt attactgtac aagacgacgg   300
```

```
gcgtctgggg atgatacttt ttattacttt gactattggg gtcagggaac cctggtcacc    360
gtctcctca                                                            369
```

<210> SEQ ID NO 56
<211> LENGTH: 321
<212> TYPE: DNA
<213> ORGANISM: Artificial Sequence
<220> FEATURE:
<223> OTHER INFORMATION: KPE33 VL Polynucleotide Sequence

<400> SEQUENCE: 56

```
gaaattgtgt tgacacagtc tccagccacc ctgtctttgt ctccaggaga aagagccacc     60
ctctcctgca gggccagtca gaatgttaat accaacttag cctggtacca gcagcgacct    120
ggacagtctc ccagactcct catttatgat gcatccacca gggccgctgg cctcccagcc    180
aggttcagtg gcagtgggtc tgggacagac ttcactctca ccatcagcag cctagagcct    240
gaagattttg cagtctacta ttgtcagcag tgtaccaact ggcggtacac ttttggccag    300
gggaccaagc tggagatcaa a                                              321
```

<210> SEQ ID NO 57
<211> LENGTH: 369
<212> TYPE: DNA
<213> ORGANISM: Artificial Sequence
<220> FEATURE:
<223> OTHER INFORMATION: KPE33V2016 VH Polynucleotide Sequence

<400> SEQUENCE: 57

```
gaggtgcagc tggtcgaatc cggcggggga ctggtgcagc ctggccgctc actgagactg     60
agctgcgccg cttccgggtt catctttgac gattacgcta tgcactgggt gcggcaggca    120
cctggcaagg gactggagtg ggtctctggg atcgcctgga aaagtggagc aaccaactac    180
gccgactcag tgaaggggag attcgccatt agccgggata actctaagaa agtatgtat    240 ctgcagatga attccctggg aaccgaagac acagccctgt actattgtac acggagaagg    300
gcttctggcg acgatacttt ctactatttt gattattggg gacagggcac tctggtgacc    360
gtcagctcc                                                            369
```

<210> SEQ ID NO 58
<211> LENGTH: 321
<212> TYPE: DNA
<213> ORGANISM: Artificial Sequence
<220> FEATURE:
<223> OTHER INFORMATION: KPE33V2016 VL Polynucleotide Sequence

<400> SEQUENCE: 58

```
gagatcgtgc tgacacagtc cccagccact ctgtctctga gtcccgggga acgggcaact     60
ctgtcttgca gagccagtca gaacgtcaat accaacctgg cttggtacca gcagaagccc    120
ggacaggcac ctcgactgct gatctatgac gccagcaata gggctacagg cattccagca    180
cgcttctcag gatctggatc tggaaccgac tttactctga ccatcagctc cctggagccc    240
gaagatttcg ccgtgtacta ttgtcagcag accacaaact ggagatacac ctttggccag    300
gggacaaagc tggagatcaa g                                              321
```

<210> SEQ ID NO 59
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 59

Ile Ala Tyr Lys Ser Gly Ala Thr
1               5

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Arg Arg Arg Ala Ser Gly Asp Asn Thr Phe Tyr Tyr Phe Asp Tyr
1               5                   10                  15

<210> SEQ ID NO 61
<211> LENGTH: 123
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Ile Phe Asp Asp Tyr
            20                  25                  30

Ala Ile His Trp Val Arg Gln Ala Pro Gly Lys Gly Leu Glu Trp Val
        35                  40                  45

Ser Gly Ile Ala Tyr Lys Ser Gly Ala Thr Asn Tyr Ala Glu Ser Val
    50                  55                  60

Lys Gly Arg Phe Thr Ile Ser Arg Asp Gln Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Arg Arg Arg Ala Ser Gly Asp Asn Thr Phe Tyr Tyr Phe Asp Tyr
            100                 105                 110

Trp Gly Gln Gly Thr Leu Val Thr Val Ser Ser
        115                 120

<210> SEQ ID NO 62
<211> LENGTH: 123
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Ile Phe Asp Asp Tyr
            20                  25                  30

Ala Ile His Trp Val Arg Gln Ala Pro Gly Lys Gly Leu Glu Trp Val
        35                  40                  45

Ser Gly Ile Ala Tyr Lys Ser Gly Ala Thr Asn Tyr Ala Glu Ser Val
    50                  55                  60
```

Lys Gly Arg Phe Thr Ile Ser Arg Asp Gln Ser Lys Ser Leu Tyr
65                  70                  75                  80

Leu Gln Met Asn Ser Leu Arg Ala Glu Asp Thr Ala Leu Tyr Tyr Cys
                85                  90                  95

Thr Arg Arg Ala Ser Gly Asp Asn Thr Phe Tyr Tyr Phe Asp Tyr
            100                 105                 110

Trp Gly Gln Gly Thr Leu Val Thr Val Ser Ser
        115                 120

<210> SEQ ID NO 63
<211> LENGTH: 107
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Val Asn Thr Asn
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Thr Thr Asn Trp Arg Tyr
                85                  90                  95

Thr Phe Gly Gln Gly Thr Lys Leu Glu Ile Lys
            100                 105

<210> SEQ ID NO 64
<211> LENGTH: 369
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 64
caggtgcagc tcgtggagtc cggcggtggc ctggttcagc ctggccgctc tcttagactg      60
agttgcgccg ctagcggttt tatttttcgac gactatgcga tccactgggt tagacaagca     120
ccaggaaagg gacttgaatg ggtttctggg attgcgtata atcaggggc cacgaactac       180 gctgagagcg ttaaggggcg atttactata agcagggatc agtccaaaaa ctcactgtac     240
ttgcagatga actcactcag agccgaggac acggcgttgt actactgcac acgaaggagg     300
gcatcaggag ataatacctt ttattacttc gactactggg gccaaggcac gttggtaacg     360
gtgagttct                                                              369

<210> SEQ ID NO 65
<211> LENGTH: 369
<212> TYPE: DNA
<213> ORGANISM: Artificial Sequence
<220> FEATURE:
<223> OTHER INFORMATION: Description of Artificial Sequence: Synthetic
      peptide

<400> SEQUENCE: 65

```
caggtgcagc tcgtggagtc cggcggtggc ctggttcagc ctggccgctc tcttagactg      60
agttgcgccg ctagcggttt tattttcgac gactatgcga tccactgggt tagacaagca     120
ccaggaaagg gacttgaatg ggtttctggg attgcgtata aatcagggc cacgaactac     180 gctgagagcg ttaaggggcg atttactata agcagggatc agtccaaaaa gtcactgtac     240
ttgcagatga actcactcag agccgaggac acggcgttgt actactgcac acgaaggagg     300
gcatcaggag ataataccct ttattacttc gactactggg gccaaggcac gttggtaacg     360
gtgagttct                                                              369
```

<210> SEQ ID NO 66
<211> LENGTH: 321
<212> TYPE: DNA
<213> ORGANISM: Artificial Sequence
<220> FEATURE:
<223> OTHER INFORMATION: Description of Artificial Sequence: Synthetic peptide

<400> SEQUENCE: 66

```
cagattgtgt tgacgcagag tcccgcgaca cttagcctct ctcccggaga gagagcgacg      60
cttagttgcc gagcatccca gaacgtcaac actaatctcg cgtggtatca gcagaagccg     120
ggccaagccc ccaggctgtt gatttacgac gctagtaacc gcgccacagg aatcccggca     180
agatttagtg ggtcaggatc aggaactgac tttaccttga cgataagtag tctggaacca     240
gaagatttcg ccgtatatta ctgtcaacag acaacaaact ggcgctacac cttcggccaa     300
ggaacaaaac ttgagatcaa g                                               321
```

<210> SEQ ID NO 67
<211> LENGTH: 321
<212> TYPE: DNA
<213> ORGANISM: Artificial Sequence
<220> FEATURE:
<223> OTHER INFORMATION: Description of Artificial Sequence: Synthetic peptide

<400> SEQUENCE: 67

```
cagattgtgt tgacgcagag tcccgcgaca cttagcctct ctcccggaga gagagcgacg      60
cttagttgcc gagcatccca gaacgtcaac actaatctcg cgtggtatca gcagaagccg     120
ggccaagccc ccaggctgtt gatttacgac gctagtaacc gcgccacagg aatcccggca     180
agatttagtg ggtcaggatc aggaactgac tttaccttga cgataagtag tctggaacca     240
gaagatttcg ccgtatatta ctgtcaacag acaacaaact ggcgctacac cttcggccaa     300
ggaacaaaac ttgagatcaa g                                               321
```

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 68

```
Cys Ser Trp His Leu Cys
1               5
```

ANTI-O1 ANTIBODIES AND USES THEREOF

REFERENCE TO SEQUENCE LISTING SUBMITTED ELECTRONICALLY

The content of the electronically submitted sequence listing in ASCII text file 2943_1420001_Seqlisting_ST25 (Size: 33,059 bytes; and Date of Creation: Jan. 2, 2020) is incorporated herein by reference in its entirety.

BACKGROUND OF THE INVENTION

Field of the Invention

The field of the invention generally relates to antigen binding proteins (e.g., antibodies and antigen-binding fragments thereof) that specifically bind to *Klebsiella pneumoniae* O1 antigen and the use of those binding proteins for prevention or treatment of *Klebsiella* infections.

Background of the Invention

*Klebsiella* is a Gram negative bacterium that is rapidly gaining clinical importance as a causative agent for opportunistic and nosocomial infection, including pneumonia, urinary tract infection, neonatal septicemia, and surgery wound infection. In addition, there are emerging syndromes associated with *Klebsiella* infections such as pyogenic liver abscesses (PLA), endophthalmitis, meningitis, and necrotizing meningitis. The clinical impact of *Klebsiella* infections is discussed, for example, in Podschun R. and Ullman U. *Clin. Microbiol Rev.* 11:589-603 (1998).

Antibiotic resistance has emerged as one of the major challenges in the fight against bacterial infection. See e.g. Iredell J., et al., *BMJ* 351:h6420 (2015). While some progress has been made against drug resistant *Staphylococcus aureus*, Gram negative opportunistic infections are most problematic. Among these, *Klebsiella pneumoniae* has become particularly challenging with multi-drug resistant strains widely circulating. Infections such as Extended-Spectrum Beta Lactamase (ESBL) and carbapenem resistant enterobacteriaceae (CRE) carbapenamase, including *Klebsiella pneumoniae* carbapenamase (KPC) and New Delhi metallo-beta-lactamase 1 (NDM-1), have spread worldwide and rendered current antibiotic classes largely inadequate. This reality coupled with the dwindling antibiotics pipeline leaves few therapeutic alternatives. Several recent high profile outbreaks underscore the urgency associated with *K. pneumoniae* antibiotic resistance. It is therefore critical to develop strategies to complement antibiotics therapies.

Multiple virulence factors have been implicated in *K. pneumoniae* pathogenesis, including capsular polysaccharides (CPS) and lipopolysaccharides (LPS). Polyclonal antibodies directed against LPS and CPS are protective in preclinical models of lethal *K. pneumoniae* infections. However targeting these two antigens with antibodies poses a significant challenge with respect to strain coverage. There are more than seventy-seven known capsule serotypes and eight O-antigen serotypes, and it is not clear which are the most prevalent or associated with pathogenesis. In addition, the limited number of monoclonal antibodies targeting conserved epitopes within LPS have no reported protective effect (Brade et al. 2001, J Endotoxin Res, 7(2): 119-24).

Thus, there is a great need to identify and develop antibodies that have protective effect against *Klebsiella* (e.g., *K. pneumoniae*), especially antibiotic resistant *Klebsiella*, infections.

BRIEF SUMMARY OF THE INVENTION

The present disclosure provides *K. pneumoniae* O1 binding proteins, e.g., antibodies or antigen binding fragments thereof, and methods of treating *Klebsiella* infections using *K. pneumoniae* O1 binding proteins.

In one instance, provided herein is an isolated antigen binding protein that specifically binds to *Klebsiella pneumoniae* O1 antigen, wherein the antigen binding protein: a) induces opsonophagocytic killing (OPK) of *Klebsiella*, b) kills *Klebsiella* via complement dependent killing as measured by a serum bactericidal assay or c) induces OPK of *Klebsiella* and kills *Klebsiella* via complement dependent killing as measured by a serum bactericidal assay.

In one instance, the antigen binding protein (i) induces OPK of *Klebsiella*, kills *Klebsiella* via complement dependent killing as measured by a serum bactericidal assay, and neutralizes lipopolysaccharide (LPS) or (ii) induces OPK of *Klebsiella* and kills *Klebsiella* via complement dependent killing as measured by a serum bactericidal assay but does not neutralize LPS. In some embodiments, the *Klebsiella* is *K. pneumoniae, K. oxytoca, K. granulomatis, K. ozaenae, K. rhinoscleromatis* or *K. planticola*. In one instance, the *Klebsiella* is multi-drug resistant including a strain listed in one of rows 1-134 of Table 8.

In one instance, the antigen binding protein: a) induces opsonophagocytic killing (OPK) of *Klebsiella pneumoniae* (*K. pneumoniae*), b) kills *K. pneumoniae* via complement dependent killing as measured by a serum bactericidal assay, and/or c) neutralizes lipopolysaccharide (LPS).

In one instance, the antigen binding protein renders a multi-drug resistant *K. pneumoniae* strain sensitive to at least one antibiotic.

In one instance, the antigen binding protein binds to the D-Galactan II domain of *K. pneumoniae* O1 antigen.

The present disclosure also provides an isolated antigen binding protein that specifically binds to *Klebsiella pneumoniae* O1 antigen comprising a set of Complementarity-Determining Regions (CDRs): HCDR1, HDR2, HCDR3, LCDR1, LCDR2, and LCDR3 wherein: HCDR1 has the amino acid sequence of SEQ. ID. NO:1; HCDR2 has the amino acid sequence of SEQ. ID. NO: 2; HCDR3 has the amino acid sequence of SEQ. ID. NO: 3; LCDR1 has the amino acid sequence of SEQ. ID. NO: 4; LCDR2 has the amino acid sequence of SEQ. ID. NO: 5 or 10; and LCDR3 has the amino acid sequence of SEQ. ID. NO: 11.

In one instance, provided herein is an isolated antigen binding protein that specifically binds *Klebsiella pneumoniae* O1 antigen, wherein the antigen binding protein comprises a heavy chain variable region (VH) at least 95%, 96%, 97%, 98% or 99% identical to SEQ ID NO:12 and/or a light chain variable region (VL) at least 95%, 96%, 97%, 98% or 99% identical to SEQ ID NO:13. In one instance, the antigen binding protein that specifically binds *Klebsiella pneumoniae* O1 antigen comprises a VH comprising SEQ ID NO:12 and/or a VL comprising SEQ ID NO:13.

The present disclosure also provides an isolated antigen binding protein that specifically binds to the same epitope in the *Klebsiella pneumoniae* O1 antigen as an antibody comprising a VH comprising SEQ ID NO:12 and a VL comprising SEQ ID NO:13.

In one instance, provided herein is an isolated antigen binding protein that competitively inhibits the binding to *Klebsiella pneumoniae* O1 antigen of an antibody comprising a VH comprising SEQ ID NO:12 and a VL comprising SEQ ID NO:13.

The present disclosure also provides an isolated antigen binding protein that specifically binds to *Klebsiella pneumoniae* O1 antigen comprising a set of Complementarity-Determining Regions (CDRs): HCDR1, HCDR2, HCDR3, LCDR1, LCDR2, and LCDR3, wherein the HCDR1, HCDR2, HCDR3, LCDR1, LCDR2, and LCDR3 comprise the amino acid sequences of: SEQ. ID. NOs: 41, 42, 43, 44, 45, and 46, respectively; SEQ. ID. NOs: 32, 33, 34, 35, 36, and 38, respectively; SEQ. ID. NOs: 32, 33, 34, 35, 37, and 38, respectively; SEQ. ID. NOs: 1, 2, 3, 4, 5, and 7, respectively; SEQ. ID. NOs: 1, 2, 3, 4, 6, and 7, respectively; SEQ. ID. NOs: 14, 15, 16, 17, 18, and 20, respectively; SEQ. ID. NOs: 14, 15, 16, 17, 19, and 20, respectively; SEQ. ID. NOs: 23, 24, 25, 26, 27, and 29, respectively; or SEQ. ID. NOs: 23, 24, 25, 26, 28, and 29, respectively.

In one instance, provided herein is an isolated antigen binding protein that specifically binds to *Klebsiella pneumoniae* O1 antigen comprising a VH comprising SEQ ID NO:47, SEQ ID NO:39, SEQ ID NO: 8, SEQ ID NO:21, or SEQ ID NO:30, and/or a VL comprising SEQ ID NO:48, SEQ ID NO:40, SEQ ID NO:9, SEQ ID NO:22, or SEQ ID NO:31.

In one instance, provided herein is an isolated antigen binding protein that specifically binds to the same epitope in the *Klebsiella pneumoniae* O1 antigen as an antibody comprising a VH and a VL comprising: SEQ. ID. NO: 47 and SEQ ID NO:48, respectively; SEQ. ID. NO: 39 and SEQ ID NO:40, respectively; SEQ. ID. NO: 8 and SEQ ID NO:9, respectively; SEQ. ID. NO:21 and SEQ ID NO:22, respectively; or SEQ. ID. NO:30 and SEQ ID NO:31, respectively.

In one instance, provided herein is an isolated antigen binding protein that competitively inhibits the binding to *Klebsiella pneumoniae* O1 antigen of an antibody comprising a VH and a VL comprising: SEQ. ID. NO: 47 and SEQ ID NO:48, respectively; SEQ. ID. NO: 39 and SEQ ID NO:40, respectively; SEQ. ID. NO: 8 and SEQ ID NO:9, respectively; SEQ. ID. NO: 21 and SEQ ID NO:22, respectively; or SEQ. ID. NO: 30 and SEQ ID NO:31, respectively.

In one instance, the antigen binding protein is an antibody. In one instance, the antigen binding protein is an antigen binding fragment of an antibody. In one instance, the antigen binding protein is a monoclonal antibody, a recombinant antibody, a human antibody, a humanized antibody, a chimeric antibody, a bi-specific antibody, a multi-specific antibody, or an antigen binding fragment thereof. In one instance, the antigen binding protein comprises a Fab, Fab', F(ab')2, Fd, single chain Fv or scFv, disulfide linked Fv, V-NAR domain, IgNar, intrabody, IgGΔCH2, minibody, F(ab')3, tetrabody, triabody, diabody, single-domain antibody, DVD-Ig, Fcab, mAb2, (scFv)2, or scFv-Fc.

The present disclosure also provides an isolated nucleic acid molecule encoding an antigen binding protein, including an antibody or antigen binding fragment thereof, disclosed herein. In one instance, the nucleic acid molecule is operably linked to a control sequence. In one instance, provided herein is a vector comprising a nucleic acid molecule provided herein.

The present disclosure also provides a host cell transformed with a nucleic acid molecule provided herein or a vector provided herein. In one instance, the host cell is a mammalian host cell, including, e.g., a HEK293 cell, an NSO murine myeloma cell, a PER.C6® human cell, or a Chinese hamster ovary (CHO) cell.

The present disclosure also provides a method of making an antigen binding protein, including an antibody or antigen binding fragment thereof, provided herein comprising (a) culturing a host cell expressing the antigen binding protein or culturing a host cell provided herein or a hybridoma provided herein; and (b) isolating the antigen binding protein thereof from the cultured host cell. In one instance, provided herein is an antigen binding protein produced using the method provided herein.

The present disclosure also provides a pharmaceutical composition comprising an antigen binding protein, including an antibody or antigen binding fragment thereof, provided herein and a pharmaceutically acceptable excipient. In one instance, the pharmaceutically acceptable excipient is a preservative, stabilizer, or antioxidant. In one instance, the pharmaceutical composition is for use as a medicament.

The present disclosure also provides the use of an antigen binding protein (including an antibody or antigen binding fragment thereof) or a pharmaceutical composition provided herein for treating a condition associated with a *Klebsiella* infection. In one instance, provided herein is a method for treating, preventing, or ameliorating a condition associated with a *Klebsiella* infection in a subject in need thereof comprising administering to the subject an effective amount of an antigen binding protein (including an antibody or antigen binding fragment thereof) provided herein or a pharmaceutical composition provided herein. In one instance, the method for treating a condition associated with a *Klebsiella* infection in a subject in need thereof comprises administering an effective amount of antigen binding protein including an antibody or antigen binding fragment thereof) that specifically binds to *Klebsiella pneumoniae* O1 antigen. In one instance, the antigen binding protein that specifically binds to *Klebsiella pneumoniae* O1 antigen is an antibody or antigen binding fragment thereof. In one instance, the antigen binding protein that specifically binds to *Klebsiella pneumoniae* O1 antigen is an antigen binding protein provided herein or a pharmaceutical composition provided herein. In one instance, the *Klebsiella* is *K. pneumoniae, K. oxytoca, K. planticola, K. ozaenae, K. rhinosclermoatis* and/or *K. granulomatis*.

In one instance, provided herein is a method for inhibiting the growth of *Klebsiella* or reducing the number of *Klebsiella* in a subject infected with *Klebsiella* (including antibiotic-resistant *Klebsiella*) comprising administering to a subject in need thereof an antigen binding protein provided herein or a pharmaceutical composition provided herein. In one instance, the antigen binding protein that specifically binds to *Klebsiella pneumoniae* O1 antigen is an antibody or antigen binding fragment thereof. In one instance, the antigen binding protein that specifically binds to *Klebsiella pneumoniae* O1 antigen is an antigen binding protein provided herein or a pharmaceutical composition provided herein. In one instance, the *Klebsiella* is *K. pneumoniae, K. oxytoca, K. planticola, K. ozaenae, K. rhinosclermoatis* and/or *K. granulomatis*.

The present disclosure also provides a method for treating, preventing, or ameliorating a condition associated with a *Klebsiella pneumoniae* and *Staphylococcus aureus* co-infection in a subject in need thereof comprising administering to said subject an effective amount of an antigen binding protein that specifically binds to *Klebsiella pneumoniae* O1 antigen, including an antigen binding protein (including an antibody or antigen binding fragment thereof) provided herein or a pharmaceutical composition provided herein.

In one instance, provided herein is a method of inhibiting, reducing, or eliminating the virulence of *Klebsiella pneumoniae* in a subject co-infected with *Klebsiella pneumoniae* and *Staphylococcus aureus*, or a method of increasing survival of a subject infected with both *Klebsiella pneumo-* niae and *Staphylococcus aureus* comprising administering to the subject an effective amount of an antigen binding protein that specifically binds to *Klebsiella pneumoniae* O1 antigen.

The present disclosure also provides a method for sensitizing an antibiotic-resistant *Klebsiella* strain to antibiotics comprising contacting the antibody-resistant *Klebsiella* strain with an antigen binding protein (including an antibody or antigen binding fragment thereof) that specifically binds to *Klebsiella pneumoniae* O1 antigen. In one instance, the method further comprises administering an antibiotic. In one instance, the antigen binding protein and the antibiotic provide a synergistic therapeutic effect.

BRIEF DESCRIPTION OF THE DRAWINGS/FIGURES

FIGS. 1A-C show the activities of anti-*K. pneumoniae* O1 antigen antibodies. FIG. 1A shows the ability of the antibodies to bind to purified O1 LPS by enzyme-linked immunosorbent assay (ELISA). FIG. 1B shows the activity of the antibodies to mediate complement-dependent killing as shown using a serum bactericidal assay (SBA). FIG. 1C shows the ability of the antibodies to induce opsonophagocytic killing (OPK). Class I antibodies (e.g., 54H7 and KPB202) and Class II antibodies (e.g., KPA27, KPE33, and KPJ4) both induce OPK of *K. pneumoniae* and kill *K. pneumoniae* as measured in the SBA assay. However, Class I antibodies also neutralize LPS, whereas Class II antibodies do not.

FIG. 2 shows that the anti-O1-LPS antibodies reduce bacterial lung burden in an intranasal lung infection model against *K. pneumoniae* strain Kp8045 (O1:K1). KPE33 at 15 mg/kg significantly reduced bacterial lung burden, and other anti-O1 antibodies at 15 mg/kg also reduced organ burden, of about 2-3 log when administered 48 hour post infection. An irrelevant human IgG1 antibody (IgG Control) was used as control.

FIGS. 3A-C show that anti-O1 antigen antibody KPE33 protects mice from lethal bacterial challenge when administered 1 hour post bacterial infection. FIG. 3A shows that KPE33 dose dependently enhanced survival in a lethal bacterial pneumonia model with a multi-drug resistant *K. pneumoniae* carbapenem-resistant (CRE) strain Kp1131115 (O1) compared with human IgG1 control antibody (R347). FIG. 3B shows that KPE33 significantly enhanced survival in a lethal bacteremia model with an extended spectrum beta-lactamase (ESBL) strain Kp8561 (O1) compared with human IgG1 control antibody (R347). FIG. 3C shows that KPE33-H32+L2016(E1Q) ("KPE33-H32") and KPE33-H32+L2016(E1Q) ("KPE33-H33") dose dependently enhanced survival in a lethal bacterial pneumonia model with a multi-drug resistant *K. pneumoniae* carbapenem-resistant (CRE) strain Kp1131115 (O1) compared with human IgG1 control antibody (R347).

FIGS. 4A-B shows that KPE33 acts synergistically with the antibiotic meropenem in both pneumonia (FIG. 4A) and bacteremia (FIG. 4B) models. Both antibiotic and antibody were administered after infection with *pneumoniae* O1 strains Kp8045 (FIG. 4A) or Kp8561 (FIG. 4B). The combination of meropenem and KPE33 showed significantly better protection in both pneumonia and bacteremia models than monotherapy of either meropenem or KPE33, or the combination of human IgG1 control antibody (R347) and meropenem.

FIG. 5 shows the sequence optimization of KPE33 to generate KPE33v2016. The graph show the binding of KPE33-rIgG1 (left) and KPE33v2016 (right) to O1 LPS, as measured by the Octet platform. Both KPE33 and KPE33v2016 showed a comparable affinity constant ($K_D$) at the average of 5.83E-09 and 4.13E-09, respectively. The bottom panel shows the amino acid sequences for KPE33 variable heavy chain (VH) and variable light chain (VL) and the amino acid sequences for the optimized KPE33v2016 VH and VL. Figure discloses SEQ ID NOS 8, 12, 9 and 13, respectively, in order of appearance.

FIG. 6 shows that sequence optimized KPE33 (KPE33-V-2016) maintained protective activity in a lethal pneumonia model. KPE33 or KPE33-V-2016 were administered at 6 mg/kg 1 hour post bacterial infection with a *K. pneumoniae* carbapenem resistant (KPC) strain. Both antibodies showed a similar level of protection when compared with a human IgG1 control antibody. An IgG2 subclass of KPE33 was also compared in this model, and it showed slightly lower activity than KPE33-IgG1.

FIGS. 7A-D show that KPE33 protects in a *K. pneumoniae* and *S. aureus* co-infection model. FIG. 7A shows that co-infection with sub-lethal inoculums of *K. pneumoniae* and *S. aureus* caused lethal pneumonia. *K. pneumoniae* bacterial burdens were significantly increased in the lungs (FIG. 7B) and spleens (FIG. 7C) of mice co-infected with *K. pneumoniae* and *S. aureus* as compared to mice infected with *K. pneumoniae* alone. FIG. 7D shows that a single treatment with KPE33 (0.5 mL, ip) 24 hours prior to co-infection rescued mice from the lethal co-infection.

FIG. 8 shows that anti-O1 antigen antibody 54H7 reduces serum cytokines after LPS challenge. 54H7 and an IgG1 control antibody were given to mice 3 hours prior to LPS challenge. The animals were then bled and cytokines in the serum were measured 3 hours later. 54H7 reduced serum IL-6, chemokine CXCL-1, and TNF-alpha in two O1 LPS challenge models (Kp43816 LPS and Kp15380 LPS). Polymyxin B (PMB) was used as a positive control.

FIG. 9 shows that 54H7 protects mice in an endotoxemia LPS-induced sepsis model. 54H7 and a control antibody were given to mice 24 hours prior to challenge with LPS. 54H7 provided significant protection at concentrations as low as 1 mg/kg as compared to a control IgG antibody (R347).

FIGS. 10A-B show the effect of 54H7 in a bacterial challenge model in mice. FIG. 10A demonstrates that 15 mg/kg 54H7 protects the mice from lethal pneumonia, and FIG. 10B demonstrates that 54H7 shows synergy with the antibiotic meropenem in this model.

Figure 13:
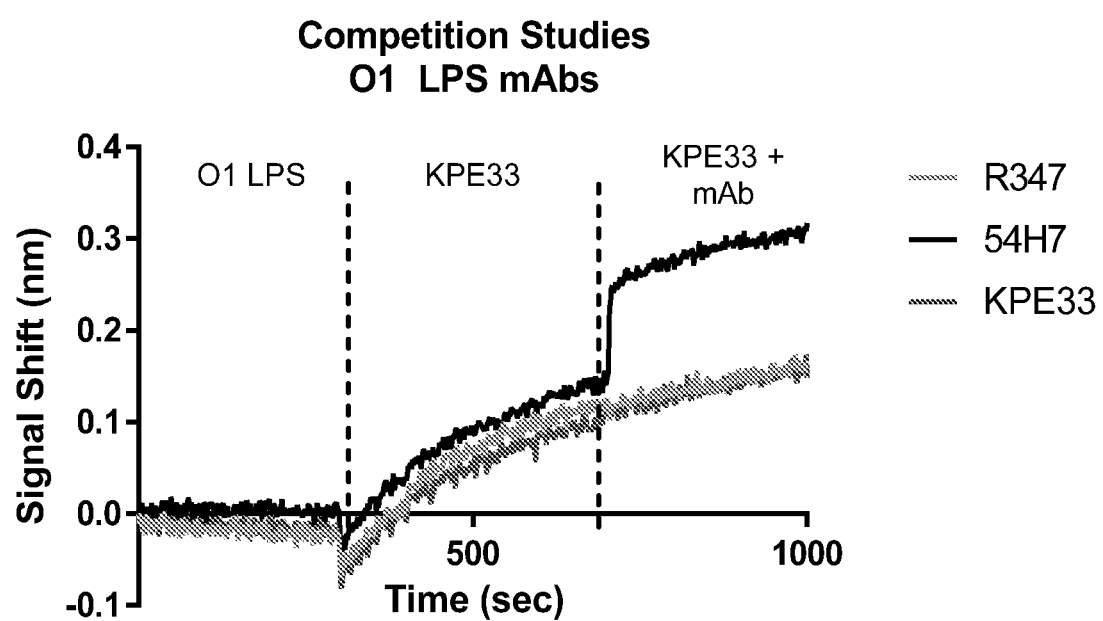

FIG. 13 shows that KPE33 and 54H7 do not compete for binding to the same epitope on O1 LPS. Competitive binding was measured by Fortebio Octet using a capture probe pre-loaded with purified O1 LPS. After initial binding with 10 µg/mL KPE33, the probe was incubated with antibody mixtures containing 10 µg/mL KPE33 with equal concentrations of 54H7 (black line), KPE33 (dark gray line) or the control antibody R347 (light gray line).

FIGS. 14A-D show that γδ T cell recruitment and IL-17 signaling correlate with anti-O1 antibody protection. FIG.

Figure 14A:
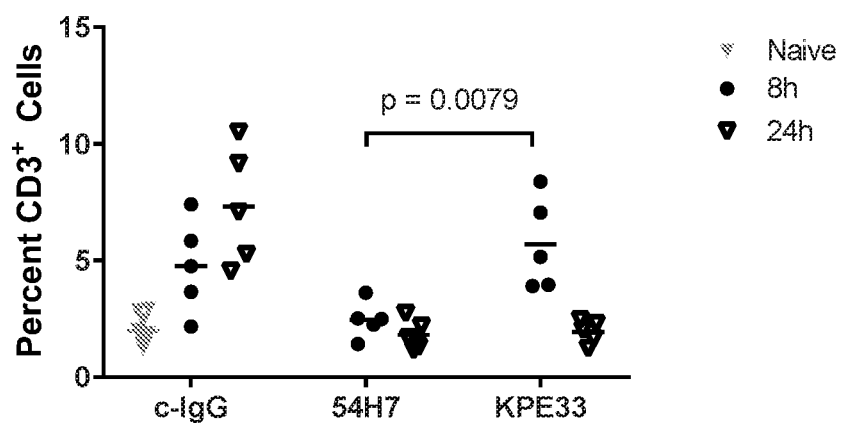
Figure 14B:
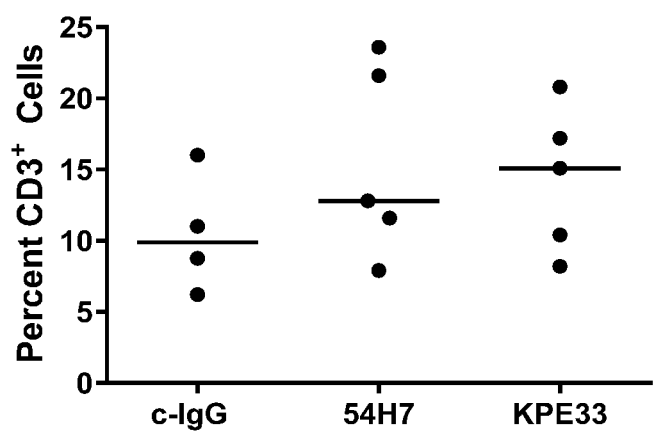
Figure 14C:
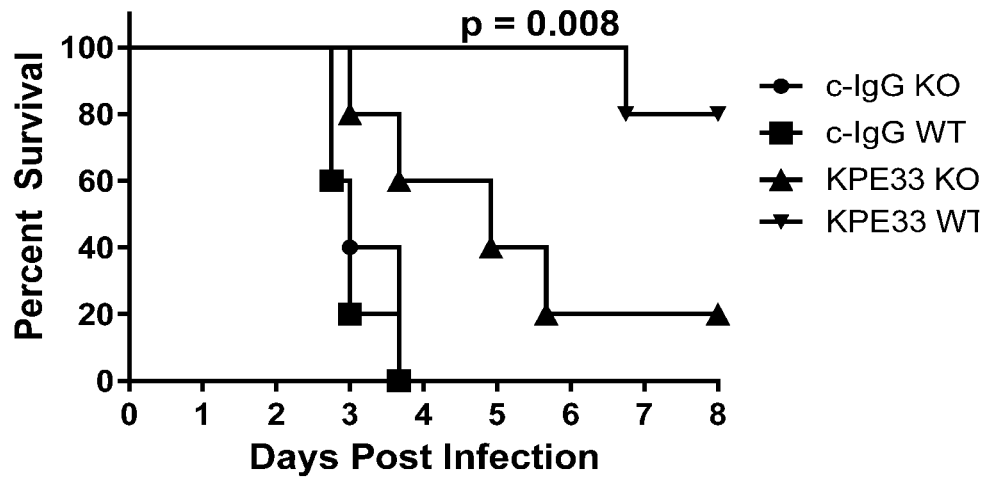
Figure 14D:
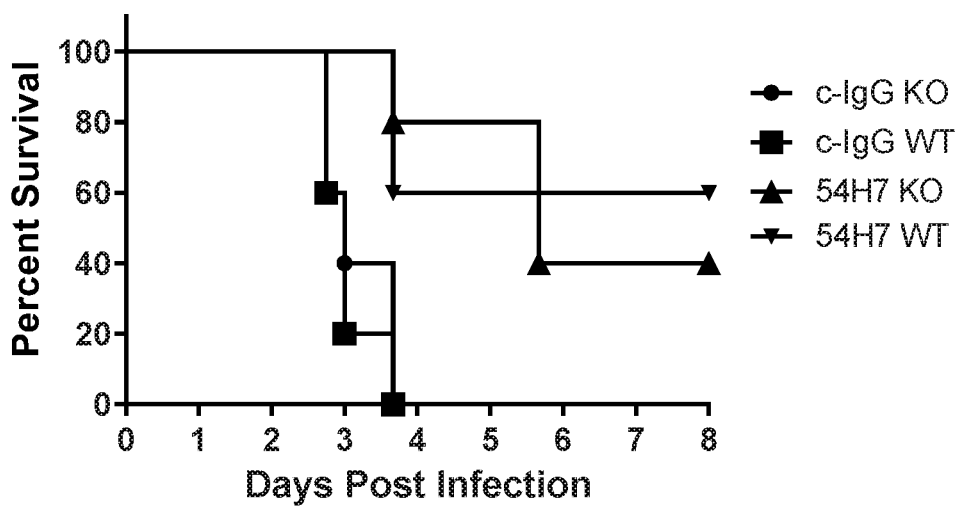

14A shows a flow cytometry analysis of the percent of γδTCR⁺ T cells in the lungs of mice prophylactically treated with anti-LPS monoclonal antibodies and infected with *K. pneumoniae* (1e4 CFU Kp8045). FIG. 14B shows a flow cytometry analysis of the percent of γδTCR⁺ T cells in the lungs of mice treated (1 hour post infection) with anti-LPS monoclonal antibodies and infected for 8 hours with *K. pneumoniae* (1e4 CFU Kp8045). FIG. 14C shows the survival of C57BL/6 (wild type) and il17a (IL-17 knockout) mice prophylactically immunized with c-IgG or KPE33 and infected 24 hours later with *K. pneumoniae* (1e4 CFU Kp8045) (p value indicates significance between KPE33 wild type (WT) mice and KPE33 knockout (KO) mice; N=5 per group). FIG. 14D shows the survival of C57BL/6 (wild type) and il17a (IL-17 knockout) mice prophylactically immunized with c-IgG or 54H7 and infected 24 hours later with *K. pneumoniae* (1e4 CFU Kp8045) (N=5 per group). Statistical significance was determined by ANOVA followed by Dunn's test (FIG. 14A) or log rank test (FIG. 14C). Data are representative of at least 2 independent experiments.

DETAILED DESCRIPTION OF THE INVENTION

The present disclosure provides isolated binding proteins, including antibodies or antigen binding fragments thereof, that bind to *Klebsiella pneumoniae* O1 antigen. Related polynucleotides, vectors, host cells, and pharmaceutical compositions comprising the *Klebsiella pneumoniae* O1 binding proteins, including antibodies or antigen binding fragments thereof, are also provided. Also provided are methods of making and using the O1 binding proteins, including antibodies or antigen binding fragments, disclosed herein. The present disclosure also provides methods of preventing and/or treating a condition associated with a *Klebsiella* infection (e.g., *K. pneumoniae* such as O1 serotype *K. pneumoniae*) by administering the O1 binding proteins, including antibodies or antigen binding fragments, disclosed herein.

In order that the present disclosure can be more readily understood, certain terms are first defined. Additional definitions are set forth throughout the detailed description.

I. Definitions

The terms "a," "an," and "the" include plural referents unless the context clearly dictates otherwise. For example, "an antigen binding protein" is understood to represent one or more antigen binding proteins. The terms "a" (or "an"), as well as the terms "one or more," and "at least one" can be used interchangeably herein. Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "comprise" is generally used in the sense of include, that is to say permitting the presence of one or more features or components. Wherever aspects are described herein with the language "comprising," otherwise analogous aspects described in terms of "consisting of," and/or "consisting essentially of" are also provided.

The term "about" as used in connection with a numerical value throughout the specification and the claims denotes an interval of accuracy, familiar and acceptable to a person skilled in the art. In general, such interval of accuracy is ±10%.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

The term "antigen binding protein" refers to a molecule comprised of one or more polypeptides that recognizes and specifically binds to a target, e.g., *K. pneumoniae* O1 antigen, such as an anti-O1 antibody or antigen-binding fragment thereof.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, multispecific antibodies such as bispecific antibodies generated from at least two intact antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" or "antibody fragment thereof" refers to a portion of an intact antibody. An "antigen-binding fragment" or "antigen-binding fragment thereof" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, scFvs, and single chain antibodies.

It is possible to take monoclonal and other antibodies or fragments thereof and use techniques of recombinant DNA technology to produce other antibodies or chimeric molecules or fragments thereof that retain the specificity of the original antibody or fragment. Such techniques can involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A, or EP-A-239400, and a large body of subsequent literature. A hybridoma or other cell producing an antibody can be subject to genetic mutation or other changes, which may or may not alter the binding specificity of antibodies or fragments thereof produced.

Further techniques available in the art of antibody engineering have made it possible to isolate human and humanized antibodies or fragments thereof. For example, human hybridomas can be made as described by Kontermann and Sefan. Antibody Engineering, Springer Laboratory Manuals (2001). Phage display, another established technique for generating antigen binding proteins has been described in detail in many publications such as Kontermann and Sefan. Antibody Engineering, Springer Laboratory Manuals (2001) and WO92/01047. Transgenic mice in which the mouse antibody genes are inactivated and functionally replaced with human antibody genes while leaving intact other components of the mouse immune system, can be used for isolating human antibodies to human antigens.

Synthetic antibodies or fragments thereof can be created by expression from genes generated by means of oligonucleotides synthesized and assembled within suitable expression vectors, for example as described by Knappik et al. J. Mol. Biol. (2000) 296, 57-86 or Krebs et al. Journal of Immunological Methods 254 2001 67-84.

It has been shown that fragments of a whole antibody can perform the function of binding antigens. Examples of binding fragments are (i) the Fab fragment consisting of VL, VH, CL, and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989), McCafferty et al (1990) Nature, 348, 552-554) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies," multivalent or multispecific fragments constructed by gene fusion (WO94/13804; P. Holliger et al, Proc. Natl. Acad. Sci. USA 90 6444-6448, 1993). Fv, scFv or diabody molecules may be stabilized by the incorporation of disulphide bridges linking the VH and VL domains (Y. Reiter et al, Nature Biotech, 14, 1239-1245, 1996). Minibodies comprising a scFv joined to a CH3 domain may also be made (S. Hu et al, Cancer Res., 56, 3055-3061, 1996).

Where bispecific antibodies are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction. Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against O1, then a library can be made where the other arm is varied and an antibody of appropriate specificity selected. Bispecific whole antibodies may be made by knobs-into-holes engineering (J. B. B. Ridgeway et al, Protein Eng., 9, 616-621, 1996). Immunoglobulin-like domain-based technologies that have created multispecific and/or multivalent molecules include dAbs, TandAbs, nanobodies, BiTEs, SMIPs, DNLs, Affibodies, Fynomers, Kunitz Domains, Albu-dabs, DARTs, DVD-IG, Covx-bodies, peptibodies, scFv-Igs, SVD-Igs, dAb-Igs, Knobs-in-Holes, DuoBodies™ and triomAbs. Bispecific bivalent antibodies, and methods of making them, are described, for instance in U.S. Pat. Nos. 5,731,168; 5,807,706; 5,821,333; and U.S. Patent Appl. Publ. Nos. 2003/020734 and 2002/0155537, the disclosures of all of which are incorporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; 5,601,819; Kostelny et al., J. Immunol. 148: 1547-1553 (1992).

The phrase "effector function" refers to the activities of antibodies that result from the interactions of their Fc components with Fc receptors or components of complement. These activities include, for example, antibody-dependent cell-mediated cytotoxicity (ADCC), complement-dependent cytotoxicity (CDC), and antibody-dependent cell phagocytosis (ADCP). Thus an antigen binding protein (e.g., an antibody or antigen binding fragment thereof) with altered effector function refers to an antigen binding protein (e.g., an antibody or antigen binding fragment thereof) that contains an alteration in an Fc region (e.g., amino acid substitution, deletion, or addition or change in oligosaccharide) that changes the activity of at least one effector function (e.g., ADCC, CDC, and/or ADCP). An antigen binding protein (e.g., an antibody or antigen binding fragment thereof) with improved effector function refers to an antigen binding protein (e.g., an antibody or antigen binding fragment thereof) that contains an alteration in an Fc region (e.g., amino acid substitution, deletion, or addition or change in oligosaccharide) that increases the activity of at least one effector function (e.g., ADCC, CDC, and/or ADCP).

The term "specific" can be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the antigen binding protein carrying the antigen binding domain will be able to bind to the various antigens carrying the epitope.

By "specifically binds" it is generally meant that an antigen binding protein including an antibody or antigen binding fragment thereof binds to an epitope via its antigen binding domain, and that the binding entails some complementarity between the antigen binding domain and the epitope. According to this definition, an antibody is said to "specifically bind" to an epitope when it binds to that epitope via its antigen binding domain more readily than it would bind to a random, unrelated epitope. As used herein, an antigen binding protein that "specifically binds" to *Klebsiella pneumoniae* O1 antigen does not specifically bind to *Klebsiella pneumoniae* O2 antigen.

"Affinity" is a measure of the intrinsic binding strength of a ligand binding reaction. For example, a measure of the strength of the antibody (Ab)-antigen (Ag) interaction is measured through the binding affinity, which may be quantified by the dissociation constant, $k_d$. The dissociation constant is the binding affinity constant and is given by:

$$K_d = \frac{[Ab][Ag]}{[AbAg \text{ complex}]}$$

Affinity may, for example, be measured using a BIAcore®, a KinExA affinity assay, flow cytometry, and/or radioimmunoassay.

"Potency" is a measure of pharmacological activity of a compound expressed in terms of the amount of the compound required to produce an effect of given intensity. It refers to the amount of the compound required to achieve a defined biological effect; the smaller the dose required, the more potent the drug. Potency of an antigen binding protein that binds O1 can, for example, be determined using an OPK assay, as described herein.

"Opsonophagocytic killing" or "OPK" refers to the death of a cell, e.g., a *Klebsiella*, that occurs as a result of phagocytosis by an immune cell. OPK activity is measured according to the bio-luminescent OPK activity used in Example 4. An antigen binding protein (e.g., an antibody or antigen-binding fragment thereof) can induce OPK where the percentage of killing is 40% or greater. An antigen binding protein (e.g., an antibody or antigen-binding fragment thereof) can strongly induce OPK where the percentage of killing is 80% or greater.

Killing can also be measured using a "serum bactericidal assay." Killing via complement fixation on the bacterial surface and the formation of a "Membrane Attack Complex" can be assessed using the assay described in Example 4. An antigen binding protein (e.g., an antibody or antigen-binding fragment thereof) can kill *Klebsiella* as measured by a serum bactericidal assay where the percentage of killing is 40% or greater. An antigen binding protein (e.g., an antibody or antigen-binding fragment thereof) can greatly kill *Klebsiella* as measured by a serum bactericidal assay where the percentage of killing is 80% or greater.

An antigen binding protein including an antibody or antigen binding fragment thereof is said to competitively inhibit binding of a reference antibody or antigen binding fragment thereof to a given epitope or "compete" with a reference antibody or antigen binding fragment if it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope or compete with a reference antibody or antigen binding fragment thereof by at least 90%, at least 80%, at least 70%, at least 60%, or at least 50%.

The term "compete" when used in the context of antigen binding proteins (e.g., neutralizing antigen binding proteins or neutralizing antibodies) means competition between antigen binding proteins as determined by an assay in which the antigen binding protein (e.g., antibody or immunologically functional fragment thereof) under test prevents or inhibits specific binding of a reference antigen binding protein (e.g., a ligand, or a reference antibody) to a common antigen (e.g., an O1 polysaccharide or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, Methods in Enzymology 92:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabeled test antigen binding protein and a labeled reference antigen binding protein.

Competitive inhibition can be measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Usually, when a competing antigen binding protein is present in excess, it will inhibit specific binding of a reference antigen binding protein to a common antigen by at least 40%, 45%, 50%, 55%, 60%, 65%, 70% or 75%. In some instance, binding is inhibited by at least 80%, 85%, 90%, 91%, 92%, 93%, 94%, 95%, 96%, 97% 98%, 99% or more.

Antigen binding proteins, antibodies or antigen binding fragments thereof disclosed herein can be described or specified in terms of the epitope(s) or portion(s) of an antigen, e.g., a target polypeptide that they recognize or specifically bind. For example, the portion of O1 that specifically interacts with the antigen binding domain of the antigen binding polypeptide or fragment thereof disclosed herein is an "epitope". Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. A conformational epitope can be composed of discontinuous sections of the antigen's amino acid sequence. A linear epitope is formed by a continuous sequence of amino acids from the antigen. Epitope determinants may include chemically active surface groupings of molecules such as amino acids, sugar side chains, phosphoryl or sulfonyl groups, and can have specific three dimensional structural characteristics, and/or specific charge characteristics. An epitope typically includes at least 3, 4, 5, 6, 3, 4, 5, 6, 7, 8, 9, 10, 11, 12, 13, 14, 15, 16, 17, 18, 19, 20, 25, 30, 35 amino acids in a unique spatial conformation. Epitopes can be determined using methods known in the art.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

As used herein, the term "polypeptide" refers to a molecule composed of monomers (amino acids) linearly linked by amide bonds (also known as peptide bonds). The term "polypeptide" refers to any chain or chains of two or more amino acids, and does not refer to a specific length of the product. As used herein the term "protein" is intended to encompass a molecule comprised of one or more polypeptides, which can in some instances be associated by bonds other than amide bonds. On the other hand, a protein can also be a single polypeptide chain. In this latter instance the single polypeptide chain can in some instances comprise two or more polypeptide subunits fused together to form a protein. The terms "polypeptide" and "protein" also refer to the products of post-expression modifications, including without limitation glycosylation, acetylation, phosphorylation, amidation, derivatization by known protecting/blocking groups, proteolytic cleavage, or modification by non-naturally occurring amino acids. A polypeptide or protein can be derived from a natural biological source or produced by recombinant technology, but is not necessarily translated from a designated nucleic acid sequence. It can be generated in any manner, including by chemical synthesis.

The term "isolated" refers to the state in which antigen binding proteins of the disclosure, or nucleic acid encoding such binding proteins, will generally be in accordance with the present disclosure. Isolated proteins and isolated nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. Proteins and nucleic acid may be formulated with diluents or adjuvants and still, for practical purposes, be isolated—for example the proteins will normally be mixed with gelatin or other carriers if used to coat microtitre plates for use in immunoassays, or will be mixed with pharmaceutically acceptable carriers or diluents when used in diagnosis or therapy. Antigen binding proteins may be glycosylated, either naturally or by systems of heterologous eukaryotic cells (e.g. CHO or NS0 (ECACC 85110503) cells, or they may be (for example if produced by expression in a prokaryotic cell) unglycosylated.

A polypeptide, antigen binding protein, antibody, polynucleotide, vector, cell, or composition which is "isolated" is a polypeptide, antigen binding protein, antibody, polynucleotide, vector, cell, or composition which is in a form not found in nature. Isolated polypeptides, antigen binding proteins, antibodies, polynucleotides, vectors, cells, or compositions include those which have been purified to a degree that they are no longer in a form in which they are found in nature. In some embodiments, an antigen binding protein, antibody, polynucleotide, vector, cell, or composition which is isolated is substantially pure.

A "recombinant" polypeptide, protein or antibody refers to a polypeptide or protein or antibody produced via recombinant DNA technology. Recombinant polypeptides, proteins and antibodies expressed in host cells are considered isolated for the purpose of the present disclosure, as are native or recombinant polypeptides which have been separated, fractionated, or partially or substantially purified by any suitable technique.

Also included in the present disclosure are fragments, variants, or derivatives of polypeptides, and any combination thereof. The term "fragment" when referring to polypeptides and proteins of the present disclosure include any polypeptides or proteins which retain at least some of the properties of the reference polypeptide or protein. Fragments of polypeptides include proteolytic fragments, as well as deletion fragments.

The term "variant" as used herein refers to an antibody or polypeptide sequence that differs from that of a parent antibody or polypeptide sequence by virtue of at least one amino acid modification. Variants of antibodies or polypeptides of the present disclosure include fragments, and also antibodies or polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

The term "derivatives" as applied to antibodies or polypeptides refers to antibodies or polypeptides which have been altered so as to exhibit additional features not found on the native polypeptide or protein. An example of a "derivative" antibody is a fusion or a conjugate with a second polypeptide or another molecule (e.g., a polymer such as PEG, a chromophore, or a fluorophore) or atom (e.g., a radioisotope).

The terms "polynucleotide" or "nucleotide" as used herein are intended to encompass a singular nucleic acid as well as plural nucleic acids, and refers to an isolated nucleic acid molecule or construct, e.g., messenger RNA (mRNA), complementary DNA (cDNA), or plasmid DNA (pDNA). In certain aspects, a polynucleotide comprises a conventional phosphodiester bond or a non-conventional bond (e.g., an amide bond, such as found in peptide nucleic acids (PNA)).

The term "nucleic acid" refers to any one or more nucleic acid segments, e.g., DNA, cDNA, or RNA fragments, present in a polynucleotide. When applied to a nucleic acid or polynucleotide, the term "isolated" refers to a nucleic acid molecule, DNA or RNA, which has been removed from its native environment, for example, a recombinant polynucleotide encoding an antigen binding protein contained in a vector is considered isolated for the purposes of the present disclosure. Further examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present disclosure. Isolated polynucleotides or nucleic acids according to the present disclosure further include such molecules produced synthetically. In addition, a polynucleotide or a nucleic acid can include regulatory elements such as promoters, enhancers, ribosome binding sites, or transcription termination signals.

As used herein, the term "host cell" refers to a cell or a population of cells harboring or capable of harboring a recombinant nucleic acid. Host cells can be a prokaryotic cells (e.g., *E. coli*), or alternatively, the host cells can be eukaryotic, for example, fungal cells (e.g., yeast cells such as *Saccharomyces cerivisiae, Pichia pastoris*, or *Schizosaccharomyces pombe*), and various animal cells, such as insect cells (e.g., Sf-9) or mammalian cells (e.g., HEK293F, CHO, COS-7, NIH-3T3, a NS0 murine myeloma cell, a PER.C6® human cell, a Chinese hamster ovary (CHO) cell or a hybridoma).

The term "amino acid substitution" refers to replacing an amino acid residue present in a parent sequence with another amino acid residue. An amino acid can be substituted in a parent sequence, for example, via chemical peptide synthesis or through recombinant methods known in the art. Accordingly, references to a "substitution at position X" or "substitution at position X" refer to the substitution of an amino acid present at position X with an alternative amino acid residue. In some embodiments, substitution patterns can described according to the schema AXY, wherein A is the single letter code corresponding to the amino acid naturally present at position X, and Y is the substituting amino acid residue. In other aspects, substitution patterns can described according to the schema XY, wherein Y is the single letter code corresponding to the amino acid residue substituting the amino acid naturally present at position X.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

Non-conservative substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Be or Trp) is substituted for, or by, one having a smaller side chain (e.g., Ala, Ser) or no side chain (e.g., Gly).

Other substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

The term "amino acid insertion" refers to introducing a new amino acid residue between two amino acid residues present in the parent sequence. An amino acid can be inserted in a parent sequence, for example, via chemical peptide synthesis or through recombinant methods known in the art. Accordingly as used herein, the phrases "insertion between positions X and Y," "insertion between IMGT positions X and Y," or "insertion between Kabat positions X and Y," wherein X and Y correspond to amino acid positions (e.g., a cysteine amino acid insertion between positions 239 and 240), refers to the insertion of an amino acid between the X and Y positions, and also to the insertion in a nucleic acid sequence of a codon encoding an amino acid between the codons encoding the amino acids at positions X and Y. Insertion patterns can be described according to the schema AXins, wherein A is the single letter code corresponding to the amino acid being inserted, and X is the position preceding the insertion.

The term "percent sequence identity" or "percent identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence. The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software programs. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

"Specific binding member" describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organization of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. The present disclosure is concerned with antigen-antibody type reactions.

The term "IgG" as used herein refers to a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, and IgG3.

The term "antigen binding domain" describes the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain). An antigen binding domain may comprise an antibody light chain variable region (VL) and an antibody heavy chain variable region (VH).

The term "antigen binding protein fragment" or "antibody fragment" refers to a portion of an intact antigen binding protein or antibody and refers to the antigenic determining variable regions of an intact antigen binding protein or antibody. It is known in the art that the antigen binding function of an antibody can be performed by fragments of a full-length antibody. Examples of antibody fragments include, but are not limited to Fab, Fab', F(ab')$_2$, and Fv fragments, linear antibodies, single chain antibodies, and multispecific antibodies formed from antibody fragments.

The term "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')$_2$, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides. The term "humanized antibody" refers to an antibody derived from a non-human (e.g., murine) immunoglobulin, which has been engineered to contain minimal non-human (e.g., murine) sequences.

The term "chimeric antibody" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

The term "antibody binding site" refers to a region in the antigen (e.g., O1) comprising a continuous or discontinuous site (i.e., an epitope) to which a complementary antibody specifically binds. Thus, the antibody binding site can contain additional areas in the antigen which are beyond the epitope and which can determine properties such as binding affinity and/or stability, or affect properties such as antigen enzymatic activity or dimerization. Accordingly, even if two antibodies bind to the same epitope within an antigen, if the antibodies establish distinct intermolecular contacts with amino acids outside of the epitope, such antibodies are considered to bind to distinct antibody binding sites.

The IMGT numbering system is generally used when referring to a residue in the variable domain (approximately residues 1-107 of the light chain and residues 1-113 of the heavy chain) (e.g., Lefranc, M.-P. et al. Dev. Comp. Immunol. 27: 55-77 (2003)).

The phrases "amino acid position numbering as in Kabat," "Kabat position," and grammatical variants thereof refer to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82. Antibody 54H7 is numbered according to the Kabat system.

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. The IMGT (Lefranc, M.-P. et al. Dev. Comp. Immunol. 27: 55-77 (2003)) classification of CDRs can also be used.

The term "EU index as in Kabat" refers to the numbering system of the human IgG1 EU antibody described in Kabat et al., Sequences of Immunological Interest, 5th Ed. Public Health Service, National Institutes of Health, Bethesda, Md. (1991). For example, both "L234" and "EU L234" refer to the amino acid leucine at position 234 according to the EU index as set forth in Kabat.

The terms "Fc domain," "Fc Region," and "IgG Fc domain" as used herein refer to the portion of an immunoglobulin, e.g., an IgG molecule, that correlates to a crystallizable fragment obtained by papain digestion of an IgG molecule. The Fc region comprises the C-terminal half of two heavy chains of an IgG molecule that are linked by disulfide bonds. It has no antigen binding activity but contains the carbohydrate moiety and binding sites for complement and Fc receptors, including the FcRn receptor. For example, an Fc domain contains the entire second constant domain CH2 (residues at EU positions 231-340 of human IgG1) and the third constant domain CH3 (residues at EU positions 341-447 of human IgG1).

Fc can refer to this region in isolation, or this region in the context of an antibody, antibody fragment, or Fc fusion protein. Polymorphisms have been observed at a number of positions in Fc domains, including but not limited to EU positions 270, 272, 312, 315, 356, and 358. Thus, a "wild type IgG Fc domain" or "WT IgG Fc domain" refers to any naturally occurring IgG Fc region (i.e., any allele). Myriad Fc mutants, Fc fragments, Fc variants, and Fc derivatives are described, e.g., in U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 7,122,637; 7,183,387; 7,332,581; 7,335,742; 7,371,826; 6,821,505; 6,180,377; 7,317,091; 7,355,008; U.S. Patent publication 2004/0002587; and PCT Publication Nos. WO 99/058572, WO 2011/069164 and WO 2012/006635.

The sequences of the heavy chains of human IgG1, IgG2, IgG3 and IgG4 can be found in a number of sequence databases, for example, at the Uniprot database (www.uniprot.org) under accession numbers P01857 (IGHG1_HUMAN), P01859 (IGHG2_HUMAN), P01860 (IGHG3_HUMAN), and P01861 (IGHG1_HUMAN), respectively.

The terms "YTE" or "YTE mutant" refer to a set of mutations in an IgG1 Fc domain that results in an increase in the binding to human FcRn and improves the serum half-life of the antibody having the mutation. A YTE mutant comprises a combination of three "YTE mutations": M252Y, S254T, and T256E, wherein the numbering is according to the EU index as in Kabat, introduced into the heavy chain of an IgG. See U.S. Pat. No. 7,658,921, which is incorporated by reference herein. The YTE mutant has been shown to increase the serum half-life of antibodies compared to wild-type versions of the same antibody. See, e.g., Dall'Acqua et al., J. Biol. Chem. 281:23514-24 (2006) and U.S. Pat. No. 7,083,784, which are hereby incorporated by reference in their entireties. A "Y" mutant comprises only the M256Y mutations; similarly a "YT" mutation comprises only the M252Y and S254T; and a "YE" mutation comprises only the M252Y and T256E. It is specifically contemplated that other mutations may be present at EU positions 252 and/or 256. In certain aspects, the mutation at EU position 252 may be M252F, M252S, M252W or M252T and/or the mutation at EU position 256 may be T256S, T256R, T256Q or T256D.

The term "N3" or "N3 mutant" refers to a set of mutations in an IgG1 Fc domain that results in an increase in the binding to FcRn and improves the serum half-life of the antibody having the mutation. The N3 mutant comprises the sequence Cys-Ser-Trp-His-Leu-Cys (SEQ ID NO: 68) at positions 432-437 (no insertion between positions 437 and 438), incorporated into a wild type IgG1 constant domain base structure, See WO2015175874, which is hereby incorporated by reference.

The term "naturally occurring O1" generally refers to a state in which the O1 polysaccharide or a fragment thereof can occur. Naturally occurring O1 means O1 polysaccharide which is naturally produced by a cell, without prior introduction of encoding nucleic acid using recombinant technology. Thus, naturally occurring O1 can be as produced naturally by for example K. pneumoniae and/or as isolated from different members of the Klebsiella genus.

The term "recombinant O1" refers to a state in which the O1 polysaccharide or fragments thereof may occur. Recombinant O1 means O1 polysaccharide or fragments thereof produced by recombinant DNA, e.g., in a heterologous host.

The terms "half-life" or "in vivo half-life" as used herein refer to the biological half-life of a particular type of antibody, antigen binding protein, or polypeptide of the present disclosure in the circulation of a given animal and is represented by a time required for half the quantity administered in the animal to be cleared from the circulation and/or other tissues in the animal.

The term "subject" as used herein refers to any animal (e.g., a mammal), including, but not limited to humans, non-human primates, rodents, sheep, dogs, cats, horses, cows, bears, chickens, amphibians, reptiles, and the like, which is to be the recipient of a particular treatment. The terms "subject" and "patient" as used herein refer to any subject, particularly a mammalian subject, for whom diagnosis, prognosis, or therapy of a condition associated with a Klebsiella infection. As used herein, phrases such as "a patient having a condition associated with a Klebsiella infection" includes subjects, such as mammalian subjects, that would benefit from the administration of a therapy, imaging or other diagnostic procedure, and/or preventive treatment for that condition associated with a Klebsiella infection.

"Klebsiella" refers to a genus of gram-negative, facultatively anaerobic, rod-shaped bacteria in the Enterobacteriaceae family. Klebsiella include, for example, K. pneumoniae, K. oxytoca, K. planticola K. granulomatis, K. ozaenae, and K. rhinoscleromatis.

Members of the Klebsiella genus typically express at least 2 types of carbohydrate antigens on their cell surface: an O antigen and a K antigen. The O antigen is a lipopolysaccharide, and the K antigen is a capsular polysaccharide. The structural variability of these antigens forms the basis for their classification in Klebsiella "serotypes." Thus, the ability of an O1 binding protein (e.g., an antibody or an antigen binding fragment thereof) to bind to multiple Klebsiella strains or serotypes refers to its ability to bind to Klebsiella with different O and/or K antigens. In some embodiments provided herein, the Klebsiella is of the O1 serotype.

The term "pharmaceutical composition" as used herein refers to a preparation which is in such form as to permit the biological activity of the active ingredient to be effective, and which contains no additional components which are unacceptably toxic to a subject to which the composition would be administered. Such composition can be sterile.

An "effective amount" of an antigen binding protein (including an antibody or antigen binding fragment thereof), as disclosed herein is an amount sufficient to carry out a specifically stated purpose. An "effective amount" can be determined empirically and in a routine manner, in relation to the stated purpose. The term "therapeutically effective amount" as used herein refers to an amount of a polypeptide, e.g., an antigen binding protein including an antibody, or other drug effective to "treat" a disease or condition in a subject or mammal and provides some improvement or benefit to a subject having a Klebsiella-mediated disease or condition. Thus, a "therapeutically effective" amount is an amount that provides some alleviation, mitigation, and/or decrease in at least one clinical symptom of the Klebsiella-mediated disease or condition. Clinical symptoms associated with the Klebsiella-mediated disease or condition that can be treated by the methods and systems of the disclosure are well known to those skilled in the art. Further, those skilled in the art will appreciate that the therapeutic effects need not be complete or curative, as long as some benefit is provided to the subject. In some embodiments, the term "therapeutically effective" refers to an amount of a therapeutic agent that is capable of reducing *Klebsiella* (e.g., *K. pneumoniae*) or *Klebsiella* (e.g., *K. pneumoniae*) activity in a patient in need thereof. The actual amount administered and rate and time-course of administration, will depend on the nature and severity of what is being treated. Prescription of treatment, e.g. decisions on dosage etc., is within the responsibility of general practitioners and other medical doctors. Appropriate doses of antibodies and antigen binding fragments thereof are well known in the art; see Ledermann J. A. et al. (1991) Int. J. Cancer 47: 659-664; Bagshawe K. D. et al. (1991) Antibody, Immunoconjugates and Radiopharmaceuticals 4: 915-922.

As used herein, a "sufficient amount" or "an amount sufficient to" achieve a particular result in a patient having a *Klebsiella*-mediated disease or condition refers to an amount of a therapeutic agent (e.g., an antigen binding protein including an antibody, as disclosed herein) that is effective to produce a desired effect, which is optionally a therapeutic effect (i.e., by administration of a therapeutically effective amount). In some embodiments, such particular result is a reduction in *Klebsiella* (e.g., *K. pneumoniae*) or *Klebsiella* (e.g., *K. pneumoniae*) activity in a patient in need thereof.

The term "label" when used herein refers to a detectable compound or composition which is conjugated directly or indirectly to a polypeptide, e.g., an antigen binding protein including an antibody, so as to generate a "labeled" polypeptide or antibody. The label can be detectable by itself (e.g., radioisotope labels or fluorescent labels) or, in the case of an enzymatic label, can catalyze chemical alteration of a substrate compound or composition which is detectable.

Terms such as "treating" or "treatment" or "to treat" or "alleviating" or "to alleviate" or "ameliorating" or "or ameliorate" refer to therapeutic measures that cure, slow down, lessen symptoms of, and/or halt progression of a diagnosed pathologic condition or disorder. Terms such as "preventing" refer to prophylactic or preventative measures that prevent and/or slow the development of a targeted pathologic condition or disorder. Thus, those in need of treatment include those already with the disease or condition. Those in need of prevention include those prone to have the disease or condition and those in whom the disease or condition is to be prevented. For example, the phrase "treating a patient having a *Klebsiella*-mediated disease or condition" refers to reducing the severity of the *Klebsiella*-mediated disease or condition, preferably, to an extent that the subject no longer suffers discomfort and/or altered function due to it (for example, a relative reduction in asthma exacerbations when compared to untreated patients). The phrase "preventing a *Klebsiella*-mediated disease or condition" refers to reducing the potential for a *Klebsiella*-mediated disease or condition and/or reducing the occurrence of the *Klebsiella*-mediated disease or condition.

As used herein, the term "a condition associated with a *Klebsiella* infection" refers to any pathology caused by (alone or in association with other mediators), exacerbated by, associated with, or prolonged by *Klebsiella* infection (e.g. infection with *K. pneumoniae, K. oxytoca, K. planticola, K. ozaenae, K. rhinosclermoatis* and/or *K. granulomatis*) in the subject having the disease or condition. Non-limiting examples of conditions associated with a *Klebsiella* infection include pneumonia, urinary tract infection, septicemia/sepsis, neonatal septicemia, diarrhea, soft tissue infections, infections following an organ transplant, surgery infection, wound infection, lung infection, pyogenic liver abscesses, endophthalmitis, meningitis, necrotizing meningitis, ankylosing spondylitis and spondyloarthropathies. In some embodiments, the *Klebsiella* infection is a nosocomial infection. In some embodiments, the *Klebsiella* infection is an opportunistic infection. In some embodiments, the *Klebsiella* infection follows an organ transplant. In some embodiments, the subject is exposed to a *Klebsiella* contaminated medical device, including, e.g., a ventilator, a catheter, or an intravenous catheter.

The structure for carrying a CDR or a set of CDRs will generally be of an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to (Kabat, E. A. et al, Sequences of Proteins of Immunological Interest. 4th Edition. US Department of Health and Human Services. 1987, and updates thereof, now available on the Internet (http://immuno.bme.nwu.edu or find "Kabat" using any search engine), herein incorporated by reference. CDRs can also be carried by other scaffolds such as fibronectin or cytochrome B.

A CDR amino acid sequence substantially as set out herein can be carried as a CDR in a human variable domain or a substantial portion thereof. The HCDR3 sequences substantially as set out herein represent embodiments of the present disclosure and each of these may be carried as a HCDR3 in a human heavy chain variable domain or a substantial portion thereof.

Variable domains employed in the disclosure can be obtained from any germ-line or rearranged human variable domain, or can be a synthetic variable domain based on consensus sequences of known human variable domains. A CDR sequence (e.g. CDR3) can be introduced into a repertoire of variable domains lacking a CDR (e.g. CDR3), using recombinant DNA technology.

For example, Marks et al. (Bio/Technology, 1992, 10:779-783; which is incorporated herein by reference) provide methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire can be combined with a CDR3 of a particular antibody. Using analogous techniques, the CDR3-derived sequences of the present disclosure can be shuffled with repertoires of VH or VL domains lacking a CDR3, and the shuffled complete VH or VL domains combined with a cognate VL or VH domain to provide antigen binding proteins. The repertoire can then be displayed in a suitable host system such as the phage display system of WO92/01047 or any of a subsequent large body of literature, including Kay, B. K., Winter, J., and McCafferty, J. (1996) Phage Display of Peptides and Proteins: A Laboratory Manual, San Diego: Academic Press, so that suitable antigen binding proteins may be selected. A repertoire can consist of from anything from 104 individual members upwards, for example from 106 to 108 or 1010 members. Other suitable host systems include yeast display, bacterial display, T7 display, ribosome display and so on. For a review of ribosome display for see Lowe D and Jermutus L, 2004, Curr. Pharm, Biotech, 517-27, also WO92/01047, which are herein incorporated by reference.

Analogous shuffling or combinatorial techniques are also disclosed by Stemmer (Nature, 1994, 370:389-391, which is herein incorporated by reference), who describes the technique in relation to a β-lactamase gene but observes that the approach may be used for the generation of antibodies.

A further alternative is to generate novel VH or VL regions carrying CDR-derived sequences of the disclosure using random mutagenesis of one or more selected VH and/or VL genes to generate mutations within the entire variable domain. Such a technique is described by Gram et al (1992, Proc. Natl. Acad. Sci., USA, 89:3576-3580), who used error-prone PCR. In some embodiments, one or two amino acid substitutions are made within a set of HCDRs and/or LCDRs.

Another method which may be used is to direct mutagenesis to CDR regions of VH or VL genes. Such techniques are disclosed by Barbas et al, (1994, Proc. Natl. Acad. Sci., USA, 91:3809-3813) and Schier et al (1996, J. Mol. Biol. 263:551-567).

The methods and techniques of the present disclosure are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), all of which are herein incorporated by reference.

The skilled person will be able to use such techniques described above to provide antigen binding proteins of the present disclosure using routine methodology in the art.

II. O1 Antigen Binding Molecules

The present disclosure provides O1 antigen binding molecules, e.g., antigen binding proteins, antibodies, and antigen binding fragments thereof, that specifically bind *K. pneumoniae* O1 antigen. As defined herein "O1 antigen binding molecules" including antibodies and antigen binding fragments thereof, do not bind to O2. Collectively, these agents are referred to herein as "O1 binding molecules" or "O1-binding agents."

The O1 antigen of *Klebsiella* lipopolysaccharide (LPS) contains two structural distinct domains composed of the repeat units D-galactan (D-Gal I) I and D-galactan II (D-Gal II). See FIG. 12. The low-molecular-weight D-Gal I polymers are directly linked to the core oligosaccharide and are composed of repeat units of the structure →3)-β-D-Galf-(1→3)-α-D-Galp-(1→. The O-antigen biosynthesis is performed in part by products of the wb (rfb) gene cluster, which is composed of six genes (wzm, wzt, glf, wbbM, wbbN, and wbbO) (Whitfield, C. et al. 1991. Expression of two structurally distinct D-Galactan O antigens in the lipopolysaccharide of *Klebsiella pneumoniae* serotype O1. J. Bacteriology. 1420-1431; Clarke, B. R. and Whitfield C. 1992. Molecular cloning of the rib region of *Klebsiella pneumoniae* serotype O1:K20. J. Bacteriology. 174: 4614-4621). D-Gal I domain is also the major O-antigen component for *Klebsiella* O2 LPS. The high molecular weight D-Gal II polymers, which are linked to the distal ends of D-Gal I, consist of repeating units of the structure →3)-α-D-Galp-(1→3)-β-D-Galp-(1→. The genes required for D-Gal II biosynthesis were recently identified as wbbY and wbbZ, which are not linked to wb cluster. (see, Hsieh, P. et al. 2014. D-galactan II is an immunodominant antigen in O1 LPS and affects virulence in *Klebsiella pneumoniae*: implication in vaccine design. Frontiers in Microbiology. 5: 1-13). The addition of D-Gal II defines O1 serotypes and contributes to serum resistance as well as high prevalence rate among *Klebsiella pneumoniae* causing PLA. (Hsieh, P. F. 2012. Lipopolysaccharide O1 antigen contributes to the virulence in *Klebsiella pneumoniae* causing primary pyogenic liver abscess.; Pan Y-J., et al., PLoS ONE 7(3): e33155 (2013) doi:10.1371/journal.pone.0033155).

In some embodiments, the disclosure provides an isolated antigen binding protein that is an antibody or polypeptide that specifically binds to *K. pneumoniae* O1 antigen. In some embodiments, the antigen binding protein is an antigen binding fragment of an antibody that specifically binds to *K. pneumoniae* O1 antigen.

In certain embodiments, the O1 binding molecules are antibodies or polypeptides. In some embodiments, the disclosure provides an isolated antigen binding protein that is a murine, non-human, humanized, chimeric, resurfaced, or human antigen binding protein that specifically binds to *K. pneumoniae* O1 antigen. In some embodiments, the disclosure provides an isolated antigen binding protein that is a humanized, chimeric, resurfaced, or human antigen binding protein that specifically binds to *K. pneumoniae* O1 antigen. In some embodiments, the O1 binding molecules are humanized antibodies or antigen binding fragment thereof. In some embodiments, the O1 binding molecule is a human antibody or antigen binding fragment thereof.

The disclosure provides an isolated antigen binding protein (including an antibody or antigen binding fragment thereof) that specifically binds to *K. pneumoniae* O1 antigen, wherein said antigen binding protein (e.g., an antibody or antigen binding fragment thereof): a) induces opsonophagocytic killing (OPK) of *Klebsiella* (e.g., *K. pneumoniae*); b) kills *Klebsiella* (e.g., *K. pneumoniae*) via complement dependent killing as measured by a serum bactericidal assay or c) induces OPK of *Klebsiella* (e.g., *K. pneumoniae*) and kills *Klebsiella* (e.g., *K. pneumoniae*) via complement dependent killing as measured by a serum bactericidal assay.

The disclosure also provides an isolated antigen binding protein (including an antibody or antigen binding fragment thereof) that specifically binds to *K. pneumoniae* O1 antigen, wherein said antigen binding protein (e.g., an antibody or antigen binding fragment thereof) induces OPK but does not neutralize LPS. As demonstrated in the Examples provided herein, high levels of in vivo activity are associated with antigen binding proteins that specifically bind to *K. pneumoniae* O1 antigen and induce OPK, but do not neutralize LPS.

The disclosure also provides an isolated antigen binding protein (including an antibody or antigen binding fragment thereof) that specifically binds to *K. pneumoniae* O1 antigen, wherein said antigen binding protein (e.g., an antibody or antigen binding fragment thereof) induces OPK and neutralizes LPS.

The O1-binding agents include anti-O1 antigen antibodies KPE33, KPE33V2016, KPA27, KPB202, KBJ4, 54H7, and antigen-binding fragments thereof. The O1-binding agents also include O1-binding agents (e.g., anti-O1 antigen antibodies or antigen-binding fragments thereof) that specifically bind to the same *K. pneumoniae* O1 epitope as KPE33, KPE33V2016, KPA27, KPB202, KBJ4, or 54H7.

In some embodiments, the O1-binding agents, e.g., an anti-O1 antigen antibody or antigen-binding fragments thereof, do not include antibody clone Ru-O1. See Rukavina T., et al., *Infect Immun* 65:1754-60 (1997). In some embodiments, the O1-binding agent, e.g., an anti-O1 antigen antibody or antigen-binding fragments thereof, is not a murine antibody.

In some embodiments, the O1 binding protein (e.g., an anti-O1 antigen antibody or antigen-binding fragment thereof) binds to the D-Galactan II domain of *K. pneumoniae* O1 antigen. In some embodiments, the O1 binding protein (e.g., an anti-O1 antigen antibody or antigen-binding fragment thereof) binds to an epitope within the D-Galactan II domain of *K. pneumoniae* O1 antigen.

The O1-binding agents (e.g. anti-O1 antigen antibodies or antigen binding fragments thereof) also include O1-binding agents that competitively inhibit binding of KPE33, KPE33V2016, KPA27, KPB202, KPJ4, or 54H7 to *K. pneumoniae* O1 antigen. In some embodiments, an anti-O1 antibody or antigen-binding fragment thereof competitively inhibits binding of KPE33, KPE33V2016, KPA27, KPB202, KPJ4, or 54H7 to *K. pneumoniae* O1 antigen in a competition ELISA assay. In some embodiments, an anti-O1 antibody or antigen-binding fragment thereof competitively inhibits binding of KPE33, KPE33V2016, KPA27, KPB202, KPJ4, or 54H7 to *K. pneumoniae* in a competition ELISA assay.

In some embodiments, the O1-binding agents (e.g. anti-O1 antigen antibodies or antigen binding fragments thereof) also include O1-binding agents that competitively inhibit binding of 54H7 to *K. pneumoniae* O1 antigen but do not competitively inhibit binding of KPE33 to *K. pneumoniae* O1 antigen, e.g., as measured by the Octet platform. In some embodiments, the O1-binding agents (e.g. anti-O1 antigen antibodies or antigen binding fragments thereof) also include O1-binding agents that competitively inhibit binding of KPE33 to *K. pneumoniae* O1 antigen but do not competitively inhibit binding of 54H7 to *K. pneumoniae* O1 antigen, e.g., as measured by the Octet platform.

In some embodiments, an anti-O1 antibody or antigen-binding fragment thereof binds to an O1 *Klebsiella* strain (including, e.g., a *K. pneumoniae* O1 strain), but does not bind to the corresponding wbbYZ knockout strain (e.g., as measured by FACS assay). In some embodiments, an anti-O1 antibody or antigen-binding fragment thereof binds to the *Klebsiella* strain Kp1131115 but does not bind to the Kp1131115ΔwbbYZ knockout strain (e.g., as measured by FACS assay).

The O1-binding agents (e.g. anti-O1 antigen antibodies or antigen binding fragments thereof) also include O1-binding agents that comprise the heavy and light chain complementarity determining region (CDR) sequences of KPE33, KPE33V2016, KPA27, KPB202, KBJ4, or 54H7. The CDR sequences of KPE33, KPE33V2016, KPA27, KPB202, KBJ4, and 54H7 are described in Tables 1 and 2 below. For all antibodies other than 54H7, the CDRs listed in Tables 1 and 2 were determined using the IMGT system. For 54H7, CDRs were determined using the Kabat system.

TABLE 1

Variable heavy chain CDR amino acid sequences

| Antibody | VH-CDR1 | VH-CDR2 | VH-CDR3 |
|---|---|---|---|
| KPE33 | GFIFDDYA (SEQ ID NO: 1) | IAWKSGAT (SEQ ID NO: 2) | TRRRASGDDTFYYFDY (SEQ ID NO: 3) |

TABLE 1-continued

Variable heavy chain CDR amino acid sequences

| Antibody | VH-CDR1 | VH-CDR2 | VH-CDR3 |
|---|---|---|---|
| KPE33V2016 | GFIFDDYA (SEQ ID NO: 1) | IAWKSGAT (SEQ ID NO: 2) | TRRRASGDDTFYYFDY (SEQ ID NO: 3) |
| KPA27 | ENTFNDFY (SEQ ID NO: 14) | IHPDGVVT (SEQ ID NO: 15) | MRDGPGSEGSWFDY (SEQ ID NO: 16) |
| KBPJ4 | GDSVSSNTAA (SEQ ID NO: 23) | TYYRSEWYN (SEQ ID NO: 24) | ARISWNDLPA (SEQ ID NO: 25) |
| KPB202 | GFTFSNFW (SEQ ID NO: 32) | INPDGSEK (SEQ ID NO: 33) | ARLGPFHPDC (SEQ ID NO: 34) |
| 54H7 | NYWMQ (SEQ ID NO: 41) | NIYPGSGNT NYDEKFRS (SEQ ID NO: 42) | NWNFDY (SEQ ID NO: 43) |
| KPE33-H32 + L2016 (E1Q) | GFIFDDYA (SEQ ID NO: 1) | IAYKSGAT (SEQ ID NO: 59) | ~~RRRASGDDTFYYFDY~~ TRRRASGDNTFYYFDY (SEQ ID NO: 60) |
| KPE33-H33 + L2016 (E1Q) | GFIFDDYA (SEQ ID NO: 1) | IAYKSGAT (SEQ ID NO: 59) | ~~RRRASGDDTFYYFDY~~ TRRRASGDNTFYYFDY (SEQ ID NO: 60) |

TABLE 2

Variable light chain CDR amino acid sequences

| Antibody | VL-CDR1 | VL-CDR2 | VL-CDR3 |
|---|---|---|---|
| KPE33 | QNVNTN (SEQ ID NO: 4) | DAS (SEQ ID NO: 5) or LIYDASTRA (SEQ ID NO: 6) | QQCTNWRYT (SEQ ID NO: 7) |
| KPE33V2016 | QNVNTN (SEQ ID NO: 4) | DAS (SEQ ID NO: 5) or LIYDASNRA (SEQ ID NO: 10) | QQTTNWRYT (SEQ ID NO: 11) |
| KPA27 | QPVSNR (SEQ ID NO: 17) | KAS (SEQ ID NO: 18) or LIYKASTLQ (SEQ ID NO: 19) | QQSQT (SEQ ID NO: 20) |
| KPJ4 | QSILYSSHNKNY (SEQ ID NO: 26) | WAS (SEQ ID NO: 27) or LIYWASTRE (SEQ ID NO: 28) | QQYCNIPYT (SEQ ID NO: 29) |
| KPB202 | QSLVHSDGNTY (SEQ ID NO: 35) | EVS (SEQ ID NO: 36) or LIYEVSNRD (SEQ ID NO: 37) | MQGTHWPWT (SEQ ID NO: 38) |

TABLE 2-continued

Variable light chain CDR amino acid sequences

| Antibody | VL-CDR1 | VL-CDR2 | VL-CDR3 |
|---|---|---|---|
| 54H7 | RASQDIGSSLN (SEQ ID NO: 44) | ATSSLDS (SEQ ID NO: 45) | LQHTDSPYT (SEQ ID NO: 46) |
| KPE33-H32 + L2016 (E1Q) | QNVNTN (SEQ ID NO: 4) | DAS (SEQ ID NO: 5) or LIYDASNRA (SEQ ID NO: 10) | QQTTNWRYT (SEQ ID NO: 11) |
| KPE33-H33 + L2016 (E1Q) | QNVNTN (SEQ ID NO: 4) | DAS (SEQ ID NO: 5) or LIYDASNRA (SEQ ID NO: 10) | QQTTNWRYT (SEQ ID NO: 11) |

Antigen binding proteins (including anti-O1 antigen antibodies or antigen binding fragments thereof) described herein can comprise one of the individual variable light chains or variable heavy chains described herein. Antigen binding proteins (including anti-O1 antigen antibodies or antigen binding fragments thereof) described herein can also comprise both a variable light chain and a variable heavy chain. The variable light chain and variable heavy chain sequences of anti-O1 antigen KPE33, KPE33V2016, KPA27, KPB202, KBJ4, and 54H7 antibodies are provided in Tables 3 and 4 below.

TABLE 3

Variable heavy chain amino acid sequences

| Antibody | VH Amino Acid Sequence (SEQ ID NO) |
|---|---|
| KPE33 | EVQLVESGGALVQPGGSLRLSCAVSGFIFDDYAIHWVRRAPGKGLEWVSGIAWKSGATNYADSVKGRFAISRDNSKKSMYLQMNSLGTEDTALYYCTRRRASGDDTFYYFDYWGQGTLVTVSS (SEQ ID NO: 8) |
| KPE33V2016 | EVQLVESGGGLVQPGRSLRLSCAASGFIFDDYAMHWVRQAPGKGLEWVSGIAWKSGATNYADSVKGRFAISRDNSKKSMYLQMNSLGTEDTALYYCTRRRASGDDTFYYFDYWGQGTLVTVSS (SEQ ID NO: 12) |
| KPA27 | QVQLVQSGAEVKKPGASVKVSCKASENTFNDFYMHWVRQAPGQGLEWMGWIHPDGVVTNYAQKFQGRVTMTRDTSINTVYMELNGLISDDTAVYYCMRDGPGSEGSWFDYWGQGTLVTVSS (SEQ ID NO: 21) |
| KBJ4 | QVQLQQSGPGLVRPSQTLSLTCAISGDSVSSNTAAWNWIRQSPSRGLEWLGRTYYRSEWYNDYAVSVKSRITINPDTSKNQFSLQLNSVTPEDTAVYYCARISWNDLPAWGQGTLVTVSS (SEQ ID NO: 30) |
| KPB202 | EVQLVESGGGLVQPGGSLSLSCAASGFTFSNFWVGWGRQAPGKGLEWVANINPDGSEKYYVDSVKGRVTISRDNAKNSLSLQMNSLRVEDAAVYYCARLGPFHPDCWGQGTLVTVSS (SEQ ID NO: 39) |
| 54H7 | QVHLQQPGSELVRPGASVTLSCKASGYTFTNYWMQWVKQRPGQGLEWIGNIYPGSGNTNYDEKFRSKATLTVDTSSSTAYMHLTSLTSEDSAVYYCTRNWNFDYWGQGTTLTVSS (SEQ ID NO: 47) |
| KPE33-H32 + L2016 (E1Q) | QVQLVESGGGLVQPGRSLRLSCAASGFIFDDYAIHWVRQAPGKGLEWVSGIAYKSGATNYAESVKGRFTISRDQSKNSLYLQMNSLRAEDTALYYCTRRRASGDNTFYYFDYWGQGTLVTVSS (SEQ ID NO: 61) |
| KPE33-H33 + L2016 (E1Q) | QVQLVESGGGLVQPGRSLRLSCAASGFIFDDYAIHWVRQAPGKGLEWVSGIAYKSGATNYAESVKGRFTISRDQSKKSLYLQMNSLRAEDTALYYCTRRRASGDNTFYYFDYWGQGTLVTVSS (SEQ ID NO: 62) |

TABLE 4

Variable light chain amino acid sequences

| Antibody | VL Amino Acid Sequence (SEQ ID NO) |
|---|---|
| KPE33 | EIVLTQSPATLSLSPGERATLSCRASQNVNTNLAWYQQRPGQSPRLLIYDASTRAAGLPARFSGSGSGTDFTLTISSLEPEDFAVYYCQQCTNWRYTFGQGTKLEIK (SEQ ID NO: 9) |
| KPE33V2016 | EIVLTQSPATLSLSPGERATLSCRASQNVNTNLAWYQQKPGQAPRLLIYDASNRATGIPARFSGSGSGTDFTLTISSLEPEDFAVYYCQQTTNWRYTFGQGTKLEIK (SEQ ID NO: 13) |
| KPA27 | DIQMTQSPSTLSASVGDRVTITCRASQPVSNRLAWYQQKPGRAPTLLIYKASTLQSGVPLRFSGSGSGTEFTLTISSLQSDDFATYYCQQSQTFGQGTKVEIK (SEQ ID NO: 22) |
| KPJ4 | DIVMTQSPDSLAVSLGERATINCKSSQSILYSSHNKNYLAWYQQKPGQPPKVLIYWASTRESGVPDRFSGSGSGTDFTLTISNLQAEDVAVYYCQQYCNIPYTFGQGTKLEIK (SEQ ID NO: 31) |
| KPB202 | DVVMTQSPLSLPVTLGQPASISCRSSQSLVHSDGNTYLNWFQQRPGQSPRRLIYEVSNRDSGVPDRFSGSGSGTDFTLKISRVEAEDIGVYYCMQGTHWPWTFGQGTKVEIK (SEQ ID NO: 40) |
| 54H7 | DIQMTQSPSSLSASLGERVSLTCRASQDIGSSLNWLQQEPDGTIKRLIYATSSLDSGVPKRFSGSRSGSEYSLTISSLEAEDFVDYYCLQHTDSPYTFGGGTKLELK (SEQ ID NO: 48) |
| KPE33-H32 + L2016 (E1Q) | QIVLTQSPATLSLSPGERATLSCRASQNVNTNLAWYQQKPGQAPRLLIYDASNRATGIPARFSGSGSGTDFTLTISSLEPEDFAVYYCQQTTNWRYTFGQGTKLEIK (SEQ ID NO: 63) |
| KPE33-H33 + L2016 (E1Q) | QIVLTQSPATLSLSPGERATLSCRASQNVNTNLAWYQQKPGQAPRLLIYDASNRATGIPARFSGSGSGTDFTLTISSLEPEDFAVYYCQQTTNWRYTFGQGTKLEIK (SEQ ID NO: 63) |

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a heavy chain variable region (VH) at least 95, 96, 97, 98, or 99% identical to SEQ ID NOs: 8, 12, 21, or 30 and a light chain variable region (VL) at least 95, 96, 97, 98, or 99% identical to SEQ ID NOs: 9, 13, 22, 31. In some embodiments, the isolated antigen binding protein (including, e.g., anti-O1 antigen antibodies or antigen-binding fragments thereof) that specifically binds to *K. pneumoniae* O1 antigen comprises a heavy chain variable region comprising the sequences of SEQ ID NOs: 8, 12, 21, or 30 and a light chain variable region comprising the sequences of SEQ ID NOs: 9, 13, 22, 31. In some embodiments, the isolated antigen binding protein (including, e.g., anti-O1 antigen antibodies or antigen-binding fragments thereof) having least 95, 96, 97, 98, or 99% sequence identity to SEQ ID NOs:8, 9, 12, 13, 21, 22, 30, or 31 differs from SEQ ID NOs: 8, 9, 12, 13, 21, 22, 30, or 31 by conservative amino acid substitutions only. In some embodiments, isolated antigen binding protein (including, e.g., anti-O1 antigen antibodies or antigen-binding fragments thereof) that specifically binds to *K. pneumoniae* O1 antigen, comprises a heavy chain variable region (VH) at least 95, 96, 97, 98, or 99% identical to SEQ ID NOs: 8, 12, 21, or 30 and a light chain variable region (VL) at least 95, 96, 97, 98, or 99% identical to SEQ ID NOs:9, 13, 22, 31, wherein the isolated antigen binding protein (including, e.g., anti-O1 antigen antibodies or antigen-binding fragments thereof) is not antibody clone Ru-O1 (see Rukavina T., et al., *Infect Immun* 65:1754-60 (1997).

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 95% identical to SEQ ID NOs:8 and 9, 12 and 13, 31 and 22, or 30 and 31, respectively, and wherein the antigen binding protein induces OPK of *Klebsiella* (e.g., *K. pneumoniae*), optionally wherein the antigen binding protein does not neutralizes LPS or neutralizes LPS.

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 95% identical to SEQ ID NOs:8 and 9, 12 and 13, 31 and 22, or 30 and 31, respectively, and wherein the antigen binding protein kills *Klebsiella* (e.g., *K. pneumoniae*) as measured by a serum bactericidal assay.

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 95% identical to SEQ ID NOs:8 and 9, 12 and 13, 31 and 22, or 30 and 31, respectively, and wherein the antigen binding protein induces OPK of *Klebsiella* (e.g., *K. pneumoniae*) and kills *Klebsiella* (e.g., *K. pneumoniae*) as measured by a serum bactericidal assay.

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 95% identical to SEQ ID NOs:8 and 9, 12 and 13, 31 and 22, or 30 and 31, respectively, and wherein the antigen binding protein act synergistically with an antibiotic (e.g., meropenem, carbapenems, or colistin).

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 96% identical to SEQ ID NOs:8 and 9, 12 and 13, 31 and 22, or 30 and 31, respectively, and wherein the antigen binding protein induces OPK of *Klebsiella* (e.g., *K. pneumoniae*), optionally wherein the antigen binding protein does not neutralize LPS or neutralizes LPS.

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 96% identical to SEQ ID NOs:8 and 9, 12 and 13, 31 and 22, or 30 and 31, respectively, and wherein the antigen binding protein kills *Klebsiella* (e.g., *K. pneumoniae*) as measured by a serum bactericidal assay.

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 96% identical to SEQ ID NOs:8 and 9, 12 and 13, 31 and 22, or 30 and 31, respectively, and wherein the antigen binding protein induces OPK of *Klebsiella* (e.g., *K. pneumoniae*) and kills *Klebsiella* (e.g., *K. pneumoniae*) as measured by a serum bactericidal assay.

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 96% identical to SEQ ID NOs:8 and 9, 12 and 13, 31 and 22, or 30 and 31, respectively, and wherein the antigen binding protein act synergistically with an antibiotic (e.g., meropenem, carbapenems, or colistin).

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 97% identical to SEQ ID NOs:8 and 9, 12 and 13, 31 and 22, or 30 and 31, respectively, and wherein the antigen binding protein induces OPK of *Klebsiella* (e.g., *K. pneumoniae*), optionally wherein the antigen binding protein does not neutralize LPS or neutralizes LPS.

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 97% identical to SEQ ID NOs:8 and 9, 12 and 13, 31 and 22, or 30 and 31, respectively, and wherein the antigen binding protein kills *Klebsiella* (e.g., *K. pneumoniae*) as measured by a serum bactericidal assay.

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 97% identical to SEQ ID NOs:8 and 9, 12 and 13, 31 and 22, or 30 and 31, respectively, and wherein the antigen binding protein induces OPK of *Klebsiella* (e.g., *K. pneumoniae*) and kills *Klebsiella* (e.g., *K. pneumoniae*) as measured by a serum bactericidal assay.

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 97% identical to SEQ ID NOs:8 and 9, 12 and 13, 31 and 22, or 30 and 31, respectively, and wherein the antigen binding protein act synergistically with an antibiotic (e.g., meropenem, carbapenems, or colistin).

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 98% identical to SEQ ID NOs:8 and 9, 12 and 13, 31 and 22, or 30 and 31, respectively, and wherein the antigen binding protein induces OPK of *Klebsiella* (e.g., *K. pneumoniae*), optionally wherein the antigen binding protein does not neutralize LPS or neutralizes LPS.

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 98% identical to SEQ ID NOs:8 and 9, 12 and 13, 31 and 22, or 30 and 31, respectively, and wherein the antigen binding protein kills *Klebsiella* (e.g., *K. pneumoniae*) as measured by a serum bactericidal assay.

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 98% identical to SEQ ID NOs:8 and 9, 12 and 13, 31 and 22, or 30 and 31, respectively, and wherein the antigen binding protein induces OPK of *Klebsiella* (e.g., *K. pneumoniae*) and kills *Klebsiella* (e.g., *K. pneumoniae*) as measured by a serum bactericidal assay.

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 98% identical to SEQ ID NOs:8 and 9, 12 and 13, 31 and 22, or 30 and 31, respectively, and wherein the antigen binding protein act synergistically with an antibiotic (e.g., meropenem, carbapenems, or colistin).

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 99% identical to SEQ ID NOs:8 and 9, 12 and 13, 31 and 22, or 30 and 31, respectively, and wherein the antigen binding protein induces OPK of *Klebsiella* (e.g., *K. pneumoniae*), optionally wherein the antigen binding protein does not neutralize LPS or neutralizes LPS.

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 99% identical to SEQ ID NOs:8 and 9, 12 and 13, 31 and 22, or 30 and 31, respectively, and wherein the antigen binding protein kills *Klebsiella* (e.g., *K. pneumoniae*) as measured by a serum bactericidal assay.

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 99% identical to SEQ ID NOs:8 and 9, 12 and 13, 31 and 22, or 30 and 31, respectively, and wherein the antigen binding protein induces OPK of *Klebsiella* (e.g., *K. pneumoniae*) and kills *Klebsiella* (e.g., *K. pneumoniae*) as measured by a serum bactericidal assay.

In some embodiments, the disclosure provides an isolated antigen binding protein (including, e.g., anti-O1 antigen antibodies or antigen-binding fragments thereof) that specifically binds to *K. pneumoniae* O1 antigen, wherein said antigen binding protein comprises a VH and VL at least 99% identical to SEQ ID NOs:8 and 9, 12 and 13, 31 and 22, or 30 and 31, respectively, and wherein the antigen binding protein act synergistically with an antibiotic (e.g., meropenem, carbapenems, or colistin).

In some embodiments, the disclosure provides an isolated antigen binding protein (e.g., an anti-O1 antigen antibody or antigen-binding fragment thereof) that binds to *K. pneumoniae, K. oxytoca, K. planticola, K. ozaenae, K. rhinoscleromatis* and/or *K. granulomatis* O1 antigen in addition to *K. pneumoniae* O1 antigen. In some embodiments, the disclosure provides an isolated antigen binding protein (e.g., an anti-O1 antigen antibody or antigen-binding fragment thereof) that binds to *K. pneumoniae, K. oxytoca, K. planticola, K. ozaenae, K. rhinoscleromatis* and/or *K. granulomatis* O1 antigen in addition to *K. pneumoniae* O1 antigen, wherein the isolated antigen binding protein (including, e.g., anti-O1 antigen antibodies or antigen-binding fragments thereof) is not antibody clone Ru-O1 (see Rukavina T., et al., *Infect Immun* 65:1754-60 (1997). The ability of an isolated antigen binding protein to bind to O1 antigen can be examined using methods such as those provided in Trautmann M., et al., *J. Med. Microbiol* 44: 44-51 (1996).

Monoclonal antibodies can be prepared using hybridoma methods, such as those described by Kohler and Milstein (1975) Nature 256:495. Using the hybridoma method, a mouse, hamster, or other appropriate host animal, is immunized to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the *K. pneumoniae* O1 antigen is a humanized antibody. In certain embodiments, such antibodies are used therapeutically to reduce antigenicity and HAMA (human anti-mouse antibody) responses when administered to a human subject. Humanized antibodies can be produced using various techniques known in the art. In certain alternative embodiments, the antibody to *K. pneumoniae* O1 antigen is a human antibody.

Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2008, J. Mol. Bio., 376: 1182-200 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

According to the present disclosure, techniques can be adapted for the production of single-chain antibodies specific to *K. pneumoniae* O1 antigen (see U.S. Pat. No. 4,946,778). In addition, methods can be adapted for the construction of Fab expression libraries (Huse, et al., Science 246:1275-1281 (1989)) to allow rapid and effective identification of monoclonal Fab fragments with the desired specificity for O1 antigen, or fragments thereof. Antibody fragments can be produced by techniques in the art including, but not limited to: (a) a F(ab')2 fragment produced by pepsin digestion of an antibody; (b) a Fab fragment generated by reducing the disulfide bridges of an F(ab')2 fragment, (c) a Fab fragment generated by the treatment of the antibody with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Antigen binding proteins of the present disclosure (including, e.g., anti-O1 antigen antibodies or antigen-binding fragments thereof) can further comprise antibody constant regions or parts thereof. For example, a VL domain can be attached at its C-terminal end to antibody light chain constant domains including human Cκ or Cγ chains. Similarly, an antigen binding protein based on a VH domain can be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG4. For example, the immunoglobulin heavy chain can be derived from the antibody isotype sub-class, IgG1. Any synthetic or other constant region variant that has these properties and stabilizes variable regions is also contemplated for use in embodiments of the present disclosure. The antibody constant region can be an Fc region with a YTE mutation, such that the Fc region comprises the following amino acid substitutions: M252Y/S254T/T256E. This residue numbering is based on Kabat numbering. The YTE mutation in the Fc region increases serum persistence of the antigen-binding protein (see Dall'Acqua, W. F. et al. (2006) The Journal of Biological Chemistry, 281, 23514-23524). The antibody constant region can be an Fc region with an N3 mutation, such that the Fc region comprises the sequence Cys-Ser-Trp-His-Leu-Cys (SEQ ID NO: 68) at positions 432-437 (no insertion between positions 437 and 438) based on Kabat numbering. The N3 mutation in the Fc region also increases serum persistence of the antigen-binding protein. In certain embodiments, the antibody constant region can include a YTE mutation, an N3 mutation, or both YTE and N3 mutations.

In some embodiments herein, the antigen binding protein, e.g., antibody or antigen-binding fragment thereof, is modified to improve effector function, e.g., so as to enhance antigen-dependent cell-mediated cytotoxicity (ADCC) and/or complement dependent cytotoxicity (CDC). This can be achieved by making one or more amino acid substitutions or by introducing cysteine in the Fc region. Variants of the Fc region (e.g., amino acid substitutions and/or additions and/or deletions) that can enhance or diminish effector function of an antibody and/or alter the pharmacokinetic properties (e.g., half-life) of the antibody are disclosed, for example in U.S. Pat. No. 6,737,056B1, U.S. Patent Application Publication No. 2004/0132101A1, U.S. Pat. Nos. 6,194,551, and 5,624,821 and 5,648,260. One particular set of substitutions, the triple mutation L234F/L235E/P331S ("TM"; Kabat numbering) causes a profound decrease in the binding activity of human IgG1 molecules to human C1q, CD64, CD32A and CD16. See, e.g., Oganesyan et al., *Acta Crystallogr D Biol Crystallogr.* 64:700-704 (2008). In other cases it can be that constant region modifications increase serum half-life. The serum half-life of proteins comprising Fc regions can be increased by increasing the binding affinity of the Fc region for FcRn.

When the antigen-binding protein is an antibody or an antigen-binding fragment thereof, it can further comprise a heavy chain immunoglobulin constant domain selected from the group consisting of: (a) an IgA constant domain; (b) an IgD constant domain; (c) an IgE constant domain; (d) an IgG1 constant domain; (e) an IgG2 constant domain; (f) an IgG3 constant domain; (g) an IgG4 constant domain; and (h) an IgM constant domain. In some embodiments, the antigen-binding protein is an antibody or an antigen-binding fragment thereof that comprises an IgG1 heavy chain immunoglobulin constant domain. In some embodiments, the antigen-binding protein is an antibody or an antigen-binding fragment thereof that comprises an IgG1/IgG3 chimeric heavy chain immunoglobulin constant domain.

The antigen-binding protein of the disclosure (including, e.g., anti-O1 antigen antibodies or antigen-binding fragments thereof) can further comprise a light chain immunoglobulin constant domain selected from the group consisting of: (a) an Ig kappa constant domain; and (b) an Ig lambda constant domain.

The antigen-binding protein of the disclosure (including, e.g., anti-O1 antigen antibodies or antigen-binding fragments thereof) can further comprise a human IgG1 constant domain and a human lambda constant domain. The antigen-binding protein of the disclosure (including, e.g., anti-O1 antigen antibodies or antigen-binding fragments thereof) can further comprise a human IgG2 constant domain and a human lambda constant domain.

The antigen-binding protein of the disclosure can comprise an IgG1 Fc domain containing a mutation at positions 252, 254 and 256, wherein the position numbering is according to the EU index as in Kabat. For example, the IgG1 Fc domain can contain a mutation of M252Y, S254T, and T256E, wherein the position numbering is according to the EU index as in Kabat.

The present disclosure also relates to an isolated VH domain of the antigen-binding protein of the disclosure and/or an isolated VL domain of the antigen-binding protein of the disclosure.

Antigen-binding proteins (including antibodies or antigen binding fragments thereof) of the disclosure can be labeled with a detectable or functional label. Detectable labels include radiolabels such as 131I or 99Tc, which may be attached to antibodies of the present disclosure using conventional chemistry known in the art of antibody imaging. Labels also include enzyme labels such as horseradish peroxidase. Labels further include chemical moieties such as biotin which may be detected via binding to a specific cognate detectable moiety, e.g., labeled avidin. Non-limiting examples of other detectable or functional labels which may be attached to the antigen-binding proteins (including antibodies or antigen binding fragments thereof) of the disclosure include: isotopic labels, magnetic labels, redox active moieties, optical dyes, biotinylated groups, fluorescent moieties such as biotin signaling peptides, Green Fluorescent Proteins (GFPs), blue fluorescent proteins (BFPs), cyan fluorescent proteins (CFPs), and yellow fluorescent proteins (YFPs), and polypeptide epitopes recognized by a secondary reporter such as histidine peptide (his), hemagglutinin (HA), gold binding peptide, Flag; a radioisotope, radionuclide, a toxin, a therapeutic and a chemotherapeutic agent.

III. Pharmaceutical Compositions

The disclosure also provides a pharmaceutical composition comprising one or more of the O1-binding agents (including, e.g., anti-O1 antigen antibodies or antigen binding fragments) described herein. In certain embodiments, the pharmaceutical compositions further comprise a pharmaceutically acceptable vehicle or pharmaceutically acceptable excipient. In certain embodiments, these pharmaceutical compositions find use in treating, preventing or ameliorating a condition associated with a *Klebsiella* (e.g., *K. pneumoniae*) infection in human patients. In certain embodiments, these pharmaceutical compositions find use in inhibiting growth of *Klebsiella* (e.g., *K. pneumoniae*). In some embodiments, the *Klebsiella* (e.g., *K. pneumoniae*) is of the O1 serotype. In some embodiments, the pharmaceutical composition comprising one or more of the O1-binding agents (including, e.g., anti-O1 antigen antibodies or antigen binding fragments), does not include antibody clone Ru-O1 (see Rukavina T., et al., *Infect Immun* 65:1754-60 (1997)).

In certain embodiments, formulations are prepared for storage and use by combining an antibody or anti-O1 binding agent described herein with a pharmaceutically acceptable vehicle (e.g., carrier, excipient) (see, e.g., Remington, The Science and Practice of Pharmacy 20th Edition Mack Publishing, 2000, herein incorporated by reference). In some embodiments, the formulation comprises a preservative.

The pharmaceutical compositions of the present disclosure can be administered in any number of ways for either local or systemic treatment.

In some embodiments, a pharmaceutical composition comprising one or more of the O1-binding agents (e.g., anti-O1 antigen antibodies or antigen binding fragments) described herein is used for treating pneumonia, urinary tract infection, septicemia/sepsis, neonatal septicemia/sepsis, diarrhea, soft tissue infection, infection following an organ transplant, surgery infection, wound infection, lung infection, pyogenic liver abscesses (PLA), endophthalmitis, meningitis, necrotizing meningitis, ankylosing spondylitis, or spondyloarthropathies. In some embodiments, a pharmaceutical composition comprising one or more of the O1-binding agents (e.g., anti-O1 antigen antibodies or antigen binding fragments) described herein is useful in nosocomial infections, opportunistic infections, infections following organ transplants, and other conditions associated with a *Klebsiella* infection (e.g. infection with *K. pneumoniae*, *K. oxytoca*, *K. planticola*, *K. ozaenae*, *K. rhinosclermoatis*, and/or *K. granulomatis*). In some embodiments, a pharmaceutical composition comprising one or more of the O1-binding agents (including, e.g., anti-O1 antigen antibodies or antigen binding fragments) described herein is useful in subjects exposed to a *Klebsiella* contaminated device, including, e.g., a ventilator, a catheter, or an intravenous catheter.

In some embodiments, the pharmaceutical composition comprises an amount of an O1-binding agent (e.g., an anti-O1 antigen antibody or antigen-binding fragment thereof) that is effective to inhibit growth of the *Klebsiella* in a subject. In some embodiments, the *Klebsiella* is *K. pneumoniae*, *K. oxytoca*, *K. planticola*, *K. ozaenae*, *K. rhinosclermoatis*, and/or *K. granulomatis*. In some embodiments, the *Klebsiella* is *K. pneumoniae*, *K. oxytoca*, and/or *K. granulomatis*. In some embodiments, the *Klebsiella* is *K. pneumoniae*. In some embodiments, the *Klebsiella* (e.g., *K. pneumoniae*) is of the O1 serotype.

In some embodiments, the methods of treating, preventing and/or ameliorating a condition associated with a *Klebsiella* infection comprises contacting a subject infected with a *Klebsiella* with a pharmaceutical composition comprising an O1-binding agent (e.g., an anti-O1 antigen antibody or antigen-binding fragment thereof) in vivo. In some embodiments, a pharmaceutical composition comprising an O1-binding agent is administered at the same time or shortly after a subject has been exposed to bacteria to prevent infection. In some embodiments, the pharmaceutical composition comprising an O1-binding agent is administered as a therapeutic after infection.

In certain embodiments, the method of treating, preventing, and/or ameliorating *Klebsiella* infections comprises administering to a subject a pharmaceutical composition comprising an O1-binding agent (e.g., an anti-O1 antigen antibody or antigen-binding fragment thereof). In certain embodiments, the subject is a human. In some embodiments, the pharmaceutical composition comprising an O1-binding agent (e.g., an anti-O1 antigen antibody or antigen-binding fragment thereof) is administered before the subject is infected with *Klebsiella*. In some embodiments, the pharmaceutical composition comprising an O1-binding agent (e.g., an anti-O1 antigen antibody or antigen-binding fragment thereof) is administered after the subject is infected with a *Klebsiella*.

In certain embodiments, the pharmaceutical composition comprising an O1-binding agent (e.g., an anti-O1 antigen antibody or antigen-binding fragment thereof) is administered to a subject on a ventilator. In certain embodiments, the subject has a catheter (e.g., a urinary catheter or an intravenous catheter). In certain embodiments, the subject is receiving antibiotics (e.g., meropenem, carbapenems, fluoroquinolone, tetracycline, chloramphenicol, trimethoprim, sulfonamide, and/or colistin).

In certain embodiments, a pharmaceutical composition comprising an O1-binding agent (e.g., an anti-O1 antigen antibody or antigen-binding fragment thereof) is for the treatment or prevention of a nosocomial *Klebsiella* infection. In certain embodiments, a pharmaceutical composition comprising an O1-binding agent (e.g., an anti-O1 antigen antibody or antigen-binding fragment thereof) is for the treatment or prevention of an opportunistic *Klebsiella* infection. In certain embodiments, a pharmaceutical composition comprising an O1-binding agent (e.g., an anti-O1 antigen antibody or antigen-binding fragment thereof) is for the treatment or prevention of a *Klebsiella* infection following an organ transplant.

In certain embodiments, a pharmaceutical composition comprising an O1-binding agent (e.g., an anti-O1 antigen antibody or antigen-binding fragment thereof) is for the treatment or prevention of a *Klebsiella* infection, wherein the *Klebsiella* is an extended spectrum beta-lactamase (ESBL) producing *Klebsiella*. In certain embodiments, a pharmaceutical composition comprising an O1-binding agent (e.g., an anti-O1 antigen antibody or antigen-binding fragment thereof) is for the treatment or prevention of a *Klebsiella* infection, wherein the *Klebsiella* is a non-extended spectrum beta-lactamase (ESBL) producing *Klebsiella*. In certain embodiments, a pharmaceutical composition comprising an O1-binding agent (e.g., an anti-O1 antigen antibody or antigen-binding fragment thereof) is for the treatment or prevention of a *Klebsiella* infection, wherein the *Klebsiella* is a *Klebsiella pneumoniae* carbapenem resistant enterobacteriaceae (CRE) *Klebsiella*. In certain embodiments, a pharmaceutical composition comprising an O1-binding agent (e.g., an anti-O1 antigen antibody or antigen-binding fragment thereof) is for the treatment or prevention of a *Klebsiella* infection, wherein the *Klebsiella* is a *Klebsiella pneumoniae* carbapenemase (KPC) producing *Klebsiella*.

In certain embodiments, a pharmaceutical composition comprising an O1-binding agent (e.g., an anti-O1 antigen antibody or antigen-binding fragment thereof) is for the treatment or prevention of a cephalosporin resistant *Klebsiella* infection. In certain embodiments, a pharmaceutical composition comprising an O1-binding agent (e.g., an anti-O1 antibody or antigen-binding fragment thereof) is for the treatment or prevention of an aminoglycoside resistant *Klebsiella* infection. In certain embodiments, a pharmaceutical composition comprising an O1-binding agent (e.g., an anti-O1 antigen antibody or antigen-binding fragment thereof) is for the treatment or prevention of a quinolone resistant *Klebsiella* infection. In certain embodiments, a pharmaceutical composition comprising an O1-binding agent (e.g., an anti-O1 antigen antibody or antigen-binding fragment thereof) is for the treatment or prevention of a carbapenem resistant *Klebsiella* infection. In certain embodiments, a pharmaceutical composition comprising an O1-binding agent (e.g., an anti-O1 antigen antibody or antigen-binding fragment thereof) is for the treatment or prevention of a colistin resistant *Klebsiella* infection. In certain embodiments, a pharmaceutical composition comprising an O1-binding agent (e.g., an anti-O1 antigen antibody or antigen-binding fragment thereof) is for the treatment or prevention of a cephalosporin, aminoglycoside, quinolone, fluoroquinolone, tetracycline, chloramphenicol, trimethoprim, sulfonamide, carbapenem, and colistin resistant *Klebsiella* infection. In certain embodiments, a pharmaceutical composition comprising an O1-binding agent (e.g., an anti-O1 antigen antibody or antigen-binding fragment thereof) is for the treatment or prevention of an infection with a *Klebsiella* that is susceptible to antibiotics.

For the treatment, prevention and/or amelioration of a condition associated with a *Klebsiella* infection, the appropriate dosage of a pharmaceutical composition, antibody, or anti-O1 binding agent described herein depends on the type of condition, the severity and course of the condition, the responsiveness of the condition, whether the pharmaceutical composition, antibody, or anti-O1 binding agent is administered for therapeutic or preventative purposes, previous therapy, patient's clinical history, and so on all at the discretion of the treating physician. The pharmaceutical composition, antibody, or anti-O1 binding agent can be administered one time or over a series of treatments lasting from several days to several months, or until a cure is effected or a diminution of the condition is achieved. Optimal dosing schedules can be calculated from measurements of drug accumulation in the body of the patient and will vary depending on the relative potency of an individual antibody or agent. The administering physician can easily determine optimum dosages, dosing methodologies and repetition rates.

IV. Methods of Use

The O1-binding agents (including anti-O1 antigen antibodies and antigen-binding fragments thereof) described herein are useful in a variety of applications including, but not limited to, pneumonia, urinary tract infection, septicemia/sepsis, neonatal septicemia/sepsis, diarrhea, soft tissue infection, infection following an organ transplant, surgery infection, wound infection, lung infection, pyogenic liver abscesses (PLA), endophthalmitis, meningitis, necrotizing meningitis, ankylosing spondylitis, and spondyloarthropathies. In some embodiments, the O1-binding agents (including anti-O1 antigen antibodies and antigen-binding fragments thereof) described herein are useful in nosocomial infections, opportunistic infections, infections following organ transplants, and other conditions associated with a *Klebsiella* infection (e.g. infection with *K. pneumoniae, K. oxytoca, K. planticola, K. ozaenae, K. rhinoscleromatis*, and/or *K. granulomatis*). In some embodiments, the O1-binding agents (including anti-O1 antigen antibodies and antigen-binding fragments thereof) described herein are useful in subjects exposed to a *Klebsiella* contaminated device, including, e.g., a ventilator, a catheter, or an intravenous catheter.

In some embodiments, the disclosure provides methods of treating, preventing and/or ameliorating a condition associated with a *Klebsiella* infection comprising administering an effective amount of an O1-binding agent (e.g., an anti-O1 antigen antibody or antigen-binding fragment thereof) to a subject. In some embodiments, the amount is effective to inhibit growth of the *Klebsiella* in the subject. In some embodiments, the *Klebsiella* is *K. pneumoniae, K. oxytoca, K. planticola, K. ozaenae, K. rhinosclermoatis*, and/or *K. granulomatis*. In some embodiments, the *Klebsiella* is *K. pneumoniae, K. oxytoca*, and/or *K. granulomatis*. In some embodiments, the *Klebsiella* is *K. pneumoniae*. In some embodiments, the *Klebsiella* (e.g., *K. pneumoniae*) is of the O1 serotype. In some embodiments, the subject has been exposed to *Klebsiella*. In some embodiments, *Klebsiella* has been detected in the subject. In some embodiments, the subject is suspected of being infected with *Klebsiella*, e.g., based on symptoms.

In some embodiments, the disclosure further provides methods of inhibiting growth of *Klebsiella* comprising administering an O1-binding agent (e.g., an anti-O1 antigen antibody or antigen-binding fragment thereof) to a subject. In some embodiments, the *Klebsiella* is *K. pneumoniae, K. oxytoca, K. planticola, K. ozaenae, K. rhinosclermoatis*, and/or *K. granulomatis*. In some embodiments, the *Klebsiella* is *K. pneumoniae, K. oxytoca*, and/or *K. granulomatis*. In some embodiments, the *Klebsiella* is *K. pneumoniae*. In some embodiments, the *Klebsiella* (e.g., *K. pneumoniae*) is of the O1 serotype. In some embodiments, the subject has been exposed to *Klebsiella*. In some embodiments, *Klebsiella* has been detected in the subject. In some embodiments, the subject is suspected of being infected with a *Klebsiella*, e.g., based on symptoms.

In some embodiments, the methods of treating, preventing and/or ameliorating a condition associated with a *Klebsiella* infection comprises contacting a subject infected with a *Klebsiella* with the O1-binding agent (e.g., an anti-O1 antigen antibody or antigen-binding fragment thereof) in vivo. In certain embodiments, contacting a cell with an O1-binding agent is undertaken in an animal model. For example, O1-binding agents can be administered to murine *Klebsiella* infection models to reduce bacterial burden. In some embodiments, the O1-binding agent (e.g., an anti-O1 antigen antibody or antigen-binding fragment thereof) is administered before introduction of bacteria to the animal to prevent infections. In some embodiments, the O1-binding agent (e.g., an anti-O1 antigen antibody or antigen-binding fragment thereof) is administered at the same time or shortly after the animal has been exposed to bacteria to prevent infection. In some embodiments, the O1-binding agent (e.g., an anti-O1 antigen antibody or antigen-binding fragment thereof) is administered as a therapeutic after infection. In some embodiments, the methods of treating, preventing and/or ameliorating a condition associated with a *Klebsiella* infection comprises contacting a subject infected with a *Klebsiella* with the O1-binding agent (e.g., an anti-O1 antigen antibody or antigen-binding fragment thereof) in vivo, wherein the isolated antigen binding protein (including, e.g., anti-O1 antigen antibodies or antigen-binding fragments thereof) is not antibody clone Ru-O1 (see Rukavina T., et al., *Infect Immun* 65:1754-60 (1997).

In certain embodiments, the method of treating, preventing, and/or ameliorating *Klebsiella* infections comprises administering to a subject an effective amount of an O1-binding agent (e.g., an anti-O1 antigen antibody or antigen-binding fragment thereof). In certain embodiments, the subject is a human. In some embodiments, the effective amount of an O1-binding agent (e.g., an anti-O1 antigen antibody or antigen-binding fragment thereof) is administered before the subject is infected with *Klebsiella*. In some embodiments, the effective amount of an O1-binding agent (e.g., an anti-O1 antigen antibody or antigen-binding fragment thereof) is administered after the subject is infected with a *Klebsiella*.

In certain embodiments, the subject is on a ventilator. In certain embodiments, the subject has a catheter (e.g., a urinary catheter or an intravenous catheter). In certain embodiments, the subject is receiving antibiotics (e.g., meropenem, carbapenems, or colistin).

In certain embodiments, the *Klebsiella* infection is a nosocomial infection. In certain embodiments, the *Klebsiella* infection is an opportunistic infection. In certain embodiments, the *Klebsiella* infection follows an organ transplant.

In certain embodiments, the *Klebsiella* is an extended spectrum beta-lactamase (ESBL) producing *Klebsiella*. In certain embodiments, the *Klebsiella* is a non-ESBL producing *Klebsiella*. In certain embodiments, the *Klebsiella* is a *Klebsiella pneumoniae* carbapenemase (KPC) producing *Klebsiella*. In certain embodiments, the *Klebsiella* is a *Klebsiella pneumoniae* carbapenem resistant enterobacteriaceae (CRE) *Klebsiella*.

In certain embodiments, the *Klebsiella* is cephalosporin resistant. In certain embodiments, the *Klebsiella* is aminoglycoside resistant. In certain embodiments, the *Klebsiella* is quinolone resistant. In certain embodiments, the *Klebsiella* is carbapenem resistant. In certain embodiments, the *Klebsiella* is cephalosporin, aminoglycoside, quinolone, and carbapenem resistant. In certain embodiments, the *Klebsiella* is cephalosporin, aminoglycoside, and quinolone resistant. In certain embodiments, the *Klebsiella* is susceptible to antibiotics.

In certain embodiments, the method of treating, preventing, and/or ameliorating *Klebsiella* infections comprises administering to a subject an effective amount of an O1-binding agent (e.g., an anti-O1 antigen antibody or antigen-binding fragment thereof) and an antibiotic. The O1-binding agent (e.g., an anti-O1 antigen antibody or antigen-binding fragment thereof) and the antibiotic can be administered simultaneously or sequentially. The O1-binding agent (e.g., an anti-O1 antigen antibody or antigen-binding fragment thereof) and the antibiotic can be administered in the same pharmaceutical composition. The O1-binding agent (e.g., an anti-O1 antigen antibody or antigen-binding fragment thereof) and the antibiotic can be administered in separate pharmaceutical compositions simultaneously or sequentially. In certain embodiments, the antibiotic is an antibiotic suitable to treat a *Klebsiella* infection. In certain embodiments, the antibiotic is meropenem. In certain embodiments, the antibiotic is a carbapanem or colistin. In certain embodiments, the antibiotic is a cephalosporin, aminoglycoside, quinolone, fluoroquinolone, tetracycline, chloramphenicol, trimethoprim, sulfonamide, carbapenem, and/or colistin.

The present disclosure also provides methods of detecting O1 lipopolysaccharide or *Klebsiella* containing O1 antigen. In some embodiments, a method of detecting O1 or *Klebsiella* containing O1 antigen comprises contacting a sample with an O1 binding agent (e.g., an anti-O1 antigen antibody or antigen-binding fragment thereof) provided herein and assaying for binding of the binding agent (e.g., an antibody or antigen-binding fragment thereof) to the sample. Methods of assessing binding are well known in the art. In some embodiments, the methods comprise detecting O1 lipopolysaccharide or *Klebsiella* containing O1 antigen. In some embodiments, a method of detecting O1 or *Klebsiella* containing O1 comprises contacting a sample with an O1 binding agent (e.g., an anti-O1 antigen antibody or antigen-binding fragment thereof) provided herein and assaying for binding of the binding agent (e.g., an antibody or antigen-binding fragment thereof) to the sample.

V. Kits

A kit comprising an isolated antigen-binding protein (e.g. an anti-O1 antigen antibody or antigen-binding fragment thereof) according to any aspect or embodiment of the present disclosure is also provided as an aspect of the present disclosure. In a kit, the antigen-binding protein, antibody, or antigen-binding fragment thereof can be labeled to allow its reactivity in a sample to be determined, e.g., as described further below. Components of a kit are generally sterile and in sealed vials or other containers. Kits can be employed in diagnostic analysis or other methods for which antibodies are useful. A kit can contain instructions for use of the components in a method, e.g., a method in accordance with the present disclosure. Ancillary materials to assist in or to enable performing such a method may be included within a kit of the disclosure.

The reactivity of antibodies or antigen-binding fragments thereof in a sample can be determined by any appropriate means. Radioimmunoassay (RIA) is one possibility. Radioactive labeled antigen is mixed with unlabeled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay can also be used with non-radioactive antigen, using antigen or an analogue linked to a reporter molecule. The reporter molecule can be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules can be enzymes which catalyze reactions that develop or change colors or cause changes in electrical properties, for example. They can be molecularly excitable, such that electronic transitions between energy states result in characteristic spectral absorptions or emissions. They can include chemical entities used in conjunction with biosensors. Biotin/avidin or biotin/streptavidin and alkaline phosphatase detection systems can be employed.

The signals generated by individual antibody-reporter conjugates can be used to derive quantifiable absolute or relative data of the relevant antibody binding in samples (normal and test).

The present disclosure also provides the use of an antigen-binding protein as described above for measuring antigen levels in a competition assay, including methods of measuring the level of O1 antigen or *Klebsiella* containing O1 antigen in a sample by employing an antigen-binding protein provided by the present disclosure in a competition assay. In some embodiments, the physical separation of bound from unbound antigen is not required. In some embodiments, a reporter molecule is linked to the antigen-binding protein so that a physical or optical change occurs on binding. The reporter molecule can directly or indirectly generate detectable, and preferably measurable, signals. In some embodiments, the linkage of reporter molecules is direct or indirect, or covalent, e.g., via a peptide bond or non-covalent interaction. Linkage via a peptide bond can be as a result of recombinant expression of a gene fusion encoding antibody and reporter molecule.

The present disclosure also provides methods of measuring levels of O1 antigen directly, by employing an antigen-binding protein (e.g. an anti-O1 antigen antibody or antigen-binding fragment thereof) according to the disclosure. In some embodiments, these methods utilize a biosensor system. In some embodiments, the methods comprise detecting O1 antigen by employing an antigen-binding protein (e.g., an anti-O1 antigen antibody or antigen-binding fragment thereof) according to the disclosure.

VI. Polynucleotides and Host Cells

In further aspects, the present disclosure provides an isolated nucleic acid comprising a nucleic acid sequence encoding an antigen-binding protein (e.g. an anti-O1 antigen antibody or antigen-binding fragment thereof), VH domain and/or VL domain according to the present disclosure. In some aspects the present disclosure provides methods of making or preparing an antigen-binding protein (e.g. an anti-O1 antigen antibody or antigen-binding fragment thereof), a VH domain and/or a VL domain described herein, comprising expressing said nucleic acid under conditions to bring about production of said antigen-binding protein, VH domain and/or VL domain and, optionally, recovering the antigen-binding protein, VH domain and/or VL domain.

A nucleic acid provided by the present disclosure includes DNA and/or RNA. In one aspect, the nucleic acid is cDNA. In one aspect, the present disclosure provides a nucleic acid which codes for a CDR or set of CDRs or VH domain or VL domain or antibody antigen-binding site or antibody, e.g., scFv, IgG1, or IgG2, as described above (see, e.g., Tables 1-4).

One aspect of the present disclosure provides a nucleic acid, generally isolated, optionally a cDNA, encoding a VH CDR or VL CDR sequence described herein. In some embodiments, the VH CDR is selected from SEQ ID NOs: 1-3, 14-16, and 23-25. In some embodiments, the VL CDR is selected from SEQ ID NOs: 4-7, 10, 11, 17-20, and 26-29. A nucleic acid encoding the KPE33, KPE33V2016, KPA27, KPB202, KBJ4, or 54H7 set of HCDRs and nucleic acid encoding the KPE33, KPE33V2016, KPA27, KPB202, KBJ4, or 54H7 set of LCDRs are also provided, as are nucleic acids encoding individual CDRs, HCDRs, LCDRs and sets of CDRs, HCDRs, LCDRs as described in Tables 1 and 2. In some embodiments, the nucleic acids of the present disclosure encode a VH and/or VL domain of KPE33, KPE33V2016, KPA27, KPB202, KBJ4, or 54H7 as described in Tables 3 and 4.

The invention further provides a polynucleotide comprising a sequence selected from those shown in Tables 5 and 6 below.

TABLE 5

Variable heavy chain polynucleotide sequences.

| Antibody | VH Polynucleotide Sequence (SEQ ID NO) |
| --- | --- |
| KPA27 | CAGGTGCAGCTGGTGCAGTCTGGGGCTGAGGTGAAGAA<br>ACCTGGGGCCTCAGTGAAGGTCTCCTGCAAGGCTTCTG<br>AAAACACCTTCAACGACTTCTATATGCACTGGGTGCGA<br>CAGGCCCCTGGACAAGGGCTTGAGTGGATGGGATGGAT<br>CCACCCTGACGGTGTTGTCACAAACTATGCACAGAAAT<br>TTCAGGGCAGGGTCACTATGACCAGGGACACGTCCATC<br>AACACAGTCTACATGGAATTGAACGGCCTGATCTCTGA<br>CGACACGGCCGTGTATTACTGTATGAGAGACGGGCCAG<br>GATCAGAAGGTTCCTGGTTTGACTATTGGGGCCAGGGA<br>ACCCTGGTCACCGTCTCCTCAG<br>(SEQ ID NO: 49) |
| KPB202 | GAGGTGCAGCTGGTGGAGTCTGGGGGAGGCTTGGTCCA<br>GCCTGGGGGGTCCCTGAGCCTCTCCTGTGCAGCCTCTG<br>GATTCACCTTTAGTAACTTTTGGGTGGGCTGGGGCCGC<br>CAGGCTCCAGGGAAGGGCCTGGAGTGGGTGGCCAATAT<br>AAACCCAGATGAAGTGAGAAATACTATGTGGACTCTG<br>TGAAGGGCCGAGTCACCATCTCCAGAGACAACGCCAAG<br>AACTCACTGTCTCTGCAAATGAACAGCCTGAGAGTCGA<br>GGACGCGGCTGTGTACTACTGTGCGAGACTAGGGCCGT<br>TCCATCCTGACTGCTGGGGCCAGGGAACCCTGGTCACC<br>GTCTCCTCAG<br>(SEQ ID NO: 51) |
| KPJ4 | CAGGTACAGCTGCAGCAGTCAGGTCCAGGACTGGTGAG<br>GCCCTCGCAGACCCTCTCACTCACCTGTGCCATCTCCG<br>GGGACAGTGTCTCTAGCAACACTGCTGCTTGGAACTGG<br>ATCAGGCAGTCCCCATCGAGAGGCCTTGAGTGGCTGGG<br>AAGGACATATTACAGGTCCGAGTGGTATAATGATTATG<br>CAGTATCTGTGAAAAGTCGAATAACCATCAACCCAGAC<br>ACATCCAAGAACCAGTTCTCCCTGCAGTTGAACTCTGT<br>GACTCCCGAGGACACGGCTGTGTATTACTGTGCAAGAA<br>TTTCCTGGAACGACCTCCCAGCTTGGGGCCAGGGAACC<br>CTGGTCACCGTCTCCTCAG<br>(SEQ ID NO: 53) |
| KPE33 | GAAGTGCAGCTGGTGGAGTCTGGGGGGGCCTTGGTACA<br>GCCTGGCGGGTCCCTGAGACTCTCGTGTGCAGTTTCTG<br>GATTCATCTTTGATGATTATGCCATCCACTGGGTCCGG<br>CGAGCTCCAGGGAAGGGCCTGGAGTGGGTCTCAGGCAT<br>TGCTTGGAAGAGTGGTGCCACAAACTATGCGGACTCTG<br>TGAAGGGCCGCTTCGCCATCTCTAGAGACAACTCCAAG<br>AAATCTATGTATCTACAAATGAACAGTCTGGGAACTGA<br>AGACACGGCCTTGTATTACTGTACAAGACGACGGGCGT<br>CTGGGGATGATACTTTTTATTACTTTGACTATTGGGGT<br>CAGGGAACCCTGGTCACCGTCTCCTCA<br>(SEQ ID NO: 55) |
| KPE33V2016 | GAGGTGCAGCTGGTCGAATCCGGCGGGGACTGGTGCA<br>GCCTGGCCGCTCTCGAGACTGAGCTGCGCCGCTTCCG<br>GGTTCATCTTTGACGATTACGCTATGCACTGGGTGCGG<br>CAGGCACCTGGCAAGGGACTGGAGTGGGTCTCTGGGAT<br>CGCCTGGAAAAGTGGAGCAACCAACTACGCCGACTCAG<br>TGAAGGGGAGATTCGCCATTAGCCGGGATAACTCCAAG<br>AAAAGTATGTATCTGCAGATGAATTCCCTGGGAACCGA<br>AGACACAGCCCTGTACTATTGTACACGGAGAAGGGCTT<br>CTGGCGACGATACTTTCTACTATTTTGATTATTGGGGA<br>CAGGGCACTCTGGTGACCGTCAGCTCC<br>(SEQ ID NO: 57) |
| KPE33-<br>H32 +<br>L2016<br>(E1Q) | CAGGTGCAGCTCGTGGAGTCCGGCGGTGGCCTGGTTCA<br>GCCTGGCCGCTCTCTTAGACTGAGTTGCGCCGCTAGCG<br>GTTTTATTTTCGACGACTATGCGATCCACTGGGTTAGA<br>CAAGCACCAGGAAAGGGACTTGAATGGGTTTCTGGGAT<br>TGCGTATAAATCAGGGGCCACGAACTACGCTGAGAGCG<br>TTAAGGGGCGATTTACTATAAGCAGGGATCAGTCCAAA<br>AACTCACTGTACTTGCAGATGAACTCACTCAGAGCCGA<br>GGACACGGCGTTGTACTACTGCACACGAAGGAGGGCAT<br>CAGGAGATAATACCTTTTATTCTTCGACTACTGGGGC<br>CAAGGCACGTTGGTAACGGTGAGTTCT<br>(SEQ ID NO: 64) |
| KPE33-<br>H33 +<br>L2016<br>(E1Q) | CAGGTGCAGCTCGTGGAGTCCGGCGGTGGCCTGGTTCA<br>GCCTGGCCGCTCTCTTAGACTGAGTTGCGCCGCTAGCG<br>GTTTTATTTTCGACGACTATGCGATCCACTGGGTTAGA<br>CAAGCACCAGGAAAGGGACTTGAATGGGTTTCTGGGAT |

TABLE 5-continued

Variable heavy chain polynucleotide sequences.

| Antibody | VH Polynucleotide Sequence (SEQ ID NO) |
| --- | --- |
| | TGCGTATAAATCAGGGGCCACGAACTACGCTGAGAGCG<br>TTAAGGGGCGATTTACTATAAGCAGGGATCAGTCCAAA<br>AAGTCACTGTACTTGCAGATGAACTCACTCAGAGCCGA<br>GGACACGGCGTTGTACTACTGCACACGAAGGAGGGCAT<br>CAGGAGATAATACCTTTTATTCTTCGACTACTGGGGC<br>CAAGGCACGTTGGTAACGGTGAGTTCT<br>(SEQ ID NO: 65) |

TABLE 6

Variable light chain polynucleotide sequences.

| Antibody | VL Polynucleotide Sequence (SEQ ID NO) |
| --- | --- |
| KPA27 | GACATCCAGATGACCCAGTCTCCTTCCACCCTGTCTGC<br>ATCTGTAGGAGACAGAGTCACCATCACTTGCCGGGCCA<br>GTCAGCCTGTTAGTAATAGATTGGCCTGGTATCAGCAG<br>AAACCAGGGAAGCCCCTACACTCCTGATCTACAAGGC<br>GTCTACTTTACAAAGTGGGGTCCCATTAAGGTTCAGCG<br>GCAGTGGATCTGGGACAGAGTTCACTCTCACCATCAGC<br>AGCCTGCAGTCTGATGATTTTGCAACTTATTACTGCCA<br>ACAGTCTCAGACCTTCGGCCAAGGGACCAAGGTGGAAA<br>TCAAAC<br>(SEQ ID NO: 50) |
| KPB202 | GATGTTGTGATGACTCAGTCTCCACTCTCCCTGCCCGT<br>CACCCTTGGACAGCCGGCTCCATCTCCTGCAGGTCTA<br>GTCAAAGCCTCGTACACAGTGATGGAAACACCTACTTG<br>AATTGGTTTCAGCAGAGGCCAGGCCAATCTCCAAGGCG<br>CCTAATTTATGAGGTTTCTAACCGGGACTCTGGGGTCC<br>CAGACAGATTCAGCGGCAGTGGGTCAGGCACTGATTTC<br>ACACTGAAAATCAGCAGGGTGGAGGCTGAGGATATTGG<br>GGTTTATTACTGCATGCAAGGAACACACTGGCCGTGGA<br>CGTTCGGCCAAGGGACCAAGGTGGAAATCAAAC<br>(SEQ ID NO: 52) |
| KPJ4 | GACATCGTGATGACCCAGTCTCCAGACTCCCTGGCTGT<br>GTCTCTGGGCGAGAGGGCCACTATCAACTGCAAGTCCA<br>GCCAGAGTATTTTATACAGCTCCCACAATAAGAACTAC<br>TTAGCTTGGTACCAGCAGAAACCAGGACAGCCTCCTAA<br>GGTGCTCATTTACTGGGCGTCTACCCGGGAATCCGGGG<br>TCCCTGACCGATTCAGTGGCAGCGGGTCTGGGACAGAT<br>TTCACTCTCACCATCAGCAACCTGCAGGCTGAAGATGT<br>GGCAGTTTATTACTGTCAGCAGTATTGTAATATCCCGT<br>ACACTTTTGGCCAGGGGACCAAGCTGGAGATCAAAC<br>(SEQ ID NO: 54) |
| KPE33 | GAAATTGTGTTGACACAGTCTCCAGCCACCCTGTCTTT<br>GTCTCCAGGAGAAAGAGCCACCCTCTCCTGCAGGGCCA<br>GTCAGAATGTTAATACCAACTTAGCCTGGTACCAGCAG<br>CGACCTGGACAGTCTCCCAGACTCCTCATTTATGATGC<br>ATCCACCAGGGCCGCTGGCCTCCCAGCCAGGTTCAGTG<br>GCAGTGGGTCTGGGACAGACTTCACTCTCACCATCAGC<br>AGCCTAGAGCCTGAAGATTTTGCAGTCTACTATTGTCA<br>GCAGTGTACCAACTGGCGGTACACTTTTGGCCAGGGGA<br>CCAAGCTGGAGATCAAA<br>(SEQ ID NO: 56) |
| KPE33V2016 | GAGATCGTGCTGACACAGTCCCCAGCCACTCTGTCTCT<br>GAGTCCCGGGGAACGGGCAACTCTGTCTTGCAGGGCCA<br>GTCAGAACGTCAATACCAACCTGGCTTGGTACCAGCAG<br>AAGCCCGGACAGGCACCTCGACTGCTGATCTATGACGC<br>CAGCAATAGGGCTACAGGCATTCCAGCACGCTTCTCAG<br>GATCTGGATCTGGAACGGACTTTACTCTGACCATCAGC<br>TCCCTGGAGCCCGAAGATTTCGCCGTGTACTATTGTCA<br>GCAGACCACAAACTGGAGATACACCTTTGGCCAGGGGA<br>CAAAGCTGGAGATCAAG<br>(SEQ ID NO: 58) |
| KPE33-<br>H32 +<br>L2016<br>(E1Q) | CAGATTGTGTTGACGCAGAGTCCCGCGACACTTAGCCT<br>CTCTCCCGGAGAGAGAGCGACGCTTAGTTGCCGAGCAT<br>CCCAGAACGTCAACACTAATCTCGCGTGGTATCAGCAG<br>AAGCCGGGCCAAGCCCCCAGGCTGTTGATTTACGACGC |

TABLE 6-continued

Variable light chain polynucleotide sequences.

| Antibody | VL Polynucleotide Sequence (SEQ ID NO) |
| --- | --- |
|  | TAGTAACCGCGCCACAGGAATCCCGGCAAGATTTAGTG<br>GGTCAGGATCAGGAACTGACTTTACCTTGACGATAAGT<br>AGTCTGGAACCAGAAGATTTCGCCGTATATTACTGTCA<br>ACAGACAACAAACTGGCGCTACACCTTCGGCCAAGGAA<br>CAAAACTTGAGATCAAG<br>(SEQ ID NO: 66) |
| KPE33-<br>H33 +<br>L2016<br>(E1Q) | CAGATTGTGTTGACGCAGAGTCCCGCGACACTTAGCCT<br>CTCTCCCGGAGAGAGAGCGACGCTTAGTTGCCGAGCAT<br>CCCAGAACGTCAACACTAATCTCGCGTGGTATCAGCAG<br>AAGCCGGGCCAAGCCCCCAGGCTGTTGATTTACGACGC<br>TAGTAACCGCGCCACAGGAATCCCGGCAAGATTTAGTG<br>GGTCAGGATCAGGAACTGACTTTACCTTGACGATAAGT<br>AGTCTGGAACCAGAAGATTTCGCCGTATATTACTGTCA<br>ACAGACAACAAACTGGCGCTACACCTTCGGCCAAGGAA<br>CAAAACTTGAGATCAAG<br>(SEQ ID NO: 67) |

Also provided is a polynucleotide having at least about 95%, at least about 96%, at least about 97%, at least about 98%, or at least about 99% sequence identity to any one of the SEQ ID NOs provided in Table 5 or 6. Thus, in certain embodiments, the polynucleotide comprises (a) a polynucleotide having at least about 95% sequence identity to any one of the SEQ ID NOs provided in Table 5, and/or (b) a polynucleotide having at least about 95% sequence identity to any one of the SEQ ID NOs provided in Table 6. In certain embodiments, the polynucleotide comprises: (a) a polynucleotide having the sequence of a SEQ ID NO provided in Table 5; and/or (b) a polynucleotide having the sequence of a SEQ ID NO provided in Table 6.

The present disclosure provides an isolated polynucleotide or cDNA molecule sufficient for use as a hybridization probe, PCR primer or sequencing primer that is a fragment of a nucleic acid molecule disclosed herein or its complement. The nucleic acid molecule can, for example, be operably linked to a control sequence.

The present disclosure also provides constructs in the form of plasmids, vectors, transcription or expression cassettes which comprise at least one polynucleotide as described above (see e.g., Tables 5 and 6).

The present disclosure also provides a recombinant host cell which comprises one or more nucleic acids, plasmids, vectors or as described above (see e.g., Tables 5 and 6). A nucleic acid encoding any CDR or set of CDRs or VH domain or VL domain or antibody antigen-binding site, antibody, e.g. scFv, IgG1, or IgG2 as provided (see, e.g., Tables 1-4) itself forms an aspect of the present disclosure, as does a method of production of the encoded product, which method comprises expression from the nucleic acid encoding the product (e.g. the antigen binding protein, including, e.g., an anti-O1 antigen antibody or antigen-binding fragment thereof, disclosed herein). Expression can conveniently be achieved by culturing under appropriate conditions recombinant host cells containing a nucleic acid described herein. Following production by expression a CDR, set of CDRs, VH or VL domain, an antigen-binding protein can be isolated and/or purified using any suitable technique.

In some instances, the host cell is a mammalian host cell, such as a HEK293 cell, a HeLa cell, NS0 murine myeloma cell, a PER.C6® human cell, or a Chinese hamster ovary (CHO) cell.

Antigen-binding proteins, VH and/or VL domains and encoding nucleic acid molecules and vectors can be isolated and/or purified, e.g., from their natural environment, in substantially pure or homogeneous form, or, in the case of nucleic acid, free or substantially free of nucleic acid or genes origin other than the sequence encoding a polypeptide with the required function. Nucleic acids according to the present disclosure can comprise DNA or RNA and can be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, plant cells, yeast and baculovirus systems and transgenic plants and animals. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others. A common bacterial host is *E. coli*.

The expression of antibodies and antibody fragments in prokaryotic cells such as *E. coli* is well established in the art. For a review, see for example Plückthun, A. Bio/Technology 9: 545-551 (1991). Expression in eukaryotic cells in culture is also available to those skilled in the art as an option for production of an antigen-binding protein for example Chadd H E and Chamow S M (2001) 110 Current Opinion in Biotechnology 12: 188-194, Andersen D C and Krummen L (2002) Current Opinion in Biotechnology 13: 117, Larrick J W and Thomas D W (2001) Current opinion in Biotechnology 12:411-418.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 3rd edition, Sambrook and Russell, 2001, Cold Spring Harbor Laboratory Press. Many known techniques and protocols for manipulation of nucleic acids, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1988, *Short Protocols in Molecular Biology: A Compendium of Methods from Current Protocols in Molecular Biology*, Ausubel et al. eds., John Wiley & Sons, 4$^{th}$ edition 1999. The disclosures of Sambrook et al. and Ausubel et al. (both) are incorporated herein by reference.

Thus, a further aspect of the present disclosure provides a host cell containing nucleic acid as disclosed herein. For example, the disclosure provides a host cell transformed with nucleic acid comprising a nucleotide sequence (see e.g., Tables 5 and 6) encoding an antigen-binding protein of the present disclosure or antibody CDR, set of CDRs, or VH and/or VL domain of an antigen-binding protein of the present disclosure (see, e.g., Tables 1-4). In some embodiments, the host cell comprises the expressed antigen-binding protein of the present disclosure or antibody CDR, set of CDRs, or VH and/or VL domain of an antigen-binding protein of the present disclosure (see, e.g., Tables 1-4).

Such a host cell can be in vitro and can be in culture. Such a host cell can be an isolated host cell. Such a host cell can be in vivo.

A still further aspect provided herein is a method comprising introducing such nucleic acid into a host cell. The introduction can employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. Introducing nucleic acid in the host cell, in particular a eukaryotic cell can use a viral or a plasmid based system. The plasmid system can be maintained episomally or may incorporated into the host cell or into an artificial chromosome. Incorporation can be either by random or targeted integration of one or more copies at single or multiple loci. For bacterial cells, suitable techniques may include calcium chloride transformation, electroporation, and transfection using bacteriophage.

The introduction can be followed by causing or allowing expression from the nucleic acid, e.g., by culturing host cells under conditions for expression of the gene.

In one embodiment, the nucleic acid of the present disclosure is integrated into the genome (e.g. chromosome) of the host cell. Integration can be promoted by inclusion of sequences which promote recombination with the genome, in accordance with standard techniques.

The present disclosure also provides a method which comprises using a construct (e.g. plasmid, vector, etc. as described above) in an expression system in order to express an antigen-binding protein or polypeptide as described above.

In another aspect, the disclosure provides a hybridoma producing the antigen-binding protein (e.g. anti-O1 antigen antibodies or antigen binding fragments thereof) of the disclosure.

A yet further aspect of the disclosure provides a method of production of an antibody binding protein (e.g. anti-O1 antigen antibodies or antigen binding fragments thereof) of the disclosure, the method including causing expression from encoding nucleic acid. Such a method can comprise culturing host cells under conditions suitable for production of said antigen-binding protein.

In some embodiments, the method of production further comprises isolating and/or purifying the antigen binding protein (including anti-O1 antigen antibodies or antigen binding fragments thereof) produced from the host cell or hybridoma.

EXAMPLES

Materials and Methods

Unless otherwise stated, all *K. pneumoniae* isolates were purchased from America Type Culture Collection, International Health Management Associates (IHMA), or Eurofin collection, and cultures were maintained in 2×YT media at 37° C. supplemented with antibiotics when appropriate.

All statistical analysis was performed in GraphPad Prism version 6. For comparing bacterial burden, anti-O1 antigen antibody treated animals were compared with human isotype control antibody treated animals by unpaired t test. Survival results were plotted as Kaplan-Meier curves and analyzed as Log-rank (Mental-Cox) tests.

Example 1: Selection of PBMC and Tonsil Donors with High Antibody Titer Against *Klebsiella Pneumoniae* LPS-O1

Peripheral blood mononuclear cells (PBMC) and sera were separated from buffy coats from healthy blood donors (N=567). PMBC were stored in liquid nitrogen whereas the plasma was stored at 4° C. To identify *Klebsiella pneumoniae* immune donors, all the available sera were tested for binding to Kp43816 and Kp4211 (LPS-O1 serotype), as well as to the unencapsulated mutant strain Kp43816ΔcpsB and the double mutant Kp43816ΔcpsBΔwaaL. The double mutant Kp43816ΔcpsBΔwaaL does not express LPS O antigen on its surface. In addition, all available sera were tested for their bactericidal activity in the presence of complement using a high-throughput serum bactericidal assay (SBA assay). Overnight cultures of luminescent *K. pneumoniae* strain 4211 (lux) were diluted in Muller Hinton II media to make OD600 to be 0.003. Equal volume of sera, 4211 lux, and baby rabbit serum (Cedarlane) were mixed in 384 well plates and incubated at 37° C. for two hours with shaking (250 rpm). The relative light units (RLUs) were then measured using an Envision Multilabel plate reader (Perkin Elmer). The percentage of killing was determined by comparing RLU derived from assays with no antibodies to RLU obtained from human sera.

PBMC donors were ranked based on their binding titers as well as their SBA and OPK activity. OPK assays were performed as described with modifications (Wang, Q. et al. Target-Agnostic Identification of Functional Monoclonal Antibodies Against *Klebsiella pneumoniae* Multimeric MrkA Fimbrial Subunit *J Infect Dis.* 2016 Jun. 1; 213(11): 1800-8). Briefly, log phase cultures of luminescent *K. pneumoniae* capsule mutant strain 43816ΔcpsB (43816ΔcpsB Lux) were diluted to ~2×10$^6$ cells/ml. Bacteria, diluted baby rabbit serum providing complement (Cedarlane, pre-absorbed with Kp43816ΔcpsB, 1:10), dimethylformamide (DMF) differentiated HL-60 cells, and sera were mixed in 384-well plates and incubated at 37° C. for two hours with shaking (250 rpm). The relative light units (RLUs) were then measured using an Envision Multilabel plate reader (Perkin Elmer). The percentage of killing was determined by comparing RLU derived from assays with no antibodies to RLU obtained from human sera.

For tonsil and adenoid donor selection, tonsillar mononucleated cells were polyclonally stimulated as described in Pinna, D., et al., *European Journal of Immunology* 39: 1260-1270 (2009). Supernatants containing polyclonal antibody mixtures were used to determine the presence of antibodies binding to different pools of bacterial strains or to purified bacterial antigens (e.g. LPS or other polysaccharides, bacterial proteins) by enzyme-linked immunosorbent assay (ELISA). Tonsils with strong polyclonal antibody titers against *K. pneumoniae* were selected for antibody generation as described at example 2.

Example 2: Identification of Monoclonal KPA27, KPB202, KPE33, and KPJ4

Memory B cells were isolated from cryopreserved PMBC using CD19 microbeads, followed by depletion of cells carrying IgM, IgD, and IgA by cell sorting. Memory B cells were immortalized as described in Traggiai, E. et al., *Nature Medicine* 10: 871-875 (2004).

KPA27 and KPE33 were isolated from the peripheral blood of two different immune donors: #487 and #262, respectively. They were shown in a primary screening to bind to *Klebsiella pneumoniae* of the LPS-O1 serotype and to mediate complement-dependent killing (SBA) of strain Kp4211 (LPS-O1). KPA27 and KPE33 were isolated from immune donors as IgG2 antibodies.

KPB202 and KPJ4 were isolated from tonsillar B cells of two different donors: T6 (KPB202) and T8 (KPJ4). They were shown in a primary screening to bind to *Klebsiella pneumoniae* of the LPS-O1 serotype and to mediate complement-dependent killing (SBA) of strain Kp4211 (LPS-O1). KPB202 and KPJ4 were isolated from donors as IgG1 and IgG2 antibodies, respectively.

Example 3: Isolation of *K. Pneumoniae* O1 Antigen Specific Hybridomas

*K. pneumoniae* isolates were purchased from America Type Culture Collection or Eurofin collection. Balb/c mice were immunized weekly with the *K. pneumoniae* 43816DM via intraperitoneal (ip) route for four weeks followed by a final boost with a mixture of wild type *K. pneumoniae* clinical isolates. At the end of the immunization, lymph node and splenic B cells were harvested and fused with P3X myelomas. Supernatants from the resulting hybridomas were then screened for binding to 43816DM by whole bacterial ELISA. Positive hybridomas were sub-cultured in antibiotics free medium and the supernatants were subjected to SBA and OPK assay to select for potentially protective ones against *K. pneumoniae*. One positive hybridoma produced the 54H7 antibody.

Example 4: Anti-O1 Antigen Antibody Characterization

Isolated antibodies were tested for their binding to whole bacteria, opsonophagocytic killing (OPK), complement-dependent killing (SBA), LPS neutralization, and binding to purified O1 LPS. The characteristics of isolated anti-O1 antigen antibodies are summarized in Table 7.

Figure 1A:
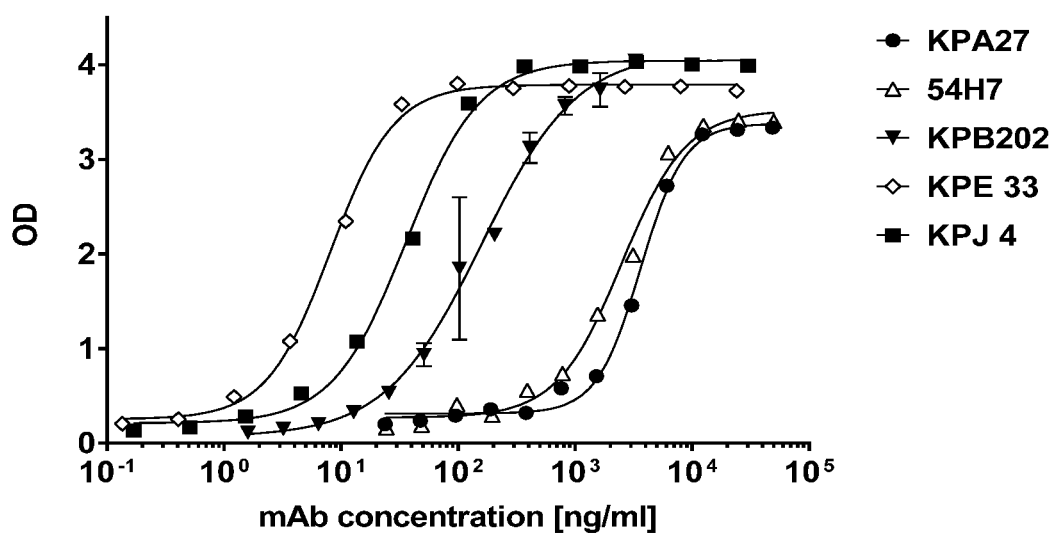
Figure 1B:
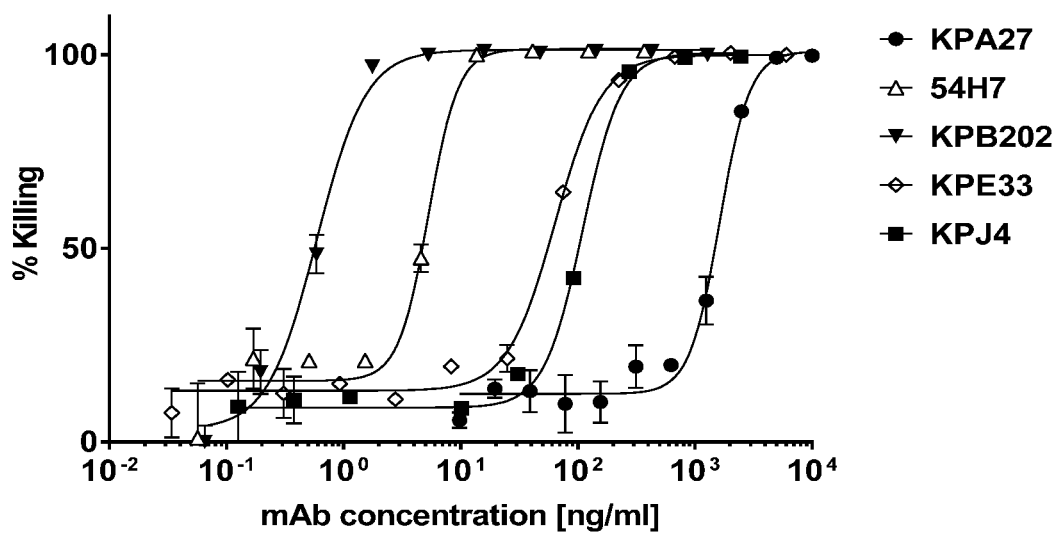
Figure 1C:
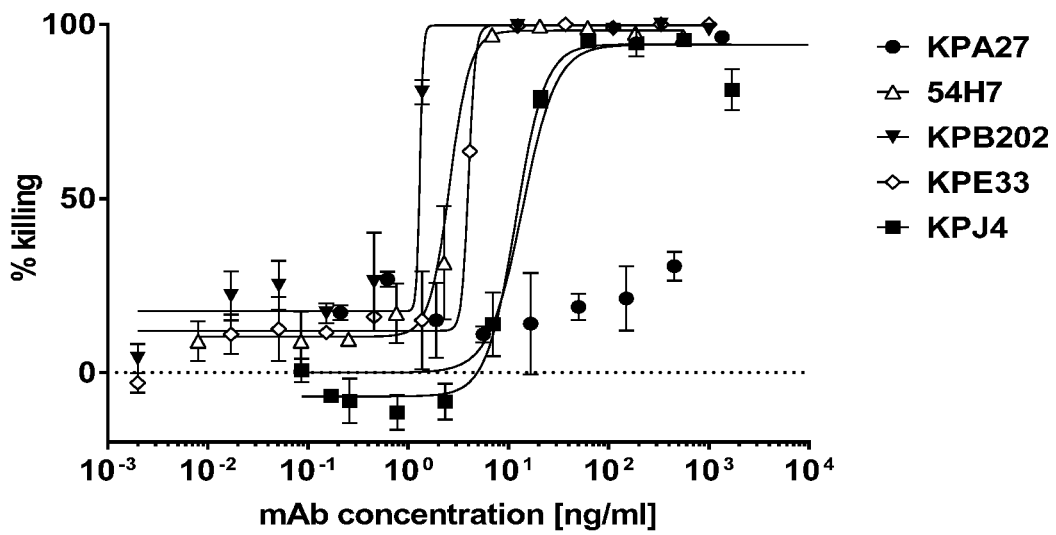

OPK assays were performed as described with modifications (Wang, Q. et al., *J. Infect. Dis.* 213:1800-8 (2016)). Briefly, log phase cultures of luminescent *K. pneumoniae* capsule mutant strain 43816ΔcpsB (43816ΔcpsB Lux) were diluted to ~2×10$^6$ cells/ml. Bacteria, diluted baby rabbit serum providing complement (Cedarlane, pre-absorbed with Kp43816ΔcpsB, 1:10), dimethylformamide (DMF) differentiated HL-60 cells, and antibodies were mixed in 384-well plates and incubated at 37° C. for two hours with shaking (250 rpm). The relative light units (RLUs) were then measured using an Envision Multilabel plate reader (Perkin Elmer). The percentage of killing was determined by comparing RLU derived from assays with no antibodies to RLU obtained from anti-*K. pneumoniae* mAbs and a negative control mAb. The results are shown in FIG. 1C. The 54H7, KPB202, KPA27, KPE33, and KPJ4 antibodies induced OPK killing.

The susceptibility of the *K. pneumoniae* strain Kp4211 lux to serum and antibody dependent killing was measured by high throughput serum bactericidal assay (SBA). Overnight cultures of luminescent *K. pneumoniae* strain 4211 (lux) were diluted in Muller Hinton II media to make OD600 to be 0.003. Equal volume of antibodies, 4211 lux, and baby rabbit serum (Cedarlane) were mixed in 384 well plates and incubated at 37° C. for two hours with shaking (250 rpm). The relative light units (RLUs) were then measured using an Envision Multilabel plate reader (Perkin Elmer). The percentage of killing was determined by comparing RLU derived from assays with no antibodies to RLU obtained from anti-*K. pneumoniae* mAbs and a negative control mAb. The results are shown in FIG. 1B. The 54H7, KPB202, KPA27, KPE33, and KPJ4 antibodies all kill *K. pneumoniae* via complement-dependent killing as shown by a serum bactericidal assay (SBA).

LPS neutralization was assayed by utilizing a murine RAW264.7 macrophage cell line carrying a firefly luciferase reporter gene under the control of an NF-κB-responsive promoter (RAW264.7-lux). Serially diluted antibody stocks were mixed with LPS in a 1:1 ratio and incubated at 4° C. for 1 hr. Antibody/LPS mixture was then diluted 1:10 into assay plates containing pre-seeded RAW264.7-lux cells (5e3 cells/well), which were then placed at 37° C./5% $CO_2$ for 2.5 hours. Following incubations, Steady Glo (Promega) was then added to each well and incubated for another 20 min protected from light. The relative light units (RLUs) were then measured using an Envision Multilabel plate reader (Perkin Elmer). The percentage of inhibition was determined by comparing RLU derived from assays with no antibodies to RLU obtained from anti-*K. pneumoniae* mAbs and a negative control mAb. Activation of TLR4 receptors by bacterial LPS leads to downstream activation of the NF-κB transcriptional regulator. A decrease in induction of NF-κB-responsive luciferase activity was used to quantify ITS neutralization activity by LPS mAbs. The results are summarized in Table 7. The 54H7 and KPB202 antibodies neutralized LPS, but the KPA27, KPE33, and KPJ4 antibodies did not.

Binding to purified O1 LPS was assayed by standard ELISA method. Briefly, ELISA plates (Nunc MaxiSorp) were coated with purified O1 LPS in PBS, pH 7.2, overnight at 4 C, followed by blocking the plates with PBS supplemented with 1% BSA (PBS-B). The coated plates were incubated with series dilutions of monoclonal antibodies for 1 h at room temperature. The plates were then washed with PBS containing 0.1% Tween-20 (PBS-T) before HRP-conjugated anti-human secondary antibodies were added for 1 hour followed by TMB TMB (3, 3', 5, 5'-Tetrametheylbenzidine) substrates. The absorbance of 450 nm was measured by microplate reader (Molecular Devices) and the data were plotted with Prism software. The results are shown in FIG. 1A. The 54H7, KPB202, KPA27, KPE33, and KPJ4 antibodies bound to purified O1 LPS.

TABLE 7

Summary of Anti-O1 Antigen Antibodies

| Category | mAb | Original Isotype | LPS Neut (O1) $IC_{50}$ (ng/mL) | SBA Kp4211lux $IC_{50}$ (ng/mL) | D Capsule OPK $IC_{50}$ (ng/mL) |
|---|---|---|---|---|---|
| Class I | 54H7 | Ms IgG3 | <0.1 | 5.2 | 2.5 |
|  | KPB202 | Hu rIgG1 | 38 | 0.6 | 0.9 |
| Class II | KPE33 | Hu rIgG2 | — | 64 | 2.5 |
|  | KPJ4 | Hu rIgG2 | — | 110 | 11 |
|  | KPA27 | Hu rIgG2 | — | 1625 | 670 |

Example 5: Anti-O1 Antigen Antibodies Reduce *Klebsiella* Organ Burden

The ability of anti-O1 antigen antibodies to reduce organ burden was tested in bacterial infection models. In these experiments, C57BL/6 mice were received from Jackson laboratories and maintained in a special pathogen free facility. All animal experiments were conducted in accordance with IACUC protocol and guidance. *K. pneumoniae* strains were grown on agar plates overnight and diluted in saline at proper concentration. The inoculum titer was determined by plating a serial dilution of bacteria onto agar plates prior to and post challenge.

Figure 2:
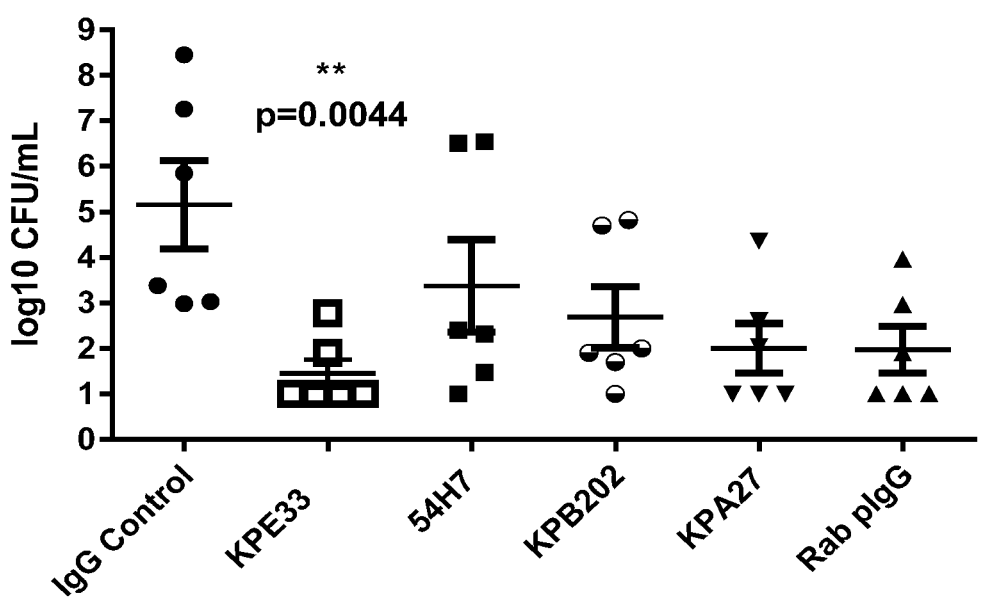

Antibodies and controls at 15 mg/kg were administered 24 hours prior to bacterial infection. C57BL/6 mice were inoculated with 1e4 CFU Kp8045 (O1:K1) bacteria in 40 µl saline intranasally to induce pneumonia. The lung bacterial burden was measured by plating lung homogenates onto agar plates to determine CFU 48 hours post infection. The results are shown in FIG. 2. KPE33 significantly reduced organ burden and other anti-O1 antigen antibodies also reduced organ burden for about 2-3 log 48 hours post *K. pneumoniae* infection.

Example 6: Anti-O1 Antigen Antibodies Protect Against Lethal Bacterial Challenges The ability of anti-O1 antigen antibodies to protect against lethal bacterial challenges was also assessed.

Figure 3A:
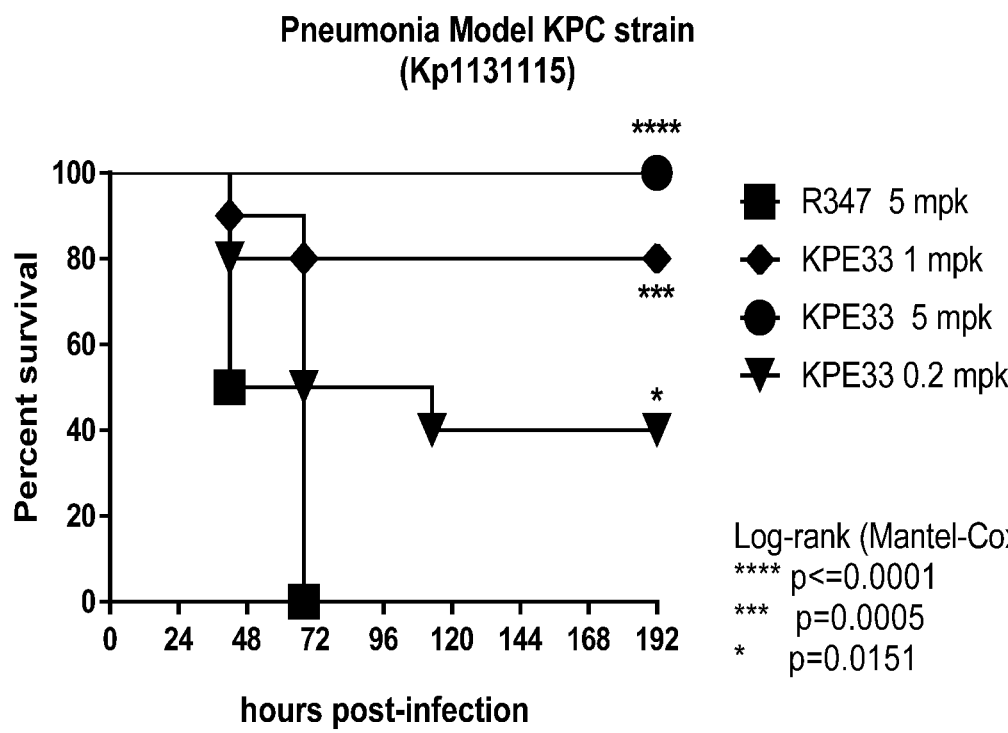

In an acute pneumonia model, C57BL/6 mice were inoculated intranasally with 1e4 to 1e8 CFU of the multi-drug resistant *Klebsiella pneumoniae* carbapenam resistant (CRE) clinical isolate strain KP1131115 (O1). Anti-*K. pneumoniae* monoclonal antibody KPE33 at 0.2, 1, and 5 mg/kg and human IgG1 control antibody at 5 mg/kg were given one hour post bacterial challenge (therapeutic dosing). Mouse survival was monitored daily until up to day 8. The results are shown in FIG. 3A.

Additionally, in an acute pneumonia model, C57BL/6 mice were inoculated intranasally with 1e4 to 1e8 CFU of the multi-drug resistant *Klebsiella pneumoniae* carbapenam resistant (CRE) clinical isolate strain KP1131115 (O1). Anti-*K. pneumoniae* monoclonal antibodies KPE33-H32+L2016(EQ1) and KPE33-H32+L2016(EQ1) at 0.2 and 1 mg/kg and human IgG1 control antibody at 5 mg/kg were given one hour post bacterial challenge (therapeutic dosing). Mouse survival was monitored daily until up to day 8. The results are shown in FIG. 3C.

These results demonstrate that KPE33, KPE33-H32+L2016(EQ1), and KPE33-H32+L2016(EQ1), given therapeutically after bacterial challenge, protect mice from lethal bacterial challenge with a drug resistant *K. pneumoniae* strains KPC Kp1131115

Figure 3B:
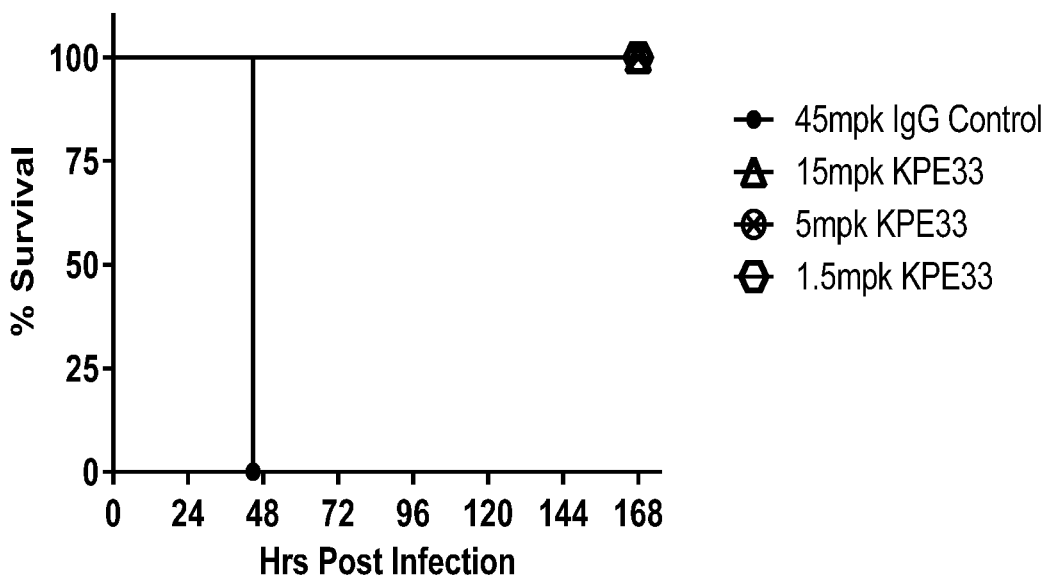

In a bacteremia model, C57BL/6 mice were inoculated intraperitoneally with 1e8 CFU extended spectrum beta lactamase (ESBL) clinical isolate strain Kp8561 (O1). Anti-*K. pneumoniae* monoclonal antibody KPE33 at 1.5, 5, and 15 mg/kg and human IgG1 control antibody at 45 mg/kg were given one hour post bacterial challenge (therapeutic dosing). Mouse survival was monitored daily until up to day 8. The results are shown in FIG. 3B.

The results demonstrate that KPE33, given therapeutically after bacterial challenge, protect mice from extended spectrum beta-lactamase (ESBL) strain Kp8561.

Example 7: Synergy of Anti-O1 Antigen Antibody KPE33 and Antibiotics

The synergy of anti-O1 antigen antibodies and antibiotic was also assessed in the pneumonia and bacteremia mouse models.

Figure 4A:
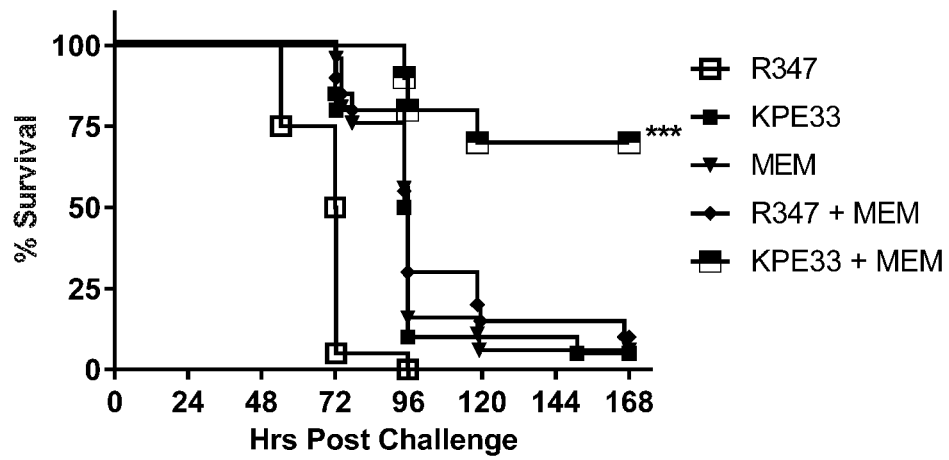
Figure 4B:
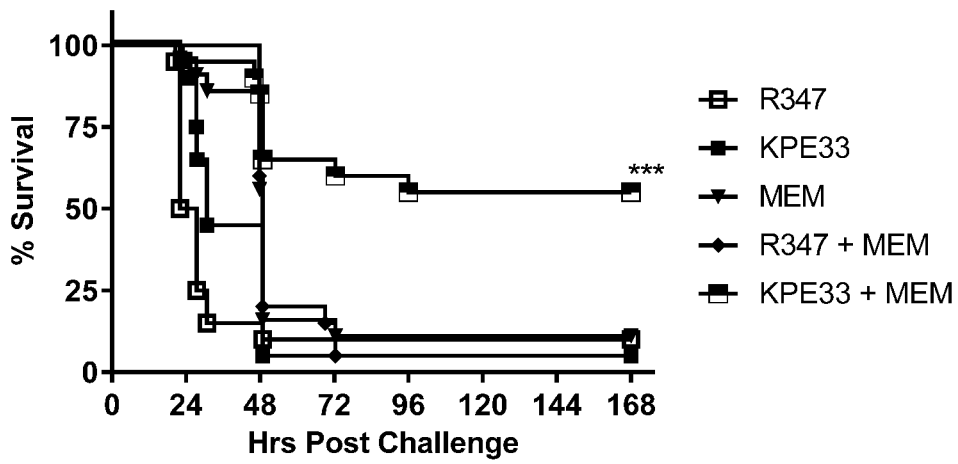

In the pneumonia experiments, C57BL/6 mice were inoculated intranasally with 1e4 to 1e8 CFU of the Kp8045 *Klebsiella*. (See FIG. 4A.) In the bacteremia experiments, mice were inoculated with Kp8561 *Klebsiella*. (See FIG. 4B.) Both sub-therapeutic dosage of antibodies (1 mpk for Kp8045 and 2.5 mpk for Kp8561) and meropenem antibiotic (2.5 mpk for Kp8045 and 5 mpk for Kp8561) were administered post bacterial challenge. Mouse survival was monitored daily until up to day 8.

The results are shown in FIG. 4 and demonstrate that the combination of meropenem and KPE33 showed significant synergy and better protection than monotherapy of either meropenem or KPE33, or the combination of human IgG1 control antibody (R347) and meropenem.

Example 8: KPE33 Sequence Optimization

In order to reduce potential sequence liabilities for antibody development including potential immunogenicity due to anti-drug antibodies, an unpaired Cysteine in the light chain CDR3 of KPE33 was exchanged with Threonine (T), and somatic mutations in the frameworks 1, 2, and 4 of KPE33 were replaced with germ line residues (as summarized in FIG. 5). CDRs were maintained as wildtype, except for the C107T substitution described above. The optimized KPE33 was named KPE33v2016. In order to confirm that the sequence optimization did not changed the interaction with LPS O1, the binding of KPE33 and KPE33v2016 to O1 LPS was tested in solution phase by Octet platform. This platform provides a powerful tool to measure the rate of biomolecular complex formation and complex stability in a more biologically meaningful setting. Briefly, Protein A coated sensors were coated with 2 µg/mL O1 LPS for 10 minutes before being dipped into solution containing 0.2 µg/mL anti-O1 LPS mAbs in Kinetics buffer (ForteBio, dilute 10× to 1× with PBS). Changes in the number of molecules bound to the biosensor caused a shift in the interference pattern that was recorded in real time. As shown in FIG. 5, the mAbs bound to O1 LPS. The affinity constant ($K_D$) of KPE33 and KPE33v2016 to O1 LPS was calculated based on the on-rate and off-rate from Octet sensorgram. Both KPE33 and KPE33v2016 showed comparable affinity constant at the average of 5.83E-09 and 4.13E-09, respectively (FIG. 5).

KPE33v2016 was further optimized, thereby creating two new variants—KPE33 H32+L2016(1EQ) and KPE33 H33+L2016(1EQ). Both of these variants contain a Methionine to Isoleucine mutation adjacent to CDRH1, a Tryptophan to Tyrosine mutation in CDRH2, an Aspartate to Glutamate mutation adjacent to CDRH2, Asparagine to Glutamine and Methionine to Leucine mutations in FRH3 and an Aspartate to Asparagine mutation in CDRH3. In addition, KPE33 H32+L2016(1EQ) had four FRH3 residues changed to the germ-line residues, whereas KPE33 H33+L2016(1EQ) only has three of the same FRH3 residues changed to the germ-line. Both of these variants contain the same light chain as KPE33v2016, but with a single Glutamate to Glutamine mutation in residue 1. The affinities of KPE33 H32+L2016(1EQ) and KPE33 H33+L2016(1EQ) were measured by Octet and gave values of 4.46E-09 and 5.01E-09 respectively.

Figure 6:
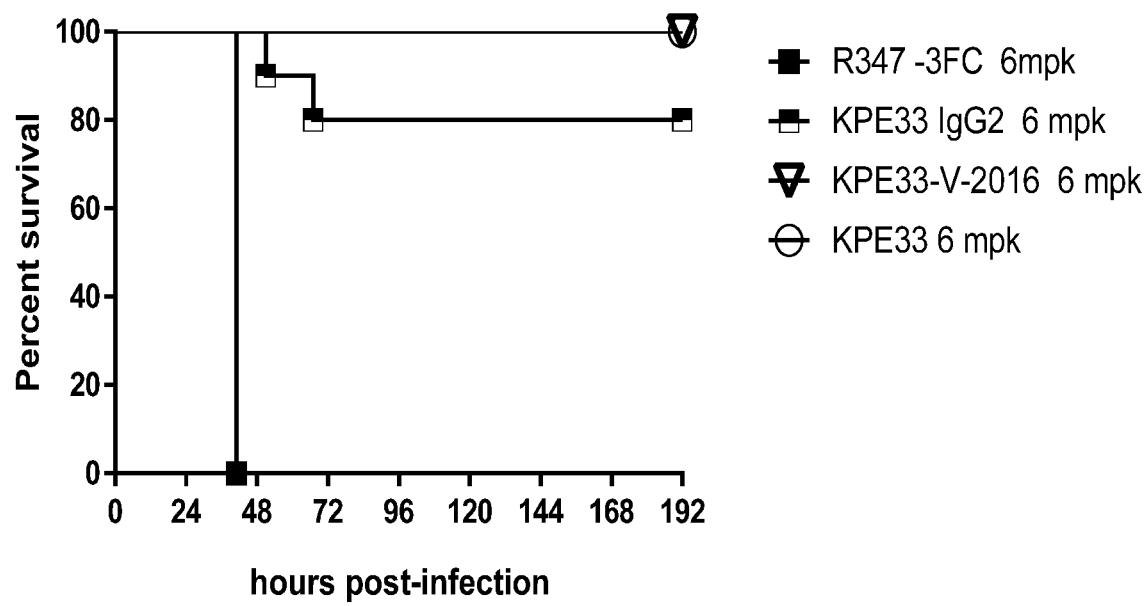

In order to confirm that the sequence optimization did not inhibit efficacy of the KPE33 antibody, the optimized KPE33V2016 antibody was assayed in the same lethal pneumonia model described in Example 6. KPE33 or KPE33-V-2016 were administered at a dose of 6 mg/kg 1 hour post bacterial infection with a *Klebsiella pneumoniae* carbapenam resistant strain. The results, shown in FIG. 6, demonstrate that both KPE33 and KPE33V2016 showed a similar level of protection when compared with a human IgG1 control antibody. An IgG2 version of KPE33 showed slightly lower activity than the KPE33-IgG1 (see FIG. 6).

Example 9: Anti-O1 Antigen Antibodies Protect in Co-Infection Models

In order to evaluate the efficacy of anti-O1 antigen antibodies in co-infection, female 7-8 week old C57BL/6 mice were briefly anesthetized in 3% Isoflurane and 50 µl of bacterial suspension was placed on the nares. Animals were inoculated with 5e7 CFU *S. aureus* SF8300 (USA300) alone or in combination with 1.5e2 CFU of *K. pneumoniae* and monitored up to 7 days for survival studies. For organ burden studies, lungs and spleens were harvested at 24 or 48 hours post challenge as described in Example 5 above. For protection studies, mice were passively immunized (0.5 mL, ip) with KPE33 or control mAb before lethal bacterial challenge. All data were plotted in Prism.

Figure 7A:
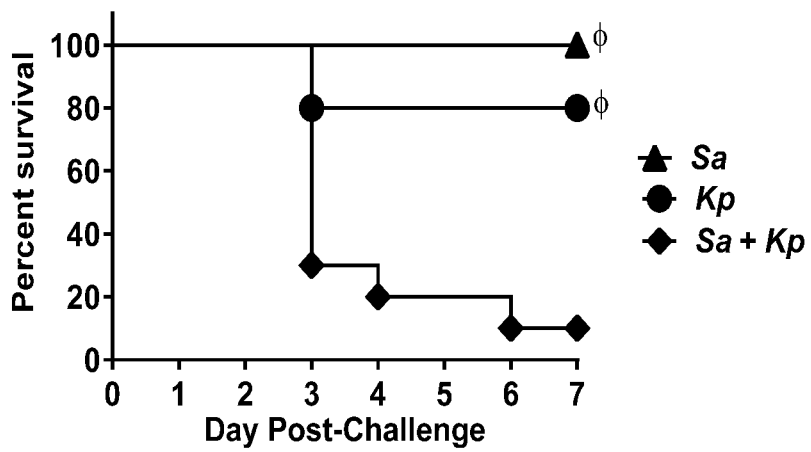
Figure 7B:
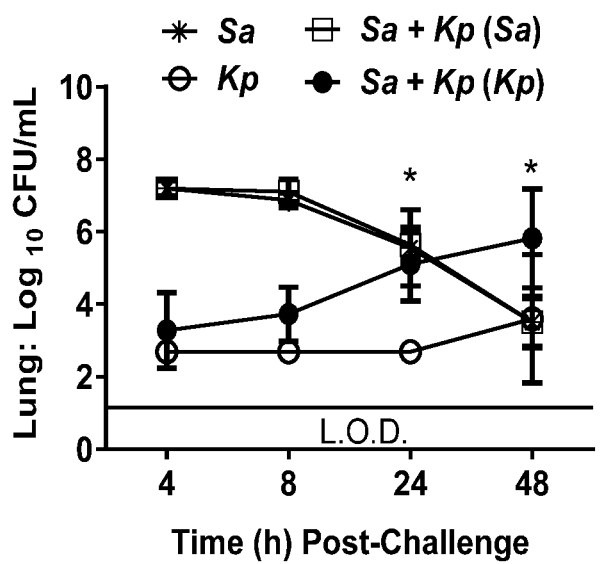
Figure 7C:
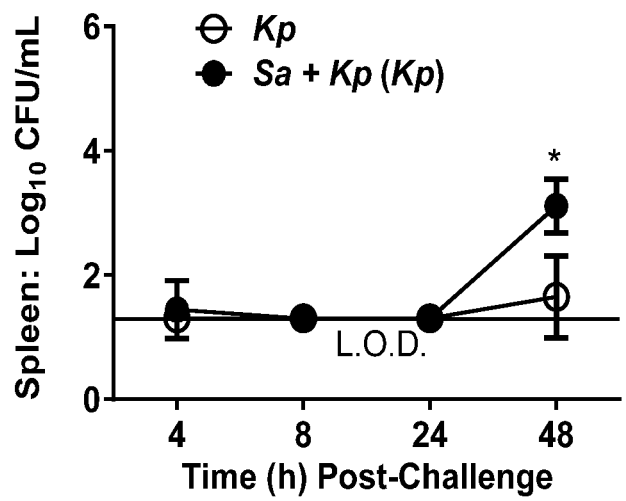
Figure 7D:
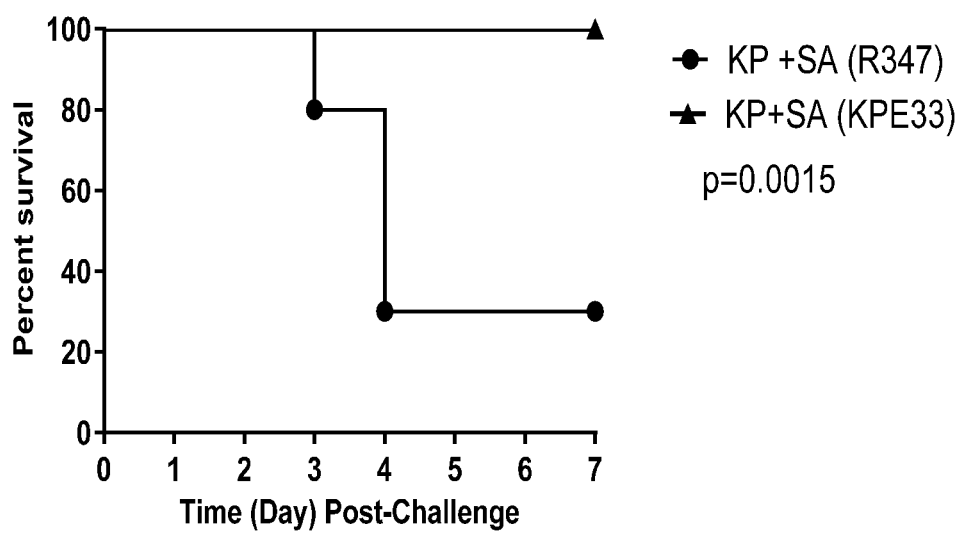

The results are shown in FIGS. 7A-D. Co-infection with sub-lethal inoculums of *S. aureus* and *K. pneumoniae* caused lethal pneumonia (FIG. 7A) and *K. pneumoniae* bacterial burdens were significantly increased in the lungs (FIG. 7B) and spleens (FIG. 7C) of mice co-infected with *K. pneumoniae* and *S. aureus* as compared to mice infected with *K. pneumoniae* alone. Single prophylactic treatment with KPE33 24 hours prior to the co-infection rescued the mice (FIG. 7D).

Example 10: Anti-O1 Antigen Antibodies Reduce Serum Cytokines After LPS Challenge In order to determine the effect of anti-O1 antigen antibodies on serum cytokines after LPS challenge, C57BL/6 mice were challenged with 0.3 mg/kg LPS intraperitoneally 24 hours after anti-O1 administration. 3 hours later, animals were sacrificed, and serum cytokines were measured using a Meso Scale Discovery (MSD) proinflammatory cytokine kit based on manufacturer's instruction. Polymyxin B (PMB) was used as a positive control. Serum IL-6, TNF-alpha, and CXCL1 concentration were plotted in Prism.

The results are shown in FIG. 8 and demonstrate that 54H7 reduces serum IL-6, KC, and TNF-alpha levels after LPS challenge with Kp43816 LPS and Kp15380 LPS.

Example 11: Anti-O1 Antigen Antibodies Protect Mice in Endotoxemia Model

In order to determine the protective effect of anti-O1 antigen antibodies, female mice (Balb/c), aged 6-8 weeks, were sensitized with D-galactose (D-Gal, 12 mg/kg), and subsequently challenged intraperitoneally (ip) with 10-50 ng of LPS 24 hours after anti-O1 antigen antibody administration. Antibody was administered at doses of 0.2 mg/kg, 1 mg/kg, or 5 mg/kg. Mouse survival was monitored up to 6 days post LPS challenge.

Figure 9:
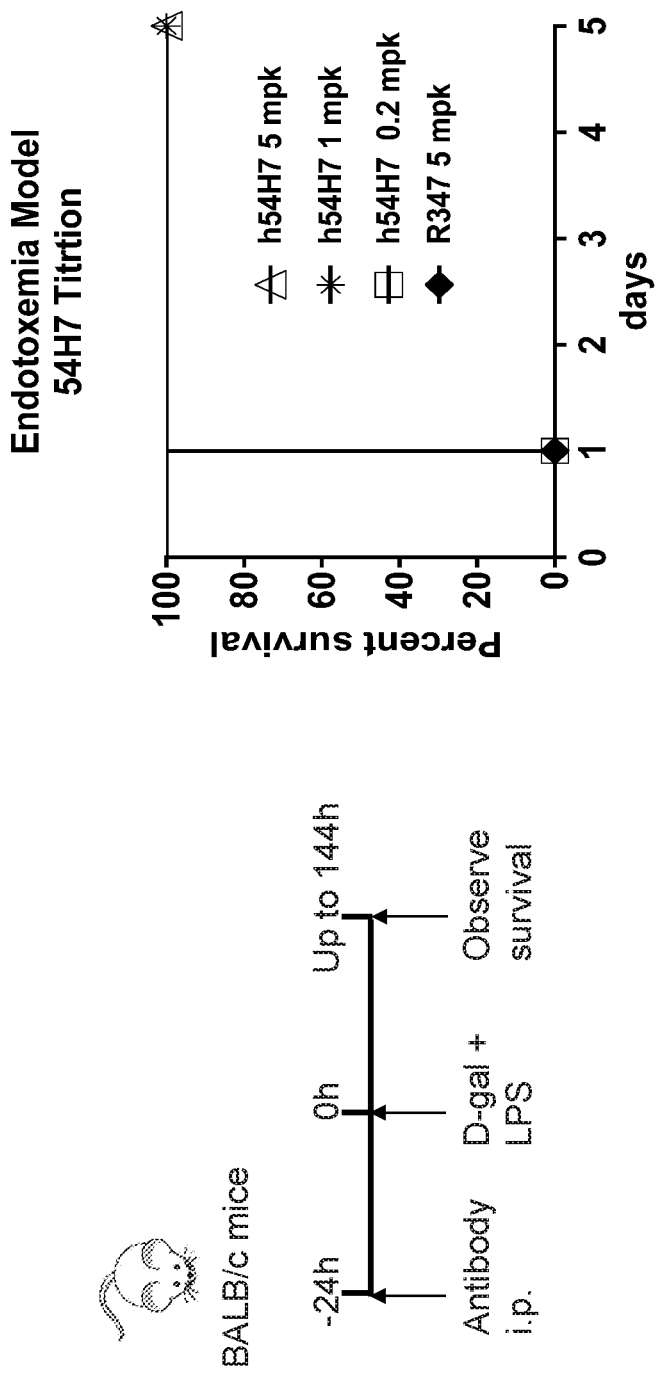

The results are shown in FIG. 9 and demonstrate that 54H7 protects mice in the endotoxemia LPS-induced sepsis model when administered at a dose of either 1 mg/kg or 5 mg/kg as compared to a control IgG antibody (R347).

Example 12: Anti-O1 Antigen Antibody 5H47 Reduces *Klebsiella* Organ Burden and has Synergy with Antibiotics The ability of anti-O1 antigen antibody 5H47 to reduce organ burden was tested in bacterial infection models.

Figure 10A:
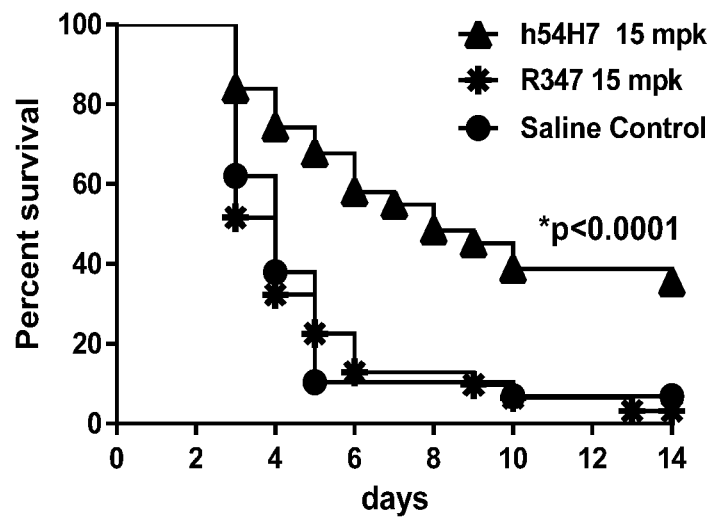

In order to determine the efficacy of anti-O1 antigen antibodies in combination with antibiotics, 54H7 was tested in an acute pneumonia models. C57BL/6 mice were inoculated intranasally with 1e4 CFU of highly virulent strain Kp43816 (O1). Anti-*K. pneumoniae* monoclonal antibody 54H7 at 15 mg/kg and human IgG1 control antibody at 15 mg/kg were given 24 hour prior bacterial challenge (prophylatic dosing). Mouse survival was monitored daily until up to day 14. The results are shown in FIG. 10A.

Figure 10B:
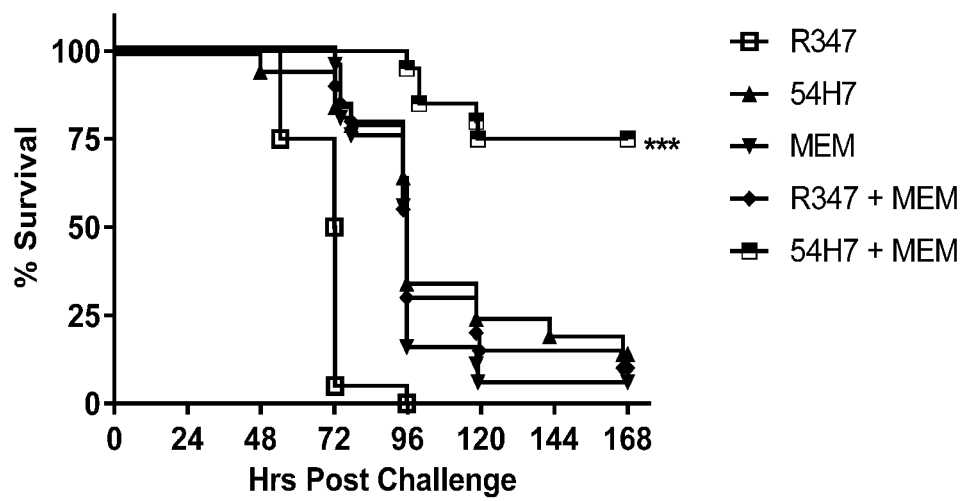

The synergy of anti-O1 antigen antibodies and antibiotic was also assessed in the pneumonia mouse models. C57BL/6 mice were inoculated intranasally with 1e4 to 1e8 CFU of Kp8045 *Klebsiella*. Both sub-therapeutic dosage of antibodies (1 mpk) and meropenem antibiotic (1.5 mpk) were administered at 1 hour or 4 hour post bacterial challenge, respectively. Mouse survival was monitored daily until up to day 8. The results are shown in FIG. 10B.

54H7 showed significant protection at 15 mpk in monotherapy against Kp43816 pneumonia model. When sub-therapeutic dosages of 54H7 and meropenem were used, the combination showed significant synergy and better protection than monotherapy of either meropenem or 54H7 alone, or the combination of human IgG1 control antibody (R347) and meropenem.

Example 13: Epitope Studies

Figure 11:
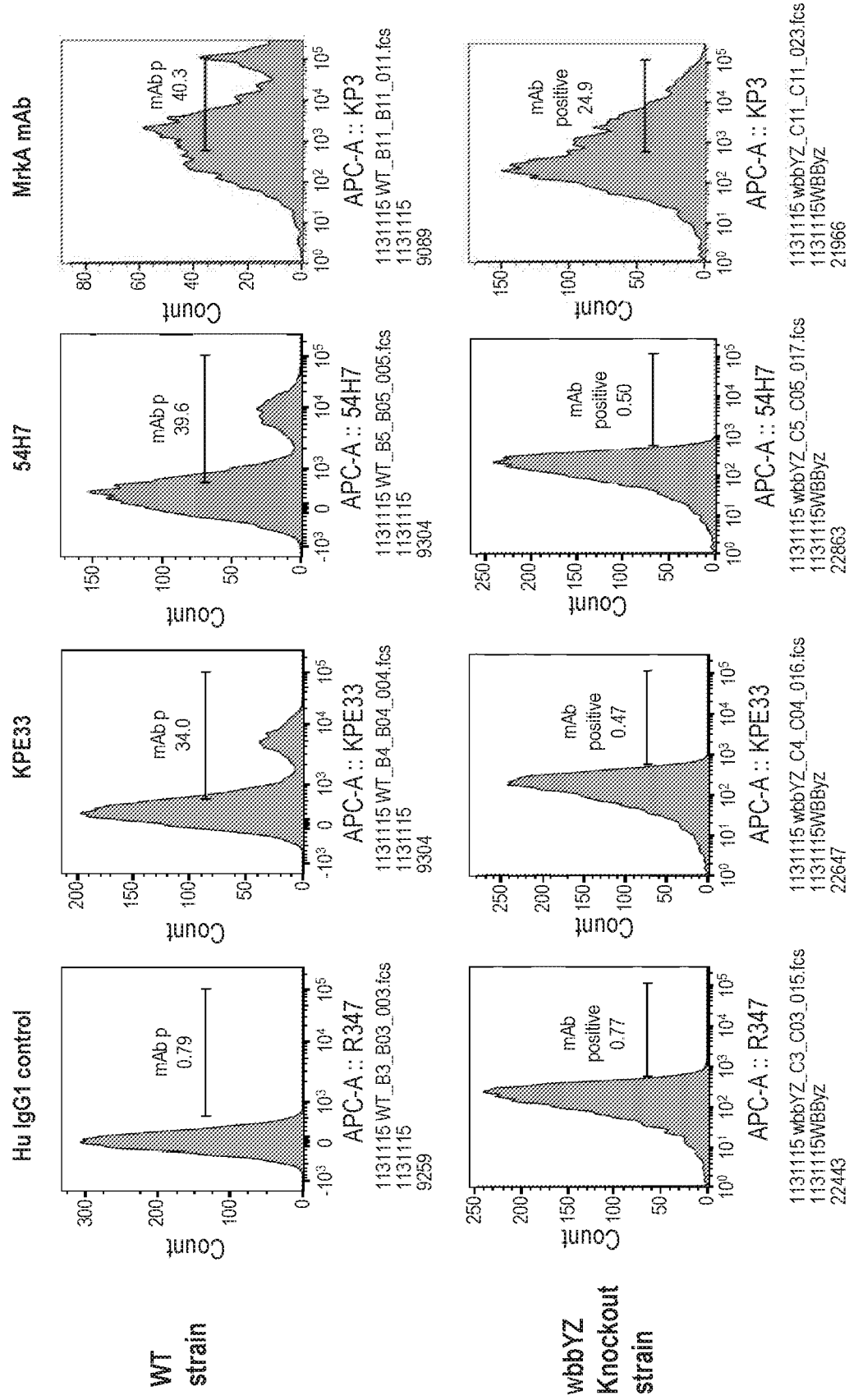
FIG. 11 shows that deletion of the wbbYZ gene, which encodes the D-Galactan II domain in the LPS structure, abolishes the binding of the KPE33 and 54H7 antibodies to *Klebsiella pneumoniae* strain Kp113115 as shown by flow cytometry analysis.
Figure 12:
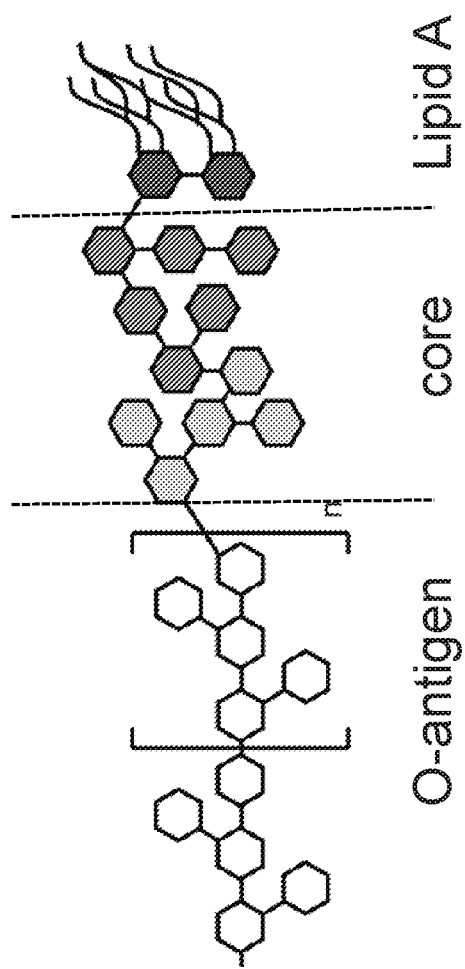
FIG. 12 shows the structure of O1 LPS including lipid A, a core oligosaccharide and a highly variable O-antigen constituted of repeating oligosaccharide units. The table at the bottom provides the chemical compositions of the O1, O2a, and O2ac LPS serotypes.

*Klebsiella pneumoniae* wbbYZ gene locus encodes D-Galactan II domain in LPS structure, which defines O1 serotype over O2. (Hsieh, P F. et al., *Front Microbiol.* 5: 608 (2014). To investigate if the anti-O1 antigen antibodies disclosed herein bind the D-Galactan II domain, the O1 strain Kp1131115 was converted to an O2 serotype by genetically knocking out the wbbYZ gene locus. The binding of *Klebsiella pneumoniae* O1 LPS antibodies to Kp1131115 wild type (WT strain) and Kp1131115ΔwbbYZ strain was tested by FACS analysis. A human IgG1 and an anti-MrkA antibody were used as a negative control and a positive control, respectively. WbbYZ gene knockout completely abolished the binding of 54H7 and KPE33. However, knocking out this gene did not change binding to the MrkA antibody. These data, shown in FIG. 11, indicate that both KPE33 and 54H7 bind to the D-Galactan II domain of the *Klebsiella pneumoniae* O1 LPS antigen. (FIG. 12 shows the structure of O1 LPS.)

Although KPE33 and 54H7 both bind the D-Galactan II domain of O1 LPS, they do not bind to the same epitope as measured by Fortebio Octet using a capture probe preloaded with purified O1 LPS in competitive binding studies with KPE33 and 54H7. Briefly, after initial binding with 10 µg/mL KPE33, the probe was incubated with antibody mixtures containing 10 µg/mL KPE33 with equal concentrations of 54H7, KPE33, or the control antibody R347. The results are shown in FIG. 13. Only 54H7 was able to show additional binding, indicating KPE33 and 54H7 occupy different epitopes on O1 LPS.

Example 14: Anti-O1 Antigen Antibodies Bind to Clinically Relevant *Klebsiella*

In order to determine if anti-O1 antigen antibodies bind to clinically relevant *Klebsiella* strains, the binding of KPE33 to clinical isolates was determined by western blot assay. A summary of the clinically relevant *Klebsiella* strains which KPE33 binds is shown in Table 8. The ability of KPE33 to bind to all of these strains as well as its ability to protect against four different strains in vivo indicate that KPE33 can kill many clinically relevant *Klebsiella* strains.

TABLE 8

Summary of clinical *Klebsiella* strains which KPE33 binds.

| | Region | Country | IHMA Number | Body Location | Facility Name | Molecular Summary |
|---|---|---|---|---|---|---|
| 1 | Europe | Portugal | 845904 | Respiratory: Sputum | Medicine ICU | SHV-71(b); TEM-1(b); KPC-3; |
| 2 | Europe | Portugal | 845927 | INT: Wound | Emergency Room | SHV-1(b); TEM-1(b); KPC-2; |
| 3 | Europe | Greece | 848845 | Respiratory: Endotracheal aspirate | General Unspecified ICU | SHV-36(u); TEM-1(b); KPC-3; |
| 4 | Middle East | Israel | 849626 | INT: Wound | Medicine General | SHV-11(b); TEM-1(b); KPC-3; |
| 5 | Europe | Romania | 850438 | INT: Wound | Surgery General | SHV-12(e); KPC-2; |
| 6 | South Pacific | Philippines | 850705 | Respiratory: Endotracheal aspirate | Pediatric ICU | SHV-11(b); TEM-1(b); CTX-M-2; KPC-2; OXA-163(e) |
| 7 | South Pacific | Philippines | 850793 | SSI: Abscess Cavity | Other | SHV-1(b); CTX-M-15; IMP-4; |
| 8 | Europe | Romania | 869921 | Respiratory: Endotracheal aspirate | General Unspecified ICU | SHV-11(b); TEM-1(b); KPC-2; |
| 9 | Europe | Portugal | 909704 | Respiratory: Sputum | Other | SHV-11(b); TEM-1(b); KPC-2; |
| 10 | Europe | Belgium | 918171 | INT: Wound | Surgery General | SHV-12(e); TEM-1(b); KPC-2; |
| 11 | Europe | Turkey | 926874 | Respiratory: Endotracheal aspirate | General Unspecified ICU | SHV-11(b); KPC-2; |
| 12 | Europe | Portugal | 938176 | Respiratory: Sputum | Medicine General | SHV-11(b); KPC-2; |
| 13 | Europe | Portugal | 938188 | Respiratory: Sputum | Medicine General | SHV-OSBL(u); TEM-OSBL(u); KPC-3; |
| 14 | South Pacific | Philippines | 966515 | INT: Burn | Surgery ICU | SHV-1(b); CMY-4; KPC-2; |
| 15 | Latin America | Chile | 969741 | INT: Wound | Medicine General | SHV-12(e); TEM-OSBL(u); CTX-M-2; |
| 16 | Europe | Russia | 976029 | Respiratory: Bronchoalveolar lavage | Surgery ICU | SHV-1(b); ACT-New Variant; KPC-2; |
| 17 | Europe | Russia | 1049366 | Respiratory: Other | Surgery ICU | |
| 18 | Latin America | Venezuela | 1073570 | Respiratory: Endotracheal aspirate | None Given | SHV-1(b); TEM-1(b); KPC-3; |
| 19 | Europe | Spain | 1073967 | CVS: Blood | Medicine General | SHV-1(b); TEM-1(b); CTX-M-2; KPC-3; |
| 20 | Asia | Thailand | 1082632 | INT: Wound | Surgery General | KPC-2; |
| 21 | North America | United States | 1103979 | INT: Skin Ulcer | Medicine General | |
| 22 | Europe | Greece | 1104762 | INT: Carbuncle | Medicine General | |
| 23 | Europe | Belgium | 1130776 | Respiratory: Endotracheal aspirate | Surgery ICU | SHV-1(b); CTX-M-15; |
| 24 | Latin America | Chile | 1131115 | CVS: Blood | Medicine General | SHV-1(b); CTX-M-15; IMP-4; |
| 25 | Middle East | Kuwait | 1143489 | INT: Wound | Medicine ICU | |
| 26 | Latin America | Chile | 1145452 | Respiratory: Endotracheal aspirate | Medicine ICU | SHV-11(b); TEM-1(b); KPC-3; |
| 27 | Asia | China | 974761 | Respiratory: Sputum | Surgery General | SHV-OSBL(u); TEM-OSBL(u); CTX-M-3; KPC-2; |
| 28 | Europe | Russia | 976050 | Respiratory: Endotracheal aspirate | Surgery ICU | SHV-OSBL(u); CTX-M-15; OXA-48(c) |
| 29 | Europe | Russia | 1049364 | Respiratory: Other | Surgery ICU | |
| 30 | Europe | Portugal | 909699 | GU: Urine | Surgery General | SHV-1(b); CTX-M-15; KPC-3; |

TABLE 8-continued

Summary of clinical *Klebsiella* strains which KPE33 binds.

| | Region | Country | IHMA Number | Body Location | Facility Name | Molecular Summary |
|---|---|---|---|---|---|---|
| 31 | Latin America | Venezuela | 955418 | GU: Urine | Medicine General | SHV-5(e); TEM-OSBL(u); KPC-2; |
| 32 | Europe | Portugal | 955770 | GU: Urine | Emergency Room | SHV-OSBL(u); TEM-OSBL(u); CTX-M-15; KPC-3; |
| 33 | Europe | Portugal | 955859 | GU: Urine | Medicine General | SHV-OSBL(u); TEM-OSBL(u); CTX-M-15; KPC-3; |
| 34 | Europe | Portugal | 955932 | GU: Urine | Medicine General | SHV-OSBL(u); TEM-OSBL(u); CTX-M-15; KPC-3; |
| 35 | Europe | Poland | 971428 | GU: Urine | Pediatric General | SHV-OSBL(u); TEM-OSBL(u); CTX-M-15; |
| 36 | Africa | Nigeria | 1043234 | GU: Urine | Medicine General | CTX-M-15; NDM-1; |
| 37 | Latin America | Mexico | 846238 | Respiratory: Bronchoalveolar lavage | Medicine ICU | SHV-12(e); CTX-M-15; |
| 38 | Latin America | Mexico | 846241 | Respiratory: Endotracheal aspirate | Medicine ICU | SHV-12(e); TEM-1(b); CTX-M-2; |
| 39 | Latin America | Mexico | 846246 | Respiratory: Bronchoalveolar lavage | Surgery ICU | SHV-12(e); TEM-1(b); CTX-M-2; |
| 40 | Latin America | Chile | 847196 | Respiratory: Endotracheal aspirate | Medicine ICU | SHV-1(b); TEM-1(b); CTX-M-15; |
| 41 | Latin America | Chile | 847201 | Respiratory: Endotracheal aspirate | Medicine ICU | SHV-11(b); TEM-1(b); CTX-M-15; |
| 42 | Latin America | Chile | 847208 | Respiratory: Endotracheal aspirate | Medicine ICU | SHV-12(e); TEM-1(b); CTX-M-15; |
| 43 | Africa | South Africa | 849824 | Respiratory: Sputum | General Unspecified ICU | SHV-11(b); CTX-M-15; |
| 44 | Africa | South Africa | 862530 | Respiratory: Sputum | Medicine General | CTX-M-14; DHA-1; |
| 45 | Europe | Turkey | 868768 | INT: Wound | Surgery General | SHV-133(u); VEB-1; |
| 46 | Europe | Russia | 870306 | Respiratory: Bronchoalveolar lavage | General Unspecified ICU | SHV-1(b); CTX-M-15; OXA-48(c) |
| 47 | Asia | China | 871359 | Respiratory: Sputum | Medicine General | SHV-11(b); TEM-1(b); CTX-M-15; |
| 48 | Asia | Thailand | 872556 | Respiratory: Sputum | Medicine General | SHV-11(b); TEM-1(b); CTX-M-15; |
| 49 | Europe | Russia | 874875 | Respiratory: Sputum | Medicine General | SHV-1(b); TEM-1(b); CTX-M-28; |
| 50 | Europe | Russia | 874880 | Respiratory: Bronchoalveolar lavage | Surgery General | SHV-1(b); TEM-1(b); CTX-M-15; |
| 51 | Europe | Russia | 874898 | Respiratory: Bronchoalveolar lavage | Surgery General | SHV-11(b); TEM-1(b); CTX-M-15; |
| 52 | Europe | Russia | 874904 | Respiratory: Sputum | Medicine General | SHV-1(b); TEM-1(b); CTX-M-15; GES-1(e); |
| 53 | Europe | Russia | 874909 | Respiratory: Bronchoalveolar lavage | Medicine General | SHV-5(e); |
| 54 | Europe | Russia | 874926 | Respiratory: Sputum | Medicine ICU | SHV-1(b); TEM-1(b); CTX-M-15; |
| 55 | Europe | Belgium | 875638 | Respiratory: Endotracheal aspirate | General Unspecified ICU | SHV-11(b); TEM-1(b); CTX-M-15; |
| 56 | Asia | Taiwan | 883550 | GU: Urine | Medicine General | SHV-1(b); TEM-1(b); CTX-M-15; |

TABLE 8-continued

Summary of clinical *Klebsiella* strains which KPE33 binds.

| | Region | Country | IHMA Number | Body Location | Facility Name | Molecular Summary |
|---|---|---|---|---|---|---|
| 57 | Europe | France | 887009 | Respiratory: Endotracheal aspirate | Surgery ICU | SHV-136(u); TEM-1(b); CTX-M-15; |
| 58 | Asia | Thailand | 894614 | Respiratory: Sputum | Medicine General | SHV-OSBL(u); TEM-OSBL(u); CTX-M-15; |
| 59 | Latin America | Brazil | 900684 | Bodily Fluids: Thoracentesis | Medicine General | SHV-12(e); TEM-OSBL(u); CTX-M-15; |
| 60 | Asia | China | 908116 | Respiratory: Sputum | Medicine ICU | SHV-5(e); TEM-OSBL(u); CTX-M-15; |
| 61 | Latin America | Chile | 924298 | Respiratory: Endotracheal aspirate | Surgery ICU | SHV-OSBL(u); CTX-M-15; |
| 62 | Asia | Thailand | 926437 | Respiratory: Sputum | Medicine ICU | SHV-OSBL(u); CTX-M-15; |
| 63 | Europe | Romania | 938765 | Respiratory: Other | None Given | SHV-12(e); |
| 64 | Europe | Romania | 938936 | INT: Wound | Medicine ICU | SHV-OSBL(u); CTX-M-55; |
| 65 | Middle East | Israel | 948159 | Respiratory: Endotracheal aspirate | Medicine General | SHV-OSBL(u); TEM-OSBL(u); CTX-M-15; |
| 66 | Asia | Taiwan | 949403 | Respiratory: Other | Medicine ICU | SHV-12(e); |
| 67 | Europe | Romania | 949893 | INT: Wound | Surgery General | SHV-OSBL(u); TEM-OSBL(u); CTX-M-15; DHA-1; |
| 68 | Europe | Turkey | 954350 | Respiratory: Sputum | Pediatric General | SHV-OSBL(u); TEM-OSBL(u); CTX-M-15; |
| 69 | Latin America | Colombia | 960340 | INT: Wound | Surgery General | SHV-OSBL(u); TEM-OSBL(u); CTX-M-15; |
| 70 | South Pacific | Philippines | 966520 | Bodily Fluids: Peritoneal | Pediatric General | SHV-OSBL(u); TEM-OSBL(u); CTX-M-15; |
| 71 | Latin America | Chile | 969674 | GI: Abscess | Medicine General | SHV-OSBL(u); CTX-M-15; |
| 72 | Latin America | Chile | 969680 | INT: Wound | Medicine General | SHV-12(e); TEM-OSBL(u); |
| 73 | Europe | Russia | 975239 | Respiratory: Bronchoalveolar lavage | Pediatric ICU | SHV-OSBL(u); TEM-OSBL(u); CTX-M-15; |
| 74 | Europe | Russia | 976668 | Respiratory: Endotracheal aspirate | Medicine General | SHV-12(e); TEM-OSBL(u); CTX-M-15; |
| 75 | North America | United States | 978961 | Respiratory: Sputum | Medicine General | SHV-OSBL(u); TEM-OSBL(u); CTX-M-15; |
| 76 | Middle East | Kuwait | 984033 | INT: Wound | Medicine General | SHV-12(e); TEM-OSBL(u); CTX-M-15; |
| 77 | Latin America | Venezuela | 984345 | Respiratory: Bronchial brushing | Medicine ICU | SHV-12(e); TEM-OSBL(u); |
| 78 | Latin America | Venezuela | 984346 | Respiratory: Endotracheal aspirate | Surgery ICU | SHV-12(e); |
| 79 | Latin America | Venezuela | 984347 | Respiratory: Endotracheal aspirate | Surgery ICU | SHV-12(e); TEM-OSBL(u); CTX-M-15; |
| 80 | Asia | Korea, South | 984707 | Respiratory: Sputum | Medicine General | SHV-OSBL(u); TEM-OSBL(u); CTX-M-15; |
| 81 | Asia | Korea, South | 990767 | Respiratory: Sputum | Medicine General | SHV-OSBL(u); TEM-OSBL(u); CTX-M-15; CTX-M-2; |
| 82 | Asia | Malaysia | 993434 | Bodily Fluids: Thoracentesis | Medicine ICU | SHV-OSBL(u); TEM-OSBL(u); CTX-M-15; |

TABLE 8-continued

Summary of clinical *Klebsiella* strains which KPE33 binds.

| Region | Country | IHMA Number | Body Location | Facility Name | Molecular Summary |
|---|---|---|---|---|---|
| 83 Asia | Malaysia | 993460 | Bodily Fluids: Thoracentesis | Other | SHV-OSBL(u); TEM-OSBL(u); CTX-M-15; |
| 84 Middle East | Israel | 1007652 | INT: Wound | Medicine General | SHV-OSBL(u); TEM-OSBL(u); CTX-M-15; |
| 85 Europe | Hungary | 1031145 | Bodily Fluids: Peritoneal | Surgery General | SHV-OSBL(u); TEM-OSBL(u); CTX-M-15; |
| 86 Europe | Russia | 1049624 | Respiratory: Sputum | Medicine General | SHV-OSBL(u); TEM-OSBL(u); CTX-M-15; |
| 87 Europe | Russia | 1049665 | Respiratory: Sputum | Medicine ICU | |
| 88 Europe | Russia | 1049679 | Respiratory: Bronchoalveolar lavage | Medicine ICU | |
| 89 Europe | Russia | 1049688 | Bodily Fluids: Peritoneal | Surgery General | |
| 90 Latin America | Mexico | 1079939 | Respiratory: Endotracheal aspirate | Medicine ICU | |
| 91 Asia | Thailand | 1082628 | Respiratory: Sputum | Medicine General | |
| 92 Asia | Korea, South | 1085607 | Respiratory: Sputum | Surgery ICU | |
| 93 Africa | South Africa | 1088174 | Respiratory: Sputum | Medicine General | |
| 94 North America | United States | 1095761 | Respiratory: Sputum | Surgery ICU | |
| 95 Middle East | Israel | 1096595 | Respiratory: Sputum | Medicine General | |
| 96 Middle East | Israel | 1096648 | CVS: Blood | General Unspecified ICU | |
| 97 Latin America | Mexico | 1113727 | Respiratory: Endotracheal aspirate | Surgery ICU | |
| 98 Latin America | Mexico | 1113731 | Respiratory: Endotracheal aspirate | Surgery ICU | |
| 99 Latin America | Mexico | 1113737 | Respiratory: Endotracheal aspirate | Surgery ICU | |
| 100 Latin America | Mexico | 1113750 | Respiratory: Endotracheal aspirate | Surgery ICU | SHV-40(e); TEM-1(b); CMY-New Variant; |
| 101 South Pacific | Philippines | 1114048 | Respiratory: Endotracheal aspirate | Medicine ICU | |
| 102 Middle East | Kuwait | 1143577 | CVS: Blood | Medicine General | SHV-36(u); |
| 103 North America | United States | 872009 | Respiratory: Endotracheal aspirate | Pediatric General | SHV-12(e); |
| 104 Asia | Thailand | 872220 | INT: Wound | Emergency Room | |
| 105 North America | United States | 873434 | Respiratory: Bronchoalveolar lavage | Surgery ICU | |
| 106 North America | United States | 873455 | Respiratory: Endotracheal aspirate | Medicine General | SHV-1(b); TEM-1(b); CTX-M-15; |
| 107 Europe | France | 887005 | GI: Abscess | Surgery ICU | SHV-OSBL(u); TEM-OSBL(u); CTX-M-15; |
| 108 North America | United States | 890537 | Respiratory: Endotracheal aspirate | Surgery ICU | SHV-OSBL(u); CTX-M-2; CTX-M-14; |
| 109 Europe | Portugal | 908689 | INT: Wound | Surgery ICU | SHV-OSBL(u); CTX-M-15; |
| 110 Latin America | Argentina | 919794 | Respiratory: Bronchoalveolar lavage | Medicine ICU | SHV-OSBL(u); TEM-OSBL(u); CTX-M-15; |

TABLE 8-continued

Summary of clinical *Klebsiella* strains which KPE33 binds.

| | Region | Country | IHMA Number | Body Location | Facility Name | Molecular Summary |
|---|---|---|---|---|---|---|
| 111 | Latin America | Chile | 924355 | Respiratory: Bronchoalveolar lavage | Medicine General | SHV-OSBL(u); TEM-OSBL(u); CTX-M-15; |
| 112 | Asia | Thailand | 926453 | Respiratory: Endotracheal aspirate | Pediatric ICU | SHV-OSBL(u); TEM-OSBL(u); CTX-M-15; |
| 113 | Latin America | Mexico | 927462 | Respiratory: Bronchoalveolar lavage | Pediatric ICU | |
| 114 | Europe | Belgium | 937121 | Respiratory: Sputum | Medicine General | SHV-OSBL(u); TEM-OSBL(u); CTX-M-15; |
| 115 | Latin America | Argentina | 939906 | Respiratory: Bronchoalveolar lavage | General Unspecified ICU | SHV-OSBL(u); TEM-OSBL(u); CTX-M-15; |
| 116 | Europe | Portugal | 942859 | GI: Abscess | Surgery General | SHV-OSBL(u); TEM-OSBL(u); CTX-M-15; |
| 117 | Middle East | Israel | 948291 | Respiratory: Sputum | Medicine ICU | SHV-OSBL(u); TEM-OSBL(u); CTX-M-15; |
| 118 | Latin America | Mexico | 950081 | INT: Wound | Surgery General | SHV-12(e); |
| 119 | Latin America | Mexico | 950101 | Respiratory: Bronchoalveolar lavage | Medicine ICU | SHV-OSBL(u); TEM-OSBL(u); CTX-M-15; |
| 120 | Latin America | Mexico | 950105 | Respiratory: Bronchoalveolar lavage | Medicine ICU | SHV-OSBL(u); TEM-OSBL(u); CTX-M-15; |
| 121 | South Pacific | Philippines | 957908 | Respiratory: Endotracheal aspirate | Medicine General | SHV-OSBL(u); TEM-OSBL(u); CTX-M-15; |
| 122 | Europe | Russia | 975836 | Respiratory: Endotracheal aspirate | Surgery ICU | SHV-OSBL(u); CTX-M-15; |
| 123 | Asia | Malaysia | 993590 | Respiratory: Other | Other | SHV-OSBL(u); TEM-OSBL(u); CTX-M-15; |
| 124 | Middle East | Israel | 1007672 | Respiratory: Endotracheal aspirate | Medicine General | |
| 125 | Middle East | Israel | 1007676 | INT: Wound | Surgery General | |
| 126 | Europe | Russia | 1049686 | Respiratory: Bronchoalveolar lavage | Medicine ICU | |
| 127 | Latin America | Mexico | 1079940 | Respiratory: Bronchoalveolar lavage | Medicine General | |
| 128 | Africa | South Africa | 1088168 | Respiratory: Endotracheal aspirate | Medicine General | |
| 129 | Europe | Hungary | 1090209 | Respiratory: Endotracheal aspirate | Medicine ICU | |
| 130 | Africa | South Africa | 1093651 | Respiratory: Endotracheal aspirate | Medicine ICU | |
| 131 | Europe | Denmark | 1095278 | Respiratory: Endotracheal aspirate | Medicine ICU | |
| 132 | Europe | Hungary | 1132571 | CVS: Blood | Medicine ICU | TEM-1(b); CTX-M-15; |
| 133 | Middle East | Kuwait | 1143575 | CVS: Blood | Medicine General | SHV-28(e); TEM-1(b); CTX-M-15; |
| 134 | Africa | Kenya | 1147336 | CVS: Blood | Medicine General | SHV-11(b); TEM-1(b); DHA-1; |
| 135 | Middle East | Israel | 849171 | GU: Urine | Medicine General | |
| 136 | Middle East | Israel | 849174 | GU: Urine | Medicine General | |
| 137 | South Pacific | Philippines | 850711 | Respiratory: Sputum | Medicine General | |

TABLE 8-continued

Summary of clinical *Klebsiella* strains which KPE33 binds.

| | Region | Country | IHMA Number | Body Location | Facility Name | Molecular Summary |
|---|---|---|---|---|---|---|
| 138 | Asia | Korea, South | 857365 | Bodily Fluids: Peritoneal | Surgery General | |
| 139 | Asia | Taiwan | 862242 | Respiratory: Bronchial brushing | Medicine General | |
| 140 | North America | United States | 890179 | INT: Wound | Surgery General | |
| 141 | Asia | Taiwan | 894287 | Bodily Fluids: Peritoneal | Emergency Room | |
| 142 | Latin America | Venezuela | 929964 | GU: Urine | Pediatric General | |
| 143 | Middle East | Israel | 937430 | Respiratory: Bronchoalveolar lavage | Medicine General | |
| 144 | Europe | Czech Republic | 939344 | GU: Urine | Surgery General | |
| 145 | North America | United States | 942007 | GU: Kidneys | Medicine General | |
| 146 | Europe | Portugal | 942735 | GU: Urine | Medicine General | |
| 147 | Latin America | Mexico | 951252 | INT: Wound | Surgery General | |
| 148 | Europe | United Kingdom | 958478 | INT: Wound | Surgery General | |
| 149 | Latin America | Colombia | 961137 | Respiratory: Endotracheal aspirate | Medicine ICU | |
| 150 | Latin America | Mexico | 979902 | INT: Skin Ulcer | Medicine General | |
| 151 | North America | United States | 981359 | GU: Urine | Emergency Room | |
| 152 | Asia | Korea, South | 984668 | GU: Urinary Bladder | Medicine General | |
| 153 | Middle East | Israel | 994032 | Respiratory: Bronchoalveolar lavage | Medicine General | |
| 154 | Middle East | Kuwait | 1018958 | INT: Wound | Other | |
| 155 | Europe | Germany | 1030847 | Respiratory: Endotracheal aspirate | Surgery General | |
| 156 | Europe | Hungary | 1030963 | Respiratory: Bronchial brushing | Medicine General | |
| 157 | Asia | Japan | 1039316 | Respiratory: Sputum | Emergency Room | |
| 158 | Asia | Japan | 1039317 | Respiratory: Endotracheal aspirate | General Unspecified ICU | |
| 159 | North America | United States | 1072283 | GI: Gall Bladder | Surgery ICU | |
| 160 | North America | United States | 1073359 | Respiratory: Bronchial brushing | Medicine General | |
| 161 | Latin America | Venezuela | 1073794 | CVS: Blood | Emergency Room | |
| 162 | Latin America | Mexico | 1079921 | Respiratory: Sputum | Medicine ICU | |
| 163 | Latin America | Venezuela | 1090548 | Respiratory: Sputum | Medicine General | |
| 164 | North America | United States | 1094431 | INT: Burn | General Unspecified ICU | |
| 165 | Europe | Czech Republic | 1097501 | Respiratory: Endotracheal aspirate | Medicine ICU | |
| 166 | Europe | France | 1099046 | CVS: Blood | Surgery ICU | |
| 167 | Africa | South Africa | 1105282 | Respiratory: Endotracheal aspirate | Surgery ICU | |
| 168 | North America | United States | 1105532 | Respiratory: Endotracheal aspirate | Medicine General | |

TABLE 8-continued

Summary of clinical *Klebsiella* strains which KPE33 binds.

| | Region | Country | IHMA Number | Body Location | Facility Name | Molecular Summary |
|---|---|---|---|---|---|---|
| 169 | North America | United States | 952902 | Respiratory: Bronchoalveolar lavage | Pediatric ICU | |
| 170 | North America | United States | 952974 | Respiratory: Sputum | General Unspecified ICU | |
| 171 | North America | United States | 956266 | Respiratory: Sputum | Medicine ICU | |
| 172 | Europe | France | 1042419 | GU: Urine | Medicine General | |
| 173 | South Pacific | Australia | 1050137 | Respiratory: Sputum | Medicine ICU | |
| 174 | North America | United States | 1072281 | GI: Gall Bladder | Surgery General | |
| 175 | Asia | Taiwan | 1124198 | Respiratory: Sputum | Medicine General | |
| 176 | Africa | Kenya | 1106405 | GU: Urine | Medicine General | |
| 177 | South Pacific | Philippines | 845560 | INT: Wound | Emergency Room | |
| 178 | South Pacific | Philippines | 845617 | GI: Abscess | Medicine General | |
| 179 | Europe | Portugal | 848048 | INT: Wound | Medicine General | |
| 180 | Europe | Portugal | 848059 | Respiratory: Bronchial brushing | Pediatric ICU | SHV-OSBL(u); CTX-M-14; |
| 181 | Europe | Portugal | 848060 | Respiratory: Bronchial brushing | Surgery ICU | |
| 182 | Europe | Spain | 850152 | INT: Wound | Emergency Room | |
| 183 | Europe | United Kingdom | 867646 | Respiratory: Endotracheal aspirate | Medicine ICU | |
| 184 | Middle East | Israel | 869313 | GI: Abscess | Medicine ICU | SHV-OSBL(u); |

The isolates in rows 1-36 of Table 8 are *Klebsiella pneumoniae* carbapenam resistant (CRE) strains. The isolates in rows 37-134 of Table 8 are extended spectrum beta lactamase (ESBL) strains, and the isolates in rows 135-184 of Table 8 are antibiotic-susceptible strains.

These results demonstrate that KPE33, an anti-O1 antigen antibody, binds not only to a large and diverse group of clinical strains, but also to antibiotic resistant clinically relevant strains. These results suggest that KPE33 can be useful as a therapeutic and/or diagnostic as described herein for one or more of the *Klebsiella* strains disclosed in Table 8.

Example 15: γδ T Cell Recruitment and IL-17 Signaling Correlate with Anti-O1 Antibody Protection TLR4 signaling has been implicated in the recruitment and activation of γδ T cells, a key cell population in the innate immune defense of the mucosa. In order to examine the effect of LPS-neutralizing and LPS-non-neutralizing anti-O1 antibodies on γδ T cell recruitment, the percent of γδTCR$^+$ T cells was measured in the lungs of mice treated with anti-O1 antibodies and infected with *K. pneumoniae* (1e4 CFU Kp8045). Flow cytometry analysis revealed that early γδ T cell recruitment was inhibited by prophylaxis with 54H7, but not KPE33 (FIG. 14A). Treatment of mice with either 54H7 or KPE33 1 hour post infection did not inhibit recruitment of γδ T cells, suggesting that neutralization of early LPS signaling prevents recruitment of these beneficial cells (FIG. 14B).

γδ T cells are major producers of IL-17, which activates key antimicrobial pathways and the phagocytic function of neutrophils. IL-17A−/− mice were utilized to demonstrate the contribution of this pathway to the protection afforded by KPE33. Wild type and IL-17A−/− mice were prophylactically treated with c-IgG, 54H7, or KPE33 and infected with a lethal number of *K. pneumoniae*. No difference in survival was observed between wild type and IL-17A−/− mice prophylactically immunized with c-IgG or 54H7 (FIG. 14C). In contrast, a significant reduction in survival was observed in IL-17A−/− mice passively immunized with KPE33 compared to wild type mice that received KPE33 (FIG. 14D). These results suggest that IL-17 signaling, which is a major feature of γδ T cells, is required for optimal protection provided by KPE33.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An isolated antigen binding protein that specifically binds to *Klebsiella pneumoniae* O1 antigen comprising a set of Complementarity-Determining Regions (CDRs): HCDR1, HCDR2, HCDR3, LCDR1, LCDR2, and LCDR3 wherein the HCDR1, HCDR2, HCDR3, LCDR1, LCDR2, and LCDR3 comprise the amino acid sequences of SEQ ID NOs: 1, 2, 3, 4, 5, and 7, respectively.

2. The isolated antigen binding protein of claim 1, wherein the LCDR2 comprises the amino acid sequences of SEQ ID NO:6.

3. An isolated antigen binding protein that specifically binds to *Klebsiella pneumoniae* O1 antigen, wherein the antigen binding protein comprises a VH comprising the amino acid sequence of SEQ ID NO:8 and a VL comprising the amino acid sequence of SEQ ID NO:9.

4. The antigen binding protein of claim 1, wherein said antigen binding protein is an antibody.

5. The antigen binding protein of claim 1, wherein said antigen binding protein is an antigen-binding fragment of an antibody.

6. The antigen binding protein of claim 3, wherein said antigen binding protein is an antibody.

7. The antigen binding protein of claim 3, wherein said antigen binding protein is an antigen-binding fragment of an antibody.

8. The antigen binding protein of claim 1, which is a monoclonal antibody.

9. The antigen binding protein of claim 3, which is a monoclonal antibody.

10. An antigen binding protein produced by (i) culturing a host cell comprising a nucleic acid molecule encoding the antigen binding protein of claim 1; and (ii) isolating said antigen binding protein thereof from said cultured host cell.

11. An antigen binding protein produced by (i) culturing a host cell comprising a nucleic acid molecule encoding the antigen binding protein of claim 3; and (ii) isolating said antigen binding protein thereof from said cultured host cell.

12. A pharmaceutical composition comprising the antigen binding protein of claim 1 and a pharmaceutically acceptable excipient.

13. A pharmaceutical composition comprising the antigen binding protein of claim 3 and a pharmaceutically acceptable excipient.

14. A pharmaceutical composition comprising the antigen binding protein of claim 4 and a pharmaceutically acceptable excipient.

15. A pharmaceutical composition comprising the antigen binding protein of claim 5 and a pharmaceutically acceptable excipient.

16. The pharmaceutical composition comprising the antigen binding protein of claim 6 and a pharmaceutically acceptable excipient.

17. The pharmaceutical composition comprising the antigen binding protein of claim 7 and a pharmaceutically acceptable excipient.

18. The antigen binding protein of claim 1, wherein said antigen binding protein induces opsonophagocytic killing (OPK) of *Klebsiella* and kills *Klebsiella* via complement dependent killing as measured by a serum bactericidal assay.

19. The antigen binding protein of claim 3, wherein said antigen binding protein induces OPK killing of *Klebsiella* and kills *Klebsiella* via complement dependent killing as measured by a serum bactericidal assay.

20. The antigen binding protein of claim 1, wherein said antigen binding protein does not neutralize lipopolysaccharide (LPS).

21. The antigen binding protein of claim 3, wherein said antigen binding protein does not neutralize lipopolysaccharide (LPS).

22. The antigen binding protein of claim 18, wherein said *Klebsiella* is multi-drug resistant.

23. The antigen binding protein of claim 19, wherein said *Klebsiella* is multi-drug resistant.

24. The antigen binding protein of claim 18, wherein said *Klebsiella* is susceptible to antibiotics.

25. The antigen binding protein of claim 19, wherein said *Klebsiella* is susceptible to antibiotics.

* * * * *